United States Patent
Villota Arcos et al.

(10) Patent No.: US 10,066,269 B2
(45) Date of Patent: Sep. 4, 2018

(54) METHODS FOR DETECTING AND TREATING MULTIPLE MYELOMA

(71) Applicant: ANDES BIOTECHNOLOGIES GLOBAL, INC., Burlingame, CA (US)

(72) Inventors: Claudio E. Villota Arcos, Santiago (CL); Jaime E. Villegas Olavarria, Santiago (CL); Veronica A. Burzio Menendez, Santiago (CL); Luis O. Burzio Eriz, Santiago (CL)

(73) Assignee: ANDES BIOTECHNOLOGIES GLOBAL, INC., Burlingame, CA (US)

( * ) Notice: Subject to any disclaimer, the term of this patent is extended or adjusted under 35 U.S.C. 154(b) by 26 days.

(21) Appl. No.: 14/776,260

(22) PCT Filed: Mar. 14, 2014

(86) PCT No.: PCT/US2014/029602
§ 371 (c)(1),
(2) Date: Sep. 14, 2015

(87) PCT Pub. No.: WO2014/153206
PCT Pub. Date: Sep. 25, 2014

(65) Prior Publication Data
US 2016/0138109 A1  May 19, 2016

Related U.S. Application Data

(60) Provisional application No. 61/790,072, filed on Mar. 15, 2013, provisional application No. 61/785,269, filed on Mar. 14, 2013.

(51) Int. Cl.
| | | |
|---|---|---|
| *A61K 48/00* | (2006.01) | |
| *C07H 21/02* | (2006.01) | |
| *C07H 21/04* | (2006.01) | |
| *C12Q 1/6886* | (2018.01) | |
| *C12N 15/113* | (2010.01) | |
| *C12Q 1/6804* | (2018.01) | |

(52) U.S. Cl.
CPC .......... *C12Q 1/6886* (2013.01); *C12N 15/113* (2013.01); *C12Q 1/6804* (2013.01); *C12N 2310/113* (2013.01); *C12N 2320/30* (2013.01); *C12Q 2600/118* (2013.01); *C12Q 2600/158* (2013.01); *C12Q 2600/178* (2013.01)

(58) Field of Classification Search
CPC ............................ A61K 31/713; C12N 15/113
See application file for complete search history.

(56) References Cited

U.S. PATENT DOCUMENTS

| | | |
|---|---|---|
| 3,687,808 A | 8/1972 | Merigan, Jr. et al. |
| 5,093,246 A | 3/1992 | Cech et al. |
| 5,194,599 A | 3/1993 | Froehler et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,527,899 A | 6/1996 | Froehler |
| 5,539,082 A | 7/1996 | Nielsen et al. |
| 5,541,306 A | 7/1996 | Agrawal et al. |
| 5,550,111 A | 8/1996 | Suhadolnik et al. |
| 5,552,540 A | 9/1996 | Haralambidis |
| 5,563,253 A | 10/1996 | Agrawal et al. |
| 5,565,555 A | 10/1996 | Froehler et al. |
| 5,571,799 A | 11/1996 | Tkachuk et al. |
| 5,587,361 A | 12/1996 | Cook et al. |
| 5,587,469 A | 12/1996 | Cook et al. |
| 5,594,121 A | 1/1997 | Froehler et al. |
| 5,596,086 A | 1/1997 | Matteucci et al. |
| 5,596,091 A | 1/1997 | Switzer |
| 5,602,240 A | 2/1997 | Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,633,360 A | 5/1997 | Bischofberger et al. |
| 5,645,985 A | 7/1997 | Froehler et al. |

(Continued)

FOREIGN PATENT DOCUMENTS

| | | |
|---|---|---|
| WO | WO-98/55495 A2 | 12/1998 |
| WO | WO-98/55495 A3 | 12/1998 |

(Continued)

OTHER PUBLICATIONS

Elbashir S. M. et al. (May 24, 2001). "Duplexes of 21-nucleotide RNAs mediate RNA interference in cultured mammalian cells," *Nature* 411(6836):494-498.

Englisch, U. et al. (Jun. 1991). "Chemically Modified Oligonucleotides as Probes and Inhibitors," *Angewandte Chemie International Edition* 30(6):613-629.

Harousseau, J. L. (Aug. 5, 2009). "Maintenance therapy in multiple myeloma," *Hematol. Rep.* 1(2)(e12):65-69.

Haseloff, J. et al. (Oct. 15, 1989). "Sequences required for self-catalysed cleavage of the satellite RNA of tobacco ringspot virus," *Gene* 82(1):43-52.

International Search Report dated Nov. 17, 2014, for PCT Patent Application No. PCT/US2014/029602 filed on Mar. 14, 2014, six pages.

(Continued)

*Primary Examiner* — Amy H Bowman
(74) *Attorney, Agent, or Firm* — Mintz Levin Cohn Ferris Glovsky and Popeo P.C.

(57) ABSTRACT

The invention provides methods for using the expression levels and subcellular localization of non-coding mitochondrial RNAs to select individuals or subpopulation of individuals for treatment with an anticancer therapy for multiple myeloma. Additional methods provided herein are useful for determining whether an individual in remission for multiple myeloma following successful treatment will be likely to suffer a relapse as well as to identify individuals who have suffered a relapse of multiple myeloma.

10 Claims, 11 Drawing Sheets
Specification includes a Sequence Listing.

(56) References Cited

U.S. PATENT DOCUMENTS

| | | | |
|---|---|---|---|
| 5,646,269 | A | 7/1997 | Matteucci et al. |
| 5,663,312 | A | 9/1997 | Chaturvedula |
| 5,672,697 | A | 9/1997 | Buhr et al. |
| 5,677,437 | A | 10/1997 | Teng et al. |
| 5,677,439 | A | 10/1997 | Weis et al. |
| 5,681,941 | A | 10/1997 | Cook et al. |
| 5,714,331 | A | 2/1998 | Buchardt et al. |
| 5,719,262 | A | 2/1998 | Buchardt et al. |
| 5,721,218 | A | 2/1998 | Froehler |
| 5,763,588 | A | 6/1998 | Matteucci et al. |
| 5,792,608 | A | 8/1998 | Swaminathan et al. |
| 5,830,653 | A | 11/1998 | Froehler et al. |
| 6,005,096 | A | 12/1999 | Matteucci et al. |
| 7,399,845 | B2 | 7/2008 | Seth et al. |
| 8,318,686 | B2 | 11/2012 | Burzio et al. |
| 8,614,095 | B2 | 12/2013 | Radovanovic et al. |
| 8,895,719 | B2 | 11/2014 | Burzio et al. |
| 2004/0224389 | A1 | 11/2004 | Bellgrau et al. |
| 2006/0241033 | A1* | 10/2006 | Burzio et al. ........ C12N 15/113 |
| 2010/0292099 | A1 | 11/2010 | Dreyfus et al. |
| 2011/0280849 | A1 | 11/2011 | Zhang et al. |
| 2012/0325090 | A1 | 12/2012 | Takahashi |
| 2015/0064700 | A1 | 3/2015 | Burzio et al. |
| 2016/0138015 | A1 | 5/2016 | Burzio Eriz et al. |

FOREIGN PATENT DOCUMENTS

| | | | |
|---|---|---|---|
| WO | WO-98/55495 | B1 | 12/1998 |
| WO | WO-2004/100953 | A1 | 11/2004 |
| WO | WO-2005/001030 | A2 | 1/2005 |
| WO | WO-2005/001030 | A3 | 1/2005 |
| WO | WO-2005/082409 | A1 | 9/2005 |
| WO | WO-2007/046511 | A1 | 4/2007 |
| WO | WO-2009/155135 | A1 | 12/2009 |
| WO | WO-2013/021032 | A1 | 2/2013 |
| WO | WO-2014/153209 | A1 | 9/2014 |
| WO | WO-2014/153209 | A8 | 9/2014 |

OTHER PUBLICATIONS

Kroschwitz, J. I. ed. (1990). "Polynucleotides" *Concise Encyclopedia of Polymer Science and Engineering*, John Wiley & Sons, Inc.: NY, pp. 858-859.

Kyle, R. A. et al. (Mar. 15, 2008). "Multiple myeloma," *Blood* 111(6):2962-2972.

Landerer, E. et al. (Aug. 2011, e-pub. Feb. 24, 2011). "Nuclear localization of the mitochondrial ncRNAs in normal and cancer cells," *Cell Oncol.* 34(4):297-305.

Lu, P. Y. et al. (Jun. 2003). "siRNA-mediated antitumorigenesis for drug target validation and therapeutics," *Curr. Opin. Mol. Ther.* 5(3):225-234.

McManus, M. T. et al. (Oct. 2002). "Gene silencing in mammals by small interfering RNAs," *Nat. Rev. Genet.* 3(10):737-747.

Nielsen, P. E. et al. (Dec. 6, 1991). "Sequence-selective recognition of DNA by strand displacement with a thymine-substituted polyamide," *Science* 254(5037):1497-1500.

Rossi, J. J. (Jun. 1994). "Practical ribozymes. Making ribozymes work in cells," *Curr. Biol.* 4(5):469-471.

Sanghvi, Y. S. (1993). "Heterocyclic Base Modifications in Nucleic Acids and Their Applications in Antisense Oligonucleotides" Chapter 15 in *Antisense Research and Applications*, Crooke, S. T. et al. eds., CRC Press, Inc.: Boca Raton, FL, pp. 273-288.

Wacheck, V. et al. (2003). "Small interfering RNA targeting bcl-2 sensitizes malignant melanoma," *Oligonucleotides* 13(5):393-400.

Written Opinion dated Nov. 17, 2014, for PCT Patent Application No. PCT/US2014/029602 filed on Mar. 14, 2014, eight pages.

Zaug, A. J. et al. (May 11, 1984). "A labile phosphodiester bond at the ligation junction in a circular intervening sequence RNA," *Science* 224(4649):574-578.

U.S. Appl. No. 14/775,654, Internationally filed Mar. 14, 2014, by Burzio et al.

U.S. Appl. No. 15/139,255, filed Apr. 26, 2016, by Burzio et al.

Ahmed, N. et al. (Sep. 25, 2013). "Getting to know ovarian cancer ascites: opportunities for targeted therapy-based translational research," *Front Oncol.* 3(Article 256):1-12.

Chen, K. et al. (Jun. 2013, e-pub. May 20, 2013). "Understanding and targeting cancer stem cells: therapeutic implications and challenges," *Acta. Pharmacol. Sin.* 34(6):732-740.

Clarke, M. F. et al. (Oct. 1, 2006, e-pub. Sep. 21, 2006). "Cancer stem cells—perspectives on current status and future directions: AACR Workshop on cancer stem cells," *Cancer Res.* 66(19):9339-9344.

De Sanjosé, S. et al. (Nov. 2013, e-pub. Jul. 22, 2013). "Worldwide human papillomavirus genotype attribution in over 2000 cases of intraepithelial and invasive lesions of the vulva," *Eur. J. Cancer* 49(16):3450-3461.

Ding, Z. et al. (Sep. 15, 2000). "Human papillomavirus type 16-immortalized endocervical cells selected for resistance to cisplatin are malignantly transformed and have a multidrug resistance phenotype," *Int. J. Cancer* 87(6):818-823.

Domingo-Domenech, J. et al. (Sep. 11, 2012). "Suppression of acquired docetaxel resistance in prostate cancer through depletion of notch- and hedgehog-dependent tumor-initiating cells," *Cancer Cell* 22(3):373-388.

Feng, D. et al. (Nov. 2009). "Identification and characterization of cancer stem-like cells from primary carcinoma of the cervix uteri," *Oncol. Rep.* 22(5):1129-1134.

International Search Report dated Aug. 21, 2014, for PCT Patent Application No. PCT/US2014/029606 filed on Mar. 14, 2014, 4 pages.

Mani S. A. et al. (May 16, 2008). "The epithelial-mesenchymal transition generates cells with properties of stem cells," *Cell* 133(4):704-715.

Mukhopadhyay, P. et al. (Nov. 12, 2013). "Heterogeneity of functional properties of Clone 66 murine breast cancer cells expressing various stem cell phenotypes," *PloS One* 8(11) (e78725) pp. 1-15.

Munoz, N. et al. (Feb. 6, 2003). "Epidemiologic classification of human papillomavirus types associated with cervical cancer," *N. Engl. J. Med.* 348(6):518-527.

Ohata, H. et al. (Oct. 1, 2012, e-pub. Sep. 20, 2012). "Induction of the stem-like cell regulator CD44 by Rho kinase inhibition contributes to the maintenance of colon cancer-initiating cells," *Cancer Res.* 72(19):5101-5110.

Perantoni, A. 0. (1998). "Carcinogenesis" Chapter 3 in *The Biological Basis of Cancer* McKinnell, R. G. et al. eds., Cambridge University Press: Cambridge, UK, p. 79-114.

Ponti, D. et al. (Jul. 1, 2005). "Isolation and in vitro propagation of tumorigenic breast cancer cells with stem/progenitor cell properties," *Cancer Res.* 65(13):5506-5511.

Singh, S. K. et al. (Sep. 15, 2003). "Identification of a cancer stem cell in human brain tumors," *Cancer Res.* 63(18):5821-5828.

Tjalma, W. A. et al. (Feb. 15, 2013, e-pub. Jul. 24, 2012). "Differences in human papillomavirus type distribution in high-grade cervical intraepithelial neoplasia and invasive cervical cancer in Europe," *Int. J. Cancer* 132(4):854-867.

Tjalma, W. A. et al. (Jan. 2012). "Don't forget HPV-45 in cervical cancer screening," *Am. J. Clin. Pathol.* 137(1):161-163.

Walboomers, M. et al. (Sep. 1999). "Human papillomavirus is a necessary cause of invasive cervical cancer worldwide," *J. Pathol.* 189(1):12-19.

Written Opinion dated Aug. 21, 2014, for PCT Patent Application No. PCT/US2014/029606 filed on Mar. 14, 2014, 4 pages.

Zhang, S. et al. (Jun. 1, 2008). "Identification and characterization of ovarian cancer-initiating cells from primary human tumors," *Cancer Res.* 68(11):4311-4320.

Bhatnagar, B. et al. (2013). "Controversies in Autologous Stem Cell Transplantation for the Treatment of Multiple Myeloma," Chapter 8 in *Innovations in Stem Cell Transplantation*, pp. 195-220.

Mikhael, J.R. et al. (Apr. 2013). "Management of newly diagnosed symptomatic multiple myeloma: updated Mayo Stratification of Myeloma and Risk-Adapted Therapy (mSMART) consensus guidelines 2013," *Mayo Clin Proc* 88(4):360-376.

(56) References Cited

OTHER PUBLICATIONS

Plesner, T. et al. (2012). "Daratumumab, a $CD_38$ Monoclonal Antibody in Patients with Multiple Myeloma-Data From a Dose-Escalation Phase I/II Study," *Blood* 120:Abstract 73.
Varas, M. et al. (Nov. 2011). "Abstract B181: A Lentivirus-Encoding shRNA Targeting a Noncoding Mitochondrial RNA Inhibits Melanoma Tumor Growth and Metastasis in a Mouse Model in vivo," *Molecular Cancer Therapeutics* vol. 10, No. 11 Supplement, Abstract B181, 4 pages.

\* cited by examiner

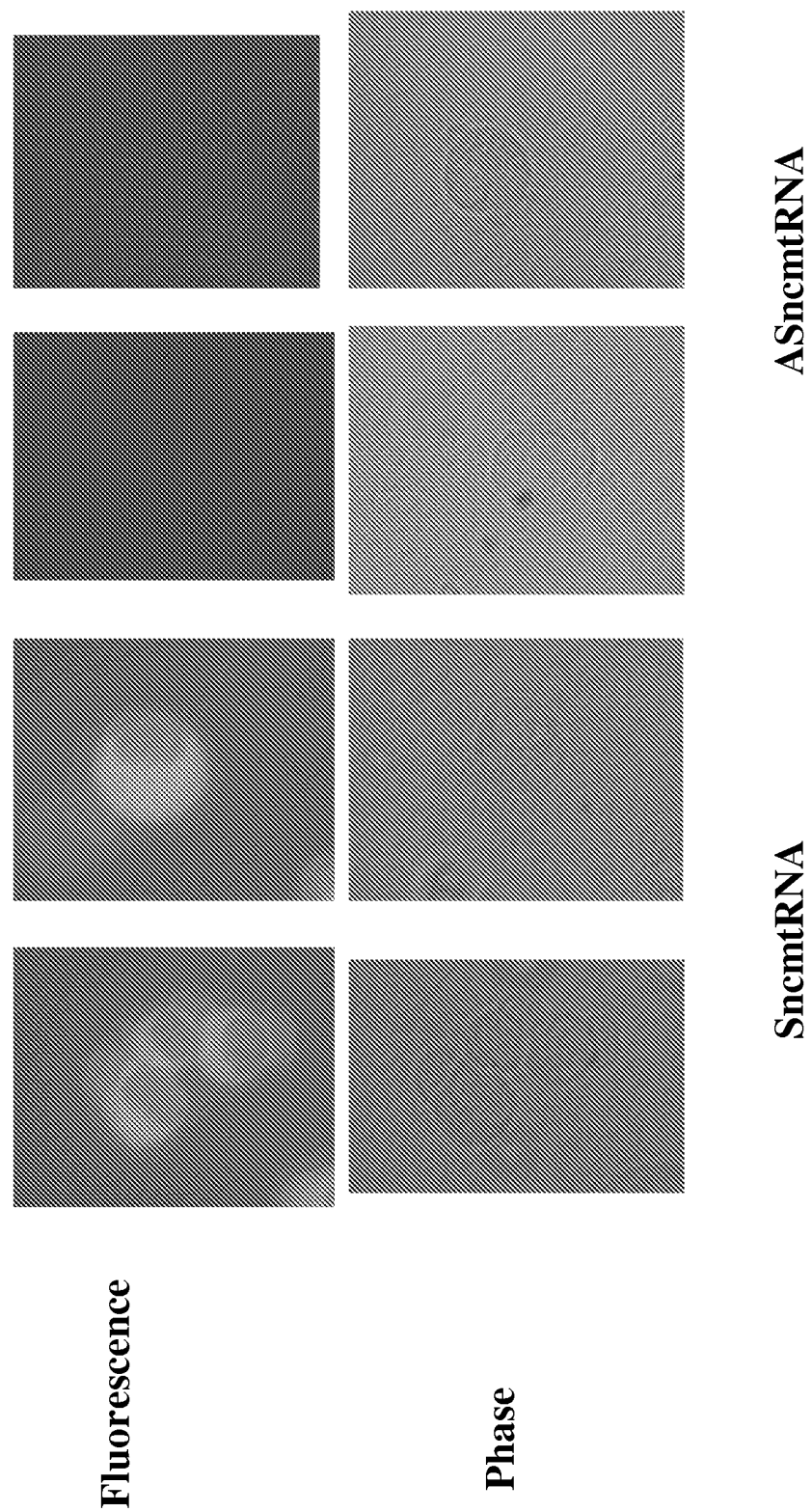

METHODS FOR DETECTING AND TREATING MULTIPLE MYELOMA

CROSS REFERENCE TO RELATED APPLICATIONS

This application is a National Phase filing under 35 U.S.C. § 371 of International Application No. PCT/US2014/029602, filed Mar. 14, 2014, which claims priority to U.S. Provisional Patent Application No. 61/785,269, filed Mar. 14, 2013 and U.S. Provisional Patent Application No. 61/790,072, filed Mar. 15, 2013, the entire contents of each of which are incorporated by reference herein in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 707402000230SEQLIST.TXT, date recorded: Jan. 29, 2016, size: 49 KB).

FIELD OF THE INVENTION

This invention provides methods for detecting and treating multiple myeloma based, in part, on the expression and subcellular localization of non-coding mitochondrial RNAs expressed in plasmocytes isolated from the bone marrow of individuals diagnosed with or thought to have multiple myeloma.

BACKGROUND OF THE INVENTION

Multiple myeloma is a neoplastic disease characterized by infiltration of bone and bone marrow by myeloma cells forming multiple tumor masses that lead to pathological fractures. The condition is usually progressive and fatal. Symptoms include anemia, renal damage and high globulin levels in blood and increased susceptibility to bacterial infections. The impaired abnormal immunoglobulin production observed in multiple myeloma may be due to the presence of a monocyte or macrophage that suppresses the maturation of normal B-lymphocytes into antibody secreting cells. Life expectancy is related to extent of the disease at diagnosis and response to treatment. The median life expectancy of responding patients is two years. High levels of myeloma protein in serum or urine, bone lesions, hypercalcemia, pancytopenia, and renal failure are unfavorable signs.

Although Multiple Myeloma remains incurable, the development of novel therapies has dramatically increased response rates and survival over recent years. Despite major advances in our understanding of this complex disease, a standard remission-induction therapeutic approach is taken to patients in similar categories of age and performance status in the great majority of treatment centers. High dose chemotherapy with autologous stem cell transplant remains the standard therapy for younger patients.

Monoclonal gammopathy of undetermined significance (MGUS) and multiple myeloma are the most frequent forms of monoclonal gammopathies. Monoclonal gammopathy of undetermined significance is the most common plasma cell dyscrasia with an incidence of up to 10% of population over age 75. The molecular basis of monoclonal gammopathy of undetermined significance and multiple myeloma are not very well understood and it is not easy to differentiate the two disorders. The diagnosis of multiple myeloma or monoclonal gammopathy of undetermined significance is identical in ⅔ of cases using classification systems that are based on a combination of clinical criteria such as the amount of bone marrow plasmocytosis, the concentration of monoclonal immunoglobulin in urine or serum, and the presence of bone lesions. Especially in early phases of multiple myeloma, the differential diagnosis is associated with a certain degree of uncertainty.

Furthermore, in the diagnosis of multiple myeloma, the clinician must exclude other disorders in which a plasma cell reaction may occur such as rheumatoid arthritis and connective tissue disorders, or metastatic carcinoma where the patient may have osteolytic lesions associated with bone metastases. Therefore, given that multiple myeloma is thought to have an extended latency and clinical features are recognized many years after the development of the malignancy, new molecular diagnostic techniques are needed in screening for the disease and providing differential diagnosis for multiple myeloma. Thus, there is a need for new and accurate methods for differentially diagnosing and identifying distinct and prognostically relevant clinical subgroups of multiple myeloma.

Complicating the search for such new methods is the fact that multiple myeloma cells are endowed with a multiplicity of anti-apoptotic signaling mechanisms that account for their resistance to current chemotherapy and thus the ultimately fatal outcome for most patients. While aneuploidy by interphase fluorescence in situ hybridization (FISH) and DNA flow cytometry are observed in >90% of cases, cytogenetic abnormalities in this typically hypoproliferative tumor are informative in only about 30% of cases and are typically complex, involving on average seven different chromosomes. It has therefore been difficult to establish correlations between genetic abnormalities and clinical outcomes.

Consequently, given the unreliability of individual gene expression within multiple myeloma tumor cells, there exists a need for a biomarker whose measurement can not only predict the likelihood that an individual has multiple myeloma and will likely benefit from anticancer therapies, but is also useful for determining whether individuals or subpopulations of individuals who are currently in remission following successful anticancer therapy for multiple myeloma are likely to suffer relapse. Such a marker would be helpful for guiding health care professionals involved in the treatment of an individual suffering from or thought to have multiple myeloma. Consequently, a marker of this sort would be useful not only for diagnostic purposes, but also to track prognosis following the initiation of treatment and establishment of remission.

This invention provides such a biomarker and uses the expression and subcellular localization of non-coding mitochondrial RNAs (ncmtRNAs) within plasmocytes isolated from bone marrow to select individuals or subpopulations of individuals who will benefit from an anti-multiple myeloma therapy as well as to identify individuals in remission who are likely to relapse or who have relapsed following remission.

Throughout this specification, various patents, patent applications and other types of publications (e.g., journal articles) are referenced. The disclosure of all patents, patent applications, and publications cited herein are hereby incorporated by reference in their entirety for all purposes.

SUMMARY OF THE INVENTION

The invention provided herein discloses, inter alia, methods for using the expression and subcellular localization of a non-coding mitochondrial RNAs (ncmtRNAs) to select individuals or subpopulations of individuals suspected of having or developing multiple myeloma that will benefit from anticancer therapies as well as methods for using ncmtRNA expression levels in plasmocytes isolated from the bone marrow of individuals to guide the treatment of individuals having or suspected of developing multiple myeloma.

Accordingly, in one aspect, the provided herein are methods for treating multiple myeloma in an individual in need thereof comprising: measuring the expression of a sense non-coding mitochondrial RNA (SncmtRNA) and an antisense non-coding mitochondrial RNA (ASncmtRNA) in plasmocytes isolated from the bone barrow of the individual, wherein the expression of both a SncmtRNA and an ASncmtRNA indicates that the individual does not have multiple myeloma and wherein the expression of a SncmtRNA and the lack of expression of an ASncmtRNA indicates that the individual has multiple myeloma; and treating the individual with one or more anti-cancer therapeutics if the plasmocytes of the individual express only the SncmtRNA and do not express the ASncmtRNA. In another aspect, provided herein are methods for treating multiple myeloma in an individual in need thereof comprising: treating the individual with one or more anti-cancer therapeutics, wherein prior to treatment it has been determined that plasmocytes isolated from the bone barrow of the individual express a sense non-coding mitochondrial RNA (SncmtRNA) and do not express an antisense non-coding mitochondrial RNA (ASncmtRNA). In some embodiments of any of the embodiments provided herein, the anti-cancer therapeutics comprise one or more oligonucleotides sufficiently complementary to a human non-coding mitochondrial chimeric RNA molecule comprising (a) an antisense 16S mitochondrial ribosomal RNA covalently linked at its 5' end to the 3' end of a polynucleotide with an inverted repeat sequence or (b) a sense 16S mitochondrial ribosomal RNA covalently linked at its 5' end to the 3' end of a polynucleotide with an inverted repeat sequence, wherein the oligonucleotides are able to hybridize with the mitochondrial chimeric RNA molecules to form a stable duplex. In some embodiments of any of the embodiments provided herein, wherein the anti-cancer therapeutics comprise remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bortezomib (Velcade®), bisphosphonate, arsenic trioxide, vincristine, doxorubicin (Doxil®), paclitaxel, ganciclovir, adriamycin, estrainustine sodium phosphate (Emcyt®), sulindac, and etoposide. In some embodiments of any of the embodiments provided herein, the multiple myeloma relapsed after treatment with one or more of bortezomib (Velcade®), cyclophosphamide, dexamethasone, doxorubicin, interferon-alpha, lenalidomide, melphalan, pegylated interferon-alpha, prednisone, thalidomide, and vincristine. In some embodiments of any of the embodiments provided herein, said anti-cancer therapy is administered as part of a salvage therapy in treating patients wherein the multiple myeloma has become refractory to other drugs. In some embodiments of any of the embodiments provided herein, the method further comprises administering one or more additional therapies. In some embodiments, the one or more additional therapies comprise allogenic stem cell transplant therapy. In some embodiments, the one or more additional therapies comprise autologous stem cell transplant therapy. In some embodiments, hematopoietic stem-cells and/or bone marrow for use in autologous stem cell transplantation are treated with an effective amount of one or more oligonucleotides sufficiently complementary to an ASncmtRNA or SncmtRNA molecule to form a stable duplex prior to transplantation into the affected individual. In some embodiments of any of the embodiments provided herein, the ASncmtRNA comprises a human mitochondrial chimeric RNA molecule comprising an antisense 16S mitochondrial ribosomal RNA covalently linked at its 5' end to the 3' end of a polynucleotide with an inverted repeat sequence. In some embodiments, the ASncmtRNA comprises one or more nucleotide sequences selected from the group consisting of SEQ ID NO:4, SEQ ID NO:5, and SEQ ID NO:6. In some embodiments of any of the embodiments provided herein, the SncmtRNA comprises a human mitochondrial chimeric RNA molecule comprising a sense 16S mitochondrial ribosomal RNA covalently linked at its 5' end to the 3' end of a polynucleotide with an inverted repeat sequence. In some embodiments, the SncmtRNA comprises one or more nucleotide sequences selected from the group consisting of SEQ ID NO:1, SEQ ID NO:2, and SEQ ID NO:3. In some embodiments of any of the embodiments provided herein, expression of the SncmtRNA or ASncmtRNA is measured by RT-PCR or another PCR-based method, Northern Blot, in situ hybridization, or SAGE. In some embodiments, the SncmtRNA or ASncmtRNA is measured by quantitative RT-PCR (qRT-PCR). In some embodiments, the SncmtRNA or ASncmtRNA is measured by in situ hybridization. In some embodiments of any of the embodiments provided herein, the subcellular localization of the SncmtRNA or ASncmtRNA is measured by in situ hybridization.

In other aspects, provided herein are methods for preventing relapse of multiple myeloma in an individual in need thereof comprising: (a) measuring the subcellular localization of a sense non-coding mitochondrial RNA (SncmtRNA) in plasmocytes isolated from the bone barrow of the individual, wherein the cytoplasmic localization of the SncmtRNA indicates that the individual is in remission; and (b) treating the individual with one or more maintenance anti-cancer therapeutics if the SncmtRNA is localized to the cytoplasm of the plasmocytes. In another aspect, provided herein are methods for preventing relapse of multiple myeloma in an individual in need thereof comprising: treating the individual with one or more maintenance anti-cancer therapeutics, wherein prior to treatment it has been determined that plasmocytes isolated from the bone barrow of the individual exhibit subcellular cytoplasmic localization of a sense non-coding mitochondrial RNA (SncmtRNA). In some embodiments of any of the embodiments provided herein, the anti-cancer therapeutics comprise one or more oligonucleotides sufficiently complementary to a human non-coding mitochondrial chimeric RNA molecule comprising (a) an antisense 16S mitochondrial ribosomal RNA covalently linked at its 5' end to the 3' end of a polynucleotide with an inverted repeat sequence or (b) a sense 16S mitochondrial ribosomal RNA covalently linked at its 5' end to the 3' end of a polynucleotide with an inverted repeat sequence, wherein the oligonucleotides are able to hybridize with the mitochondrial chimeric RNA molecules to form a stable duplex. In some embodiments of any of the embodiments provided herein, wherein the anti-cancer therapeutics comprise remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bortezomib (Velcade®), bisphosphonate, arsenic trioxide, vincristine, doxorubicin (Doxil®), paclitaxel, ganciclovir, adriamycin, estrainustine sodium phosphate (Emcyt®), sulindac, and etoposide. In some embodiments of any of the embodiments provided herein, the multiple myeloma relapsed after treatment with one or more of bortezomib (Velcade®), cyclophosphamide, dexamethasone, doxorubicin, interferon-alpha, lenalidomide, melphalan, pegylated interferon-alpha, prednisone, thalidomide, and vincristine. In some embodiments of any of the embodiments provided herein, said anti-cancer therapy is administered as part of a salvage therapy in treating patients wherein the multiple myeloma has become refractory to other drugs. In some embodiments of any of the embodiments provided herein, the method further comprises administering one or more additional therapies. In some embodiments, the one or more additional therapies comprise allogenic stem cell transplant therapy. In some embodiments, the one or more additional therapies comprise autologous stem cell transplant therapy. In some embodiments, hematopoietic stem-cells and/or bone marrow for use in autologous stem cell transplantation are treated with an effective amount of one or more oligonucleotides sufficiently complementary to an ASncmtRNA or SncmtRNA molecule to form a stable duplex prior to transplantation into the affected individual. In some embodiments of any of the embodiments provided herein, the ASncmtRNA comprises a human mitochondrial chimeric RNA molecule comprising an antisense 16S mitochondrial ribosomal RNA covalently linked at its 5' end to the 3' end of a polynucleotide with an inverted repeat sequence. In some embodiments, the ASncmtRNA comprises one or more nucleotide sequences selected from the group consisting of SEQ ID NO:4, SEQ ID NO:5, and SEQ ID NO:6. In some embodiments of any of the embodiments provided herein, the SncmtRNA comprises a human mitochondrial chimeric RNA molecule comprising a sense 16S mitochondrial ribosomal RNA covalently linked at its 5' end to the 3' end of a polynucleotide with an inverted repeat sequence. In some embodiments, the SncmtRNA comprises one or more nucleotide sequences selected from the group consisting of SEQ ID NO:1, SEQ ID NO:2, and SEQ ID NO:3. In some embodiments of any of the embodiments provided herein, expression of the SncmtRNA or ASncmtRNA is measured by RT-PCR or another PCR-based method, Northern Blot, in situ hybridization, or SAGE. In some embodiments, the SncmtRNA or ASncmtRNA is measured by quantitative RT-PCR (qRT-PCR). In some embodiments, the SncmtRNA or ASncmtRNA is measured by in situ hybridization. In some embodiments of any of the embodiments provided herein, the subcellular localization of the SncmtRNA or ASncmtRNA is measured by in situ hybridization.

In still other aspects, provided herein are methods for treating relapsed multiple myeloma in an individual thereof comprising: (a) measuring the subcellular localization of a sense non-coding mitochondrial RNA (SncmtRNA) in plasmocytes isolated from the bone barrow of the individual, wherein the (i) nuclear or (ii) cytoplasmic and nuclear localization of the SncmtRNA indicates that the individual has relapsed; and (b) treating the individual with one or more anti-cancer therapeutics if the SncmtRNA is localized to (i) the nuclei or (ii) cytoplasm and nuclei of the plasmocytes. In another aspect, provided herein are methods for treating relapsed multiple myeloma in an individual thereof comprising: treating the individual with one or more anti-cancer therapeutics, wherein prior to treatment it has been determined that plasmocytes isolated from the bone barrow of the individual exhibit (i) nuclear or (ii) cytoplasmic and nuclear subcellular localization of a sense non-coding mitochondrial RNA (SncmtRNA). In some embodiments of any of the embodiments provided herein, the anti-cancer therapeutics comprise one or more oligonucleotides sufficiently complementary to a human non-coding mitochondrial chimeric RNA molecule comprising (a) an antisense 16S mitochondrial ribosomal RNA covalently linked at its 5' end to the 3' end of a polynucleotide with an inverted repeat sequence or (b) a sense 16S mitochondrial ribosomal RNA covalently linked at its 5' end to the 3' end of a polynucleotide with an inverted repeat sequence, wherein the oligonucleotides are able to hybridize with the mitochondrial chimeric RNA molecules to form a stable duplex. In some embodiments of any of the embodiments provided herein, wherein the anti-cancer therapeutics comprise remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bortezomib (Velcade®), bisphosphonate, arsenic trioxide, vincristine, doxorubicin (Doxil®), paclitaxel, ganciclovir, adriamycin, estrainustine sodium phosphate (Emcyt®), sulindac, and etoposide. In some embodiments of any of the embodiments provided herein, the multiple myeloma relapsed after treatment with one or more of bortezomib (Velcade®), cyclophosphamide, dexamethasone, doxorubicin, interferon-alpha, lenalidomide, melphalan, pegylated interferon-alpha, prednisone, thalidomide, and vincristine. In some embodiments of any of the embodiments provided herein, said anti-cancer therapy is administered as part of a salvage therapy in treating patients wherein the multiple myeloma has become refractory to other drugs. In some embodiments of any of the embodiments provided herein, the method further comprises administering one or more additional therapies. In some embodiments, the one or more additional therapies comprise allogenic stem cell transplant therapy. In some embodiments, the one or more additional therapies comprise autologous stem cell transplant therapy. In some embodiments, hematopoietic stem-cells and/or bone marrow for use in autologous stem cell transplantation are treated with an effective amount of one or more oligonucleotides sufficiently complementary to an ASncmtRNA or SncmtRNA molecule to form a stable duplex prior to transplantation into the affected individual. In some embodiments of any of the embodiments provided herein, the ASncmtRNA comprises a human mitochondrial chimeric RNA molecule comprising an antisense 16S mitochondrial ribosomal RNA covalently linked at its 5' end to the 3' end of a polynucleotide with an inverted repeat sequence. In some embodiments, the ASncmtRNA comprises one or more nucleotide sequences selected from the group consisting of SEQ ID NO:4, SEQ ID NO:5, and SEQ ID NO:6. In some embodiments of any of the embodiments provided herein, the SncmtRNA comprises a human mitochondrial chimeric RNA molecule comprising a sense 16S mitochondrial ribosomal RNA covalently linked at its 5' end to the 3' end of a polynucleotide with an inverted repeat sequence. In some embodiments, the SncmtRNA comprises one or more nucleotide sequences selected from the group consisting of SEQ ID NO:1, SEQ ID NO:2, and SEQ ID NO:3. In some embodiments of any of the embodiments provided herein, expression of the SncmtRNA or ASncmtRNA is measured by RT-PCR or another PCR-based method, Northern Blot, in situ hybridization, or SAGE. In some embodiments, the SncmtRNA or ASncmtRNA is measured by quantitative RT-PCR (qRT-PCR). In some embodiments, the SncmtRNA or ASncmtRNA is measured by in situ hybridization. In some embodiments of any of the embodiments provided herein, the subcellular localization of the SncmtRNA or ASncmtRNA is measured by in situ hybridization.

In other aspects, provided herein are methods for assessing a likelihood of a beneficial response to an anti-multiple myeloma therapy in an individual suspected of having or developing multiple myeloma, the method comprising: measuring the subcellular localization of a sense non-coding mitochondrial RNA (SncmtRNA) in plasmocytes isolated from the bone barrow of the individual, wherein the cytoplasmic subcellular localization of the SncmtRNA indicates a beneficial response to the anti-multiple myeloma therapy. In some embodiments of any of the embodiments provided herein, the SncmtRNA comprises a human mitochondrial chimeric RNA molecule comprising a sense 16S mitochondrial ribosomal RNA covalently linked at its 5' end to the 3' end of a polynucleotide with an inverted repeat sequence. In some embodiments, the SncmtRNA comprises one or more nucleotide sequences selected from the group consisting of SEQ ID NO:1, SEQ ID NO:2, and SEQ ID NO:3. In some embodiments of any of the embodiments provided herein, the subcellular localization of the SncmtRNA or ASncmtRNA is measured by in situ hybridization.

In another aspect, provided herein are methods for diagnosing multiple myeloma in an individual comprising: measuring the expression of a sense non-coding mitochondrial RNA (SncmtRNA) and an antisense non-coding mitochondrial RNA (ASncmtRNA) in plasmocytes isolated from the bone barrow of the individual, wherein the expression of both a SncmtRNA and an ASncmtRNA indicates that the individual does not have multiple myeloma and wherein the expression of a SncmtRNA and the lack of expression of an ASncmtRNA indicates that the individual has multiple myeloma. In other aspects, provided herein are methods for determining whether an individual diagnosed with multiple myeloma that is in remission will relapse, the method comprising: measuring the subcellular localization of a sense non-coding mitochondrial RNA (SncmtRNA) in plasmocytes isolated from the bone barrow of the individual, wherein (a) cytoplasmic localization of the SncmtRNA indicates that the individual is in remission and (b) nuclear or cytoplasmic and nuclear localization of the SncmtRNA indicates that the individual will relapse. In some embodiments of any of the embodiments provided herein, the ASncmtRNA comprises a human mitochondrial chimeric RNA molecule comprising an antisense 16S mitochondrial ribosomal RNA covalently linked at its 5' end to the 3' end of a polynucleotide with an inverted repeat sequence. In some embodiments, wherein the ASncmtRNA comprises one or more nucleotide sequences selected from the group consisting of SEQ ID NO:4, SEQ ID NO:5, and SEQ ID NO:6. In some embodiments of any of the embodiments provided herein, the SncmtRNA comprises a human mitochondrial chimeric RNA molecule comprising a sense 16S mitochondrial ribosomal RNA covalently linked at its 5' end to the 3' end of a polynucleotide with an inverted repeat sequence. In some embodiments, the SncmtRNA comprises one or more nucleotide sequences selected from the group consisting of SEQ ID NO:1, SEQ ID NO:2, and SEQ ID NO:3. In some embodiments of any of the embodiments provided herein, expression of the SncmtRNA or ASncmtRNA is measured by RT-PCR or another PCR-based method, Northern Blot, in situ hybridization, or SAGE. In some embodiments, expression of the SncmtRNA or ASncmtRNA is measured by quantitative RT-PCR (qRT-PCR). In some embodiments, expression of the SncmtRNA or ASncmtRNA is measured by in situ hybridization. In some embodiments of any of the embodiments provided herein, the subcellular localization of the SncmtRNA or ASncmtRNA is measured by in situ hybridization.

In still other aspects, provided herein are kits for diagnosing multiple myeloma, the kit comprising one or more of: (a) one or more oligonucleotides sufficiently complementary to a human mitochondrial chimeric RNA molecule comprising (i) an antisense 16S mitochondrial ribosomal RNA covalently linked at its 5' end to the 3' end of a polynucleotide with an inverted repeat sequence or (ii) a sense 16S mitochondrial ribosomal RNA covalently linked at its 5' end to the 3' end of a polynucleotide with an inverted repeat sequence, wherein the oligonucleotides are able to hybridize with the mitochondrial chimeric RNA molecules to form a stable duplex; (b) a conjugated antibody reagent for label detection; (c) hybridization and wash buffer; and/or (d) one or more slides of fixed plasmocytes (i) isolated from an individual diagnosed with multiple myeloma or a multiple myeloma cell line as a positive control and (ii) isolated from an individual without multiple myeloma or from a normally proliferating cell line as a negative control.

In another aspect, provided herein are kits for determining whether an individual diagnosed with multiple myeloma that is in remission will relapse, the kit comprising one or more of: (a) one or more oligonucleotides sufficiently complementary to a human mitochondrial chimeric RNA molecule comprising (i) an antisense 16S mitochondrial ribosomal RNA covalently linked at its 5' end to the 3' end of a polynucleotide with an inverted repeat sequence or (ii) a sense 16S mitochondrial ribosomal RNA covalently linked at its 5' end to the 3' end of a polynucleotide with an inverted repeat sequence, wherein the oligonucleotides are able to hybridize with the mitochondrial chimeric RNA molecules to form a stable duplex; (b) a conjugated antibody reagent for label detection; (c) hybridization and wash buffer; (d) one or more slides of fixed plasmocytes (i) isolated from an individual diagnosed with multiple myeloma that has relapsed or isolated from a multiple myeloma cell line exhibiting nuclear or cytoplasmic and nuclear subcellular localization of a sense non-coding mitochondrial RNA (SncmtRNA) as a positive control and (ii) isolated from an individual without relapsed multiple myeloma or isolated from a multiple myeloma cell line exhibiting cytoplasmic subcellular localization of a SncmtRNA as a negative control.

DETAILED DESCRIPTION OF THE INVENTION

Figure 1:
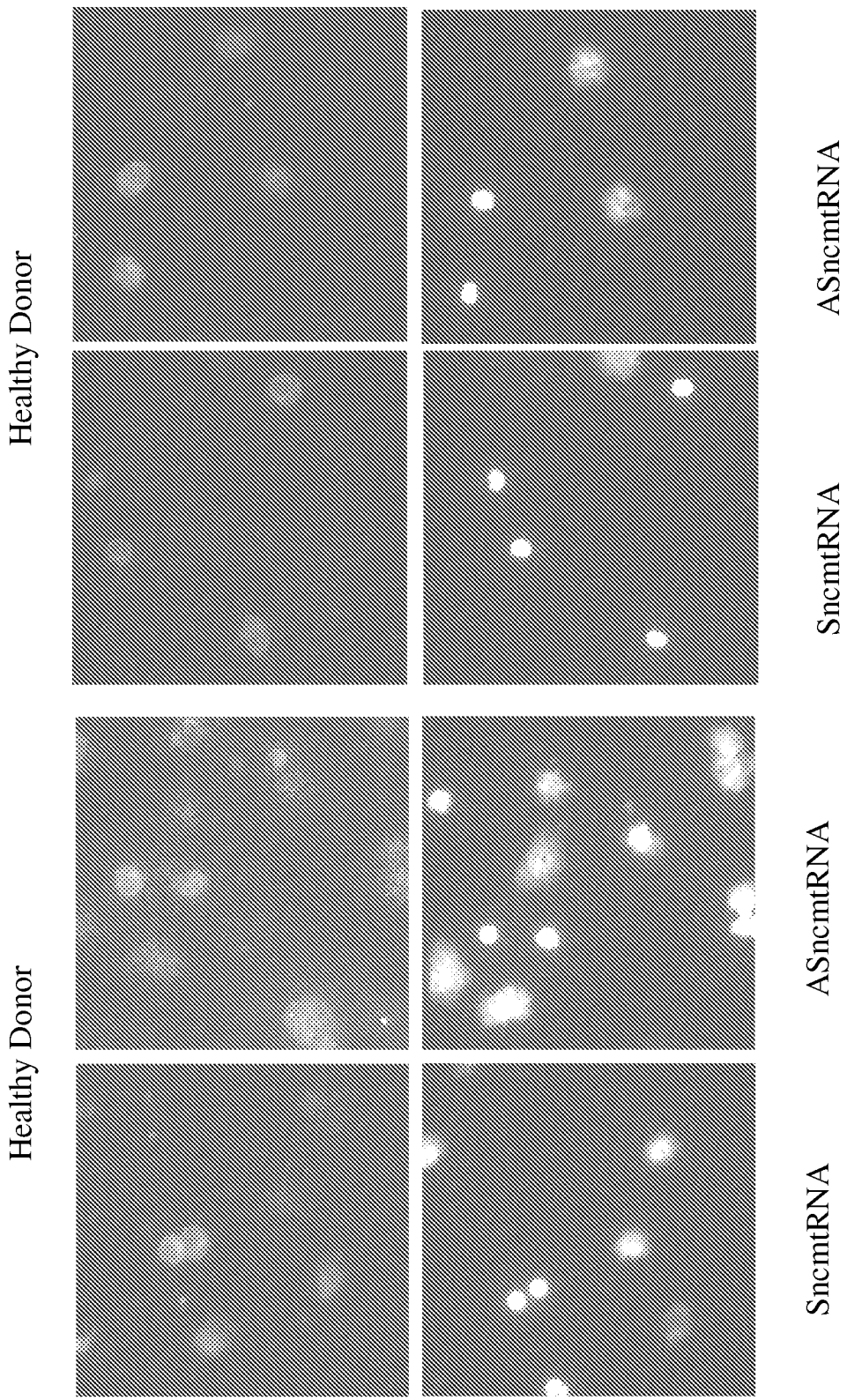
FIG. 1 depicts hybridization signal to both SncmtRNA and ASncmtRNA probes in plasmocytes isolated from the bone marrow of healthy donors (upper panels). The lower panels show the same cells stained with DAPI (nuclear staining).

This invention provides, inter alia, methods for diagnosing and treating individuals with or thought to have multiple myeloma. The inventors have observed that the subcellular localization and expression of particular species of non-coding mitochondrial RNAs (ncmtRNAs) in plasmocytes isolated from the bone marrow of individuals diagnosed with or thought to have multiple myeloma is associated with both the existence of the disease state itself and is indicative of whether an individual who is currently in remission for multiple myeloma will suffer a relapse or is currently suffering a relapse. Assessing individuals for the expression and subcellular localization of these ncmtRNAs is thus useful for selecting individuals or subpopulations of individuals for appropriate treatment and for determining the likelihood of relapse once an individual is in remission following successful initial therapy. This assessment is also useful as a component of a method for treating individuals diagnosed with or suspected of having multiple myeloma.

I. General Techniques

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); PCR: The Polymerase Chain Reaction, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual*, Cold Spring Harbor Laboratory Press, Cold Spring Harbor, N.Y. (jointly referred to herein as "Harlow and Lane"), Beaucage et al. eds., *Current Protocols in Nucleic Acid Chemistry* John Wiley & Sons, Inc., New York, 2000), *Handbook of Experimental Immunology*, 4th edition (D. M. Weir & C. C. Blackwell, eds., Blackwell Science Inc., 1987); and *Gene Transfer Vectors for Mammalian Cells* (J. M. Miller & M. P. Calos, eds., 1987). Other useful references include Harrison's *Principles of Internal Medicine* (McGraw Hill; J. Isseleacher et al., eds.), Dubois' Lupus Erythematosus (5th ed.; D. J. Wallace and B. H. Hahn, eds.

II. Definitions

As used herein, the singular form "a", "an", and "the" includes plural references unless indicated otherwise.

It is understood that aspects and embodiments of the invention described herein include "comprising," "consisting," and "consisting essentially of" aspects and embodiments.

An "individual" can be a vertebrate, a mammal, or a human. Mammals include, but are not limited to, farm animals, sport animals, pets, primates, mice and rats. Individuals also include companion animals including, but not limited to, dogs and cats. In one aspect, an individual is a human.

A "healthcare professional," as used herein, can include, without limitation, doctors, nurses, physician assistants, lab technicians, research scientists, clerical workers employed by the same, or any person involved in determining, diagnosing, aiding in the diagnosis or influencing the course of treatment for the individual.

An "effective amount" or "therapeutically effective amount" refers to an amount of therapeutic compound, such as an oligonucleotide or other anticancer therapy, administered to an individual, either as a single dose or as part of a series of doses, which is effective to produce a desired therapeutic effect.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

III. Methods for Using ncmtRNAs as a Biomarker for Diagnosis of Multiple Myeloma The expression level and subcellular localization of non-coding mitochondrial RNAs (ncmtRNAs) in plasmocytes isolated from bone marrow can be used to determine whether an individual is suffering from multiple myeloma, whether an individual who is in remission for multiple myeloma following successful treatment with one or more anticancer therapies is likely to suffer a relapse, and/or whether an individual is currently suffering a relapse of multiple myeloma. Any of the methods described herein can be used by health care professionals to aid in a treatment plan or to make treatment decisions by choosing among the most appropriate treatment options for multiple myeloma for any individual, based on expression levels and subcellular localization of ncmtRNAs in plasmocytes isolated from the bone marrow of the individual. Similarly, any of the methods described herein can be used for aiding in the diagnosis of an individual or subpopulation of individuals who will benefit from an anticancer (such as an anti-multiple myeloma) therapy.

A. Human Chimeric Non-coding Mitochondrial RNAs (ncmtRNAs)

Human cells express a number of unique chimeric mitochondrial RNA molecules. These molecules are non-coding (i.e., they are not known to serve as a template for the translation of a protein) and comprise the transcribed 16S mitochondrial ribosomal RNA gene covalently linked at the 5' end to an inverted repeat sequence of the 16S mitochondrial ribosomal RNA gene. Chimeric mitochondrial RNA molecules are found in two forms: sense and antisense.

The sense chimeric non-coding mitochondrial RNA (SncmtRNA) molecule corresponds to the 16S mitochondrial ribosomal RNA gene transcribed from the "H-strand" of the circular mitochondrial genome. Covalently linked to the 5' end of this RNA molecule is a nucleotide sequence corresponding to the inverted repeat sequence of the 16S mitochondrial ribosomal RNA gene, transcribed from the "L-strand" of the mitochondrial genome. The size of the inverted repeat sequence in the SncmtRNA can vary from about 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, or 800 nucleotides or more to between about 100-200, 150-250, 200-300, 250-350, 400-500, 450-550, 500-600, 550-650, 600-700, 650-750, or 700-800 nucleotides or more, including any number in between these values. In one embodiment, the inverted repeat sequence in the SncmtRNA corresponds to a fragment of 815 nucleotides of the RNA transcribed from the L-strand of the 16S gene of the mitochondrial genome. In another embodiment, the inverted repeat sequence in the SncmtRNA corresponds to a fragment of 754 nucleotides of the RNA transcribed from the L-strand of the 16S gene of the mitochondrial genome. In still another embodiment, the inverted repeat sequence in the SncmtRNA corresponds to a fragment of 694 nucleotides of the RNA transcribed from the L-strand of the 16S gene of the mitochondrial genome. In another embodiment, the SncmtRNA corresponds to SEQ ID NO:1, SEQ ID NO:2, or SEQ ID NO:3.

The antisense chimeric non-coding mitochondrial RNA (ASncmtRNA) molecule corresponds to the 16S mitochondrial ribosomal RNA gene transcribed from the "L-strand" of the circular mitochondrial genome. Covalently linked to the 5' end of this RNA molecule is a nucleotide sequence corresponding to the inverted repeat sequence of the 16S mitochondrial ribosomal RNA gene, transcribed from the "H-strand" of the mitochondrial genome. The size of the inverted repeat sequence in the ASncmtRNA can vary from about 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800 nucleotides or more to between about 100-200, 150-250, 200-300, 250-350, 400-500, 450-550, 500-600, 550-650, 600-700, 650-750, or 700-800 or more, including any number in between these values. In another embodiment, the SncmtRNA corresponds to SEQ ID NO:4, SEQ ID NO:5, or SEQ ID NO:6.

Further information related to chimeric mitochondrial RNA molecules can be found in U.S. Pat. No. 8,318,686, the disclosure of which is incorporated by reference herein in its entirety.

B. Detection of ncmtRNAs

The SncmtRNA or ASncmtRNA molecules disclosed herein can be used as biomarkers for the diagnosis of multiple myeloma, to determine the likelihood that an individual diagnosed with multiple myeloma will relapse, and/or to determine whether an individual diagnosed with multiple myeloma has relapsed following anticancer therapy by assessing the expression levels and subcellular localization of the ncmtRNA molecules in plasmocytes isolated from bone marrow.

The assessment of SncmtRNA or ASncmtRNA expression is at the level of the transcribed RNA. Assessment of RNA expression levels of gene transcripts is routine and well known in the art. For example, one flexible and sensitive quantitative method for assessing RNA expression levels derived from a biological sample (such as bone marrow or plasmocytes isolated from bone marrow) is by quantitative RT-PCR (qRT-PCR) or by any other comparable quantitative PCR-based method. Additional methods for assessing RNA expression include, but are not limited to, Northern blotting, microarrays, in situ hybridization, serial analysis of gene expression (SAGE), dot blot, oligonucleotide arrays for chimeric RNA and antisense chimeric RNAs, amplification of the RNA by in vitro transcription mediated amplification (TMA), or ribonuclease protection assays.

In one embodiment, expression and subcellular localization of SncmtRNA or ASncmtRNA expression is determined by fluorescent in situ hybridization (FISH). Bone marrow samples for FISH analysis can be obtained by any method known in the art. Once obtained, the bone marrow sample may be fixed, paraffin embedded, fresh, or frozen before expression levels and subcellular localization of ncmtRNAs are measured. In situ hybridization can be performed according to well-known methods in the art. For example, a hybridization solution comprising one or more labeled probes targeted to one or more of the sequences of SncmtRNA (for example, SEQ ID NO 1, SEQ ID NO 2, or SEQ ID NO 3) or ASncmtRNA (for example, SEQ ID NO 4, SEQ ID NO 5, or SEQ ID NO 6) within the plasmocyte is contacted with the cell under hybridization conditions. The hybridization signal is then compared with a predetermined hybridization pattern from normal or control plasmocytes isolated from healthy volunteers or individuals with multiple myeloma, respectively. Labeled probes for performing FISH can be RNA, DNA or synthetic nucleic acids and can be prepared by any method known in the art. Synthetic nucleic acids include riboprobes transcribed in vitro or PCR fragments. In one embodiment, synthetic complementary oligonucleotides can be used. In addition, the synthetic nucleic acid-based probes can have one or more alterations to the oligonucleotide phosphate backbone, sugar moieties, and/or nucleobase (such as any of those described herein) that increase resistance to degradation, such as by nuclease cleavage. The complementary oligonucleotide probes are at least about 10 (such as any of about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) nucleotides in length. In another embodiment, the oligonucleotide probes can be between about 10-15, 15-20, 20-25, 25-30, 30-35, 35-40, 40-45, or 45-50 oligonucleotides in length. In other embodiments, longer oligonucleotide probes can be used, such as 60, 70, 80, 90, or 100 nucleotides in length or more. In some embodiments, the probe is at least 90% (such as at least 91%, 92%, 93%, 94%, 95%, 96%, 97%, 98%, 99%, or 100% identical to the sequences listed in SEQ ID NO:1, SEQ ID NO: 2, SEQ ID NO: 3, SEQ ID NO: 4, SEQ ID NO: 5 and/or SEQ ID NO: 6.

Oligonucleotide probes for use in in situ hybridization are labeled to detect the hybridization with SncmtRNA and/or ASncmtRNA. The probes can be labeled with a detectable marker by any method known in the art. Methods for labeling probes include random priming, end labeling, PCR, and nick translation. Enzymatic labeling is conducted in the presence of nucleic acid polymerase, three unlabeled nucleotides, and a fourth nucleotide which is either directly labeled, contains a linker arm for attaching a label, or is attached to a hapten or other molecule to which a labeled binding molecule (such as a secondary antibody) may bind. Suitable direct labels include radioactive labels such as $^{32}$P, $^{33}$P, $^{3}$H, and $^{35}$S and non-radioactive labels such as fluorescent markers. Fluorescent labels for use in FISH include 5(6)-carboxyfluorescein, 6-((7-amino-4-methylcoumarin.-3-acetyl)amino)hexanoic acid, 5(and 6)-carboxy-X-rhodamine, Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.) or the Alexa dyes comprising Alexa 488, Alexa 532, Alexa 556, Alexa 590, etc. (Molecular Probes, Eugene, Oreg.).

C. Methods for Diagnosing Multiple Myeloma

Provided herein are methods for diagnosing multiple myeloma based on the expression levels and subcellular localization of SncmtRNA and/or ASncmtRNA in plasmocytes isolated from the bone marrow of individuals having or suspected of having multiple myeloma. The expression of SncmtRNA and ASncmtRNA in plasmocytes isolated from the bone marrow of an individual suspected of having multiple myeloma indicates that the plasmocytes are normally proliferating. Further, if the bone marrow sample contains non-proliferating plasmocytes, assessment of ncmtRNA expression will show that neither SncmtRNA nor ASncmtRNA are expressed. However, if measurement of ncmtRNA levels shows expression of SncmtRNA and down regulation or the absence of the ASncmtRNA transcript, the individual has multiple myeloma.

Accordingly, in one aspect, provided herein are methods for diagnosing multiple myeloma in an individual comprising: measuring the expression of a sense non-coding mitochondrial RNA (SncmtRNA) and an antisense non-coding mitochondrial RNA (ASncmtRNA) in plasmocytes isolated from the bone barrow of the individual, wherein the expression of both a SncmtRNA and an ASncmtRNA indicates that the individual does not have multiple myeloma and wherein the expression of a SncmtRNA and the lack of expression of an ASncmtRNA indicates that the individual has multiple myeloma. The expression of the ncmtRNAs can be assessed using any technique known in the art (such as, but not limited to, RT-PCR or another non-quantitative, semi-quantitative, or quantitative PCR-based method, Northern Blot, in situ hybridization (such as, fluorescence in situ hybridization (FISH), or SAGE).

The ASncmtRNA can be a human mitochondrial chimeric RNA molecule comprising an antisense 16S mitochondrial ribosomal RNA covalently linked at its 5' end to the 3' end of a polynucleotide with an inverted repeat sequence. In some embodiments, the ASncmtRNA comprises one or more nucleotide sequences selected from the group consisting of SEQ ID NO:4, SEQ ID NO:5, and SEQ ID NO:6. The SncmtRNA can be a sense 16S mitochondrial ribosomal RNA covalently linked at its 5' end to the 3' end of a polynucleotide with an inverted repeat sequence. In some embodiments, the SncmtRNA comprises one or more nucleotide sequences selected from the group consisting of SEQ ID NO:1, SEQ ID NO:2, and SEQ ID NO:3.

D. Methods for Determining Whether an Individual Diagnosed with Multiple Myeloma Will Relapse The natural progression of multiple myeloma is of relapse following treatment. While new "maintenance" therapies have been effective in extending the duration of remission following initial treatment (e.g., lenalidomide (Revlimid) maintenance therapy), none have been effective in preventing it entirely. Depending on the individual's condition, prior treatment modalities used and the duration of remission, options for relapsed disease include re-treatment with the original therapeutic agent, use of other agents (such as melphalan, cyclophosphamide, thalidomide or dexamethasone, or the proteosome inhibitor bortezomib (Velcade®), careilzomib (Kyprolis®), pomalidomide (Pomalyst®), or additional autologous stem cell transplantation. Thus, the ability to predict or determine the likelihood that an individual diagnosed with multiple myeloma that is currently in remission following initial treatment will relapse would be of great value for assisting health care practitioners in the monitoring and treatment of the disease.

The expression levels and subcellular localization of SncmtRNA and ASncmtRNA in plasmocytes isolated from the bone marrow of individuals diagnosed with multiple myeloma can be used to determine whether the individual is in remission or is likely to relapse or has suffered a relapse. As described herein, if measurement of ncmtRNA levels shows expression of SncmtRNA and down regulation or the absence of the ASncmtRNA transcript, the individual has multiple myeloma. Further, the subcellular localization of the SncmtRNA within the plasmocyte is indicative of whether the individual will suffer a relapse or has already suffered relapse. If the SncmtRNA transcript is localized to the nucleus of the plasmocyte or is predominantly nuclear in subcellular localization or is localized to both the nucleus and cytoplasm of the plasmocyte, the individual will suffer relapse or is currently in relapse. However, solely cytoplasmic subcellular localization of the SncmtRNA transcript indicates that the individual is in remission.

Accordingly, provided herein are methods for determining whether an individual diagnosed with multiple myeloma that is in remission will relapse, the method comprising: measuring the subcellular localization of a sense non-coding mitochondrial RNA (SncmtRNA) in plasmocytes isolated from the bone barrow of the individual, wherein cytoplasmic localization of the SncmtRNA indicates that the individual is in remission and nuclear or cytoplasmic and nuclear localization of the SncmtRNA indicates that the individual will relapse. The expression and/or subcellular localization of the ncmtRNAs can be assessed using any technique known in the art (such as, but not limited to, RT-PCR or another non-quantitative, semi-quantitative, or quantitative PCR-based method, Northern Blot, in situ hybridization (such as, fluorescence in situ hybridization (FISH), or SAGE).

The ASncmtRNA can be a human mitochondrial chimeric RNA molecule comprising an antisense 16S mitochondrial ribosomal RNA covalently linked at its 5' end to the 3' end of a polynucleotide with an inverted repeat sequence. In some embodiments, the ASncmtRNA comprises one or more nucleotide sequences selected from the group consisting of SEQ ID NO:4, SEQ ID NO:5, and SEQ ID NO:6. The SncmtRNA can be a sense 16S mitochondrial ribosomal RNA covalently linked at its 5' end to the 3' end of a polynucleotide with an inverted repeat sequence. In some embodiments, the SncmtRNA comprises one or more nucleotide sequences selected from the group consisting of SEQ ID NO:1, SEQ ID NO:2, and SEQ ID NO:3.

E. Methods for Assessing a Likelihood of a Beneficial Response to an Anti-multiple Myeloma Therapy The expression levels and subcellular localization of SncmtRNA and ASncmtRNA in plasmocytes isolated from the bone marrow of individuals diagnosed with multiple myeloma can be used to determine the likelihood that the individual will respond to an anti-multiple myeloma therapy (such as any of the therapies or treatments for multiple myeloma disclosed herein). As previously described herein, if measurement of ncmtRNA levels shows expression of SncmtRNA and down regulation or the absence of the ASncmtRNA transcript, the individual has multiple myeloma. Further, the subcellular localization of the SncmtRNA within the plasmocyte is indicative of whether the individual will respond to an anti-multiple myeloma therapy. If the SncmtRNA transcript is localized solely to the cytoplasm of the plasmocyte, the individual will likely exhibit a beneficial response to an anti-multiple myeloma therapy. Thus, cytoplasmic localization of the SncmtRNA transcript in the plasmocyte isolated from the bone marrow of individuals diagnosed with multiple myeloma is indicative of a good prognosis with respect to responding to one or more anticancer therapeutics (such as any of those described herein).

Accordingly, provided herein are methods for assessing a likelihood of a beneficial response to an anti-multiple myeloma therapy in an individual suspected of having or developing multiple myeloma, the method comprising: measuring the subcellular localization of a sense non-coding mitochondrial RNA (SncmtRNA) in plasmocytes isolated from the bone barrow of the individual, wherein the cytoplasmic subcellular localization of the SncmtRNA indicates a beneficial response to the anti-multiple myeloma therapy. The expression and/or subcellular localization of the ncmtRNAs can be assessed using any technique known in the art (such as, but not limited to, RT-PCR or another non-quantitative, semi-quantitative, or quantitative PCR-based method, Northern Blot, in situ hybridization (such as, fluorescence in situ hybridization (FISH), or SAGE).

The ASncmtRNA can be a human mitochondrial chimeric RNA molecule comprising an antisense 16S mitochondrial ribosomal RNA covalently linked at its 5' end to the 3' end of a polynucleotide with an inverted repeat sequence. In some embodiments, the ASncmtRNA comprises one or more nucleotide sequences selected from the group consisting of SEQ ID NO:4, SEQ ID NO:5, and SEQ ID NO:6. The SncmtRNA can be a sense 16S mitochondrial ribosomal RNA covalently linked at its 5' end to the 3' end of a polynucleotide with an inverted repeat sequence. In some embodiments, the SncmtRNA comprises one or more nucleotide sequences selected from the group consisting of SEQ ID NO:1, SEQ ID NO:2, and SEQ ID NO:3.

F. Fixed or Data-storage Media

The diagnosis of multiple myeloma, the determination that an individual diagnosed with multiple myeloma will relapse, or the assessment of the likelihood of a beneficial response to an anticancer therapy in an individual suspected of having or developing multiple myeloma may be provided to a healthcare professional by being recorded on a fixed or data storage medium and/or being accessible via a system for reading the storage medium. For example, a system for reading a data storage medium may include a computer including a central processing unit ("CPU"), a working memory which may be, e.g., RAM (random access memory) or "core" memory, mass storage memory (such as one or more disk drives or CD-ROM drives), one or more display devices (e.g., cathode-ray tube ("CRT") displays, light emitting diode ("LED") displays, liquid crystal displays ("LCDs"), electroluminescent displays, vacuum fluorescent displays, field emission displays ("FEDs"), plasma displays, projection panels, etc.), one or more user input devices (e.g., keyboards, microphones, mice, touch screens, etc.), one or more input lines, and one or more output lines, all of which are interconnected by a conventional bidirectional system bus. The system may be a stand-alone computer, or may be networked (e.g., through local area networks, wide area networks, intranets, extranets, or the internet) to other systems (e.g., computers, hosts, servers, etc.). The system may also include additional computer controlled devices such as consumer electronics and appliances.

Input hardware may be coupled to the computer by input lines and may be implemented in a variety of ways. Machine-readable data of this invention may be inputted via the use of a modem or modems connected by a telephone line or dedicated data line. Alternatively or additionally, the input hardware may include CD-ROM drives or disk drives. In conjunction with a display terminal, a keyboard may also be used as an input device.

Output hardware may be coupled to the computer by output lines and may similarly be implemented by conventional devices. By way of example, the output hardware may include a display device for displaying a graphical representation of an active site of this invention using a program such as QUANTA. Output hardware might also include a printer, so that hard copy output may be produced, or a disk drive, to store system output for later use.

Machine-readable storage devices useful in the present invention include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

A person having skill in the art will appreciate that any other method or technique to communicate or store data is may also be contemplated for communication of the diagnosis of multiple myeloma, the determination that an individual diagnosed with multiple myeloma will relapse, or the assessment of the likelihood of a beneficial response to an anticancer therapy in an individual suspected of having or developing multiple myeloma to a healthcare professional.

IV. Methods for Treating Multiple Myeloma

The methods disclosed herein for using the expression and subcellular localization of ncmtRNAs for diagnosing multiple myeloma as well as for identifying individuals who are likely to suffer a relapse of multiple myeloma or who have relapsed can additionally be used in conjunction with methods for the treatment and/or prevention of a multiple myeloma.

The present invention is accordingly directed to methods for inhibiting the symptoms or conditions (disabilities, impairments) associated with multiple myeloma as described in detail below. As such, it is not required that all effects of the condition be entirely prevented or reversed, although the effects of the presently disclosed methods likely extend to a significant therapeutic benefit for the patient. As such, a therapeutic benefit is not necessarily a complete prevention or cure for the condition, but rather, can encompass a result which includes reducing or preventing the symptoms that result from multiple myeloma, reducing or preventing the occurrence of such symptoms (either quantitatively or qualitatively), reducing the severity of such symptoms or physiological effects thereof, and/or enhancing the recovery of the individual after experiencing multiple myeloma symptoms.

Specifically, the therapies of the present invention, when administered to an individual, can treat or prevent one or more of the symptoms or conditions associated with multiple myeloma and/or reduce or alleviate symptoms of or conditions associated with this disorder. As such, protecting an individual from the effects or symptoms resulting from multiple myeloma includes both preventing or reducing the occurrence and/or severity of the effects of the disorder and treating a patient in which the effects of the disorder are already occurring or beginning to occur. A beneficial effect can easily be assessed by one of ordinary skill in the art and/or by a trained clinician who is treating the patient. Preferably, there is a positive or beneficial difference in the severity or occurrence of at least one clinical or biological score, value, or measure used to evaluate such patients in those who have been treated with the methods of the present invention as compared to those that have not.

The methods can be practiced in an adjuvant setting. "Adjuvant setting" refers to a clinical setting in which an individual has had a history of multiple myeloma, and generally (but not necessarily) been responsive to therapy, which includes, but is not limited to, surgery (such as surgical resection), radiotherapy, and chemotherapy. However, because of their history of the proliferative disease (such as multiple myeloma), these individuals are considered at risk of development of the disease. Treatment or administration in the "adjuvant setting" refers to a subsequent mode of treatment. The degree of risk (i.e., when an individual in the adjuvant setting is considered as "high risk" or "low risk") depends upon several factors, most usually the extent of disease when first treated.

The methods provided herein can also be practiced in a "neoadjuvant setting," i.e., the method can be carried out before the primary/definitive therapy. In some embodiments, the individual has previously been treated. In some embodiments, the individual has not previously been treated. In some embodiments, the treatment is a first line therapy.

A. Anticancer Therapies

Provided herein are methods for treating individuals who have been diagnosed with multiple myeloma according to any of the diagnostic methods disclosed herein. Additionally, the invention also provides methods for preventing relapse of multiple myeloma or for treating an individual who has suffered a relapse as determined by the expression and/or subcellular localization of ncmtRNAs within plasmocytes isolated from the bone marrow of individuals diagnosed with or thought to have multiple myeloma according to any of the methods disclosed herein.

1. Oligonucleotides Complementary to ncmtRNAs

In some aspects, the anticancer therapy for use in any of the methods described herein is administration of oligonucleotides complementary to a sense or antisense chimeric non-coding mitochondrial RNA (ncmtRNA) molecule, such as any of these disclosed herein, to individuals diagnosed with multiple myeloma according to any method disclosed herein, for preventing relapse of multiple myeloma, or for treating an individual who has relapsed as determined by any of the methods disclosed herein.

The oligonucleotides for use in any of the methods described herein can be complementary to the SncmtRNA and/or to the ASncmtRNA molecules disclosed herein. Without being bound to theory, it is believed that the complementary oligonucleotides bind to the ncmtRNAs and interfere with their cellular functions. As used herein, an oligonucleotide sequence is "complementary" to a portion of an ncmtRNA, as referred to herein, if the oligonucleotide possesses a sequence having sufficient complementarity to be able to hybridize with the ncmtRNA to form a stable duplex. The ability to hybridize will depend on both the degree of complementarity and the length of the oligonucleotide. Generally, the longer the hybridizing oligonucleotide, the more base mismatches with an ncmtRNA it may contain and still form a stable duplex. In some aspects, the oligonucleotides used as an anticancer therapy according to the methods disclosed herein are at least 8 (such as at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more) base pairs in length. Those skilled in the art can ascertain a tolerable degree of mismatch by use of standard procedures to determine the melting point of the hybridized complex. In some embodiments, the oligonucleotides are at least 85% (such as at least 86%, 87%, 88%, 89%, 90%, 91%, 92%, 93%, 94%, 95%, 96%, 97%, 98%, 99%, or 100%) complementary to the SncmtRNA and/or to the ASncmtRNA molecule. In some embodiments, the complementary oligonucleotide is an antisense oligonucleotide. In one embodiment, the oligonucleotides are complementary to the ncmtRNAs encoded by one or more of SEQ ID NO:1, SEQ ID NO:2, SEQ ID NO:3, SEQ ID NO:4, SEQ ID NO:5, or SEQ ID NO:6. In another embodiments, the oligonucleotides comprise one or more of SEQ ID NOs:7-196.

a. Oligonucleotide Modifications

The naturally occurring internucleoside linkage of RNA and DNA is a 3' to 5 phosphodiester linkage. The oligonucleotides (for example, an antisense oligonucleotides) used for treating multiple myeloma according to any of the methods disclosed herein can have one or more modified, i.e. non-naturally occurring, internucleoside linkages. With respect to therapeutics, modified internucleoside linkages are often selected over oligonucleotides having naturally occurring internucleoside linkages because of desirable properties such as, for example, enhanced cellular uptake, enhanced affinity for target nucleic acids, and increased stability in the presence of nucleases.

Oligonucleotides (such as an antisense oligonucleotide) having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In one embodiment, oligonucleotides (such as antisense oligonucleotides) targeted to the SncmtRNA and/or to the ASncmtRNA molecules disclosed herein comprise one or more modified internucleoside linkages. In some embodiments, the modified internucleoside linkages are phosphorothioate linkages. In other embodiments, each internucleoside linkage of an oligonucleotide compound is a phosphorothioate internucleoside linkage.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific though nonlimiting examples of oligonucleotides (such as antisense oligonucleotides) useful in the methods of the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

In some embodiments, modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thiono-phosphoramidates, thionoalkylphosphonates, thionoalkylphospho-triesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof) can also be employed. Various salts, mixed salts and free acid forms are also included. Oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other embodiments, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Representative United States patents that teach the preparation of the above phosphorus-containing and non-phosphorus-containing linkages include, but are not limited to, U.S. Pat. Nos. 5,541,306; 5,550,111; 5,563,253; 5,571,799; 5,587,361; 5,194,599; 5,565,555; 5,527,899; 5,721,218; 5,672,697 and 5,625,050, 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Modified oligonucleotides (such as antisense oligonucleotides) complementary to SncmtRNA and/or ASncmtRNA used as anticancer therapies in conjunction with any of the methods disclosed herein may also contain one or more substituted sugar moieties. For example, the furanosyl sugar ring can be modified in a number of ways including substitution with a substituent group, bridging to form a bicyclic nucleic acid "BNA" and substitution of the 4'-O with a heteroatom such as S or N(R) as described in U.S. Pat. No. 7,399,845, hereby incorporated by reference herein in its entirety. Other examples of BNAs are described in published International Patent Application No. WO 2007/146511, hereby incorporated by reference herein in its entirety.

The oligonucleotides (such as antisense oligonucleotides) for use in the methods for treating multiple myeloma as disclosed herein can optionally contain one or more nucleotides having modified sugar moieties. Sugar modifications may impart nuclease stability, binding affinity or some other beneficial biological property to the antisense compounds. The furanosyl sugar ring of a nucleoside can be modified in a number of ways including, but not limited to: addition of a substituent group, particularly at the 2' position; bridging of two non-geminal ring atoms to form a bicyclic nucleic acid (BNA); and substitution of an atom or group such as —S—, —N(R)— or —C(R1)(R2) for the ring oxygen at the 4'-position. Modified sugars include, but are not limited to: substituted sugars, especially 2'-substituted sugars having a 2'-F, 2'-OCH2 (2'-OMe) or a 2'-O $(CH_2)_2$—$OCH_3$ (2'-O-methoxyethyl or 2'-MOE) substituent group; and bicyclic modified sugars (BNAs), having a 4'-$(CH_2)$n-O-2' bridge, where n=1 or n=2. Methods for the preparations of modified sugars are well known to those skilled in the art.

In certain embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In other embodiments, the bicyclic sugar moiety comprises a bridge group between the 2' and the 4'-carbon atoms. In certain such embodiments, the bridge group comprises from 1 to linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N(R1)-, —C(R1)(R2)-, —C(R1)=C(R1)-, —C(R1)=N—, —C(=NR1)-, —Si(R1)(R2)-, —S(=O)2-, —S(O)—, —C(=O)— and —C(=S)—; where each R1 and R2 is, independently, H, hydroxyl, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, a heterocycle radical, a substituted hetero-cycle radical, heteroaryl, substituted heteroaryl, C5-C7 alicyclic radical, substituted C5-C7 alicyclic radical, halogen, substituted oxy (—O—), amino, substituted amino, azido, carboxyl, substituted carboxyl, acyl, substituted acyl, CN, thiol, substituted thiol, sulfonyl (S(=O)2-H), substituted sulfonyl, sulfoxyl (S(=O)—H) or substituted sulfoxyl; and each substituent group is, independently, halogen, C1-C12 alkyl, substituted C1-C12 alkyl, C2-C12 alkenyl, substituted C2-C12 alkenyl, C2-C12 alkynyl, substituted C2-C12 alkynyl, amino, substituted amino, acyl, substituted acyl, C1-C12 amino alkyl, C1-C12 aminoalkoxy, substituted C1-C12 aminoalkyl, substituted C1-C12 aminoalkoxy or a protecting group.

Oligonucleotides (such as antisense oligonucleotides) for use in any of the methods disclosed herein may also include nucleobase (often referred to in the art simply as "base") modifications or substitutions. Nucleobase modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to oligonucleotide compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an oligonucleotide compound (such as an antisense oligonucleotide compound) for a target nucleic acid (such as an ncmtRNA).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

As used herein, "unmodified" or "natural" nucleobases include the purine bases adenine (A) and guanine (G), and the pyrimidine bases thymine (T), cytosine (C) and uracil (U).

Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), O-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B. ed., CRC Press, 1993.

Representative United States patents that teach the preparation of certain of the above noted modified nucleobases as well as other modified nucleobases include, but are not limited to, U.S. Pat. Nos. 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, each of which is herein incorporated by reference.

b. Ribozymes

In another embodiment of the invention, ribozymes can be used to interfere with the ncmtRNA molecules described herein to induce cell death in proliferative cells associated with multiple myeloma. The sequence of the ribozyme can be designed according to the sequence of the ASncmtRNA (for example, SEQ ID NO 4, SEQ ID NO 5, SEQ ID NO 6) or the SncmtRNA (for example, SEQ ID NO 1, SEQ ID NO 2, SEQ ID NO 3) to cleave specific regions of the transcript. Ribozymes are enzymatic RNA molecules capable of catalyzing the specific cleavage of RNA (Rossi, *Curr. Biology* 4:469-471, 1994). The mechanism of ribozyme action involves sequence specific hybridization of the ribozyme molecule to complementary target RNA, followed by an endonucleolytic cleavage. The composition of ribozyme molecules must include one or more sequences complementary to the RNA, and must include the well-known catalytic sequence responsible for RNA cleavage, and described in U.S. Pat. No. 5,093,246, the disclosure of which is incorporated by reference herein in its entirety. As such, within the scope of the invention hammerhead ribozyme molecules can be engineered that specifically and efficiently catalyze endonucleolytic cleavage of the ASncmtRNA or SncmtRNA molecules disclosed herein. The construction and production of hammerhead ribozymes is well known in the art and it was described (Haseloff et al., Gene, 82:43-52, 1989). Ribozymes of the present invention can also include RNA endoribonucleases (Zaug et al., Science, 224:574-578, 1984).

c. RNA Interference

In another aspect, interference with the function of the ASncmtRNA and/or SncmtRNA molecules disclosed herein for the treatment of multiple myeloma in any of the methods disclosed herein can be achieved by RNA interference or RNA silencing. RNA interference (RNAi) has emerged as a novel and promising approach for gene silencing in mammalian cells (Elbashir et al., Nature 411:494-498, 2001; McManus et al., Nature Rev. Genet. 3:737-747, 2002). Synthetically synthesized double stranded RNA molecules of about 8 to 40 (such as about 10 to 36, 14 to 32, 18-28, or 22-24) base pairs (bp) or at least about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bp in length hybridize specifically to their complementary target RNA, leading to degradation of the RNA. Several different genes have been silenced successfully by small interfering RNA or siRNA (Lu et al., Curr. Opin. Mol. Ther. 5:225-234, 2003; Wacheck et al., Oligonucleotides 13:393-400, 2003). Therefore, synthetic double stranded RNA targeted to the ASncmtRNA and/or SncmtRNA molecules disclosed herein can be used to degrade these transcripts and induce tumor cell death. Those familiar in the art will understand that the sequence of the siRNA has to be complementary to any region of the ASncmtRNA and/or SncmtRNA molecules (such as complementary to any of SEQ ID NO 1, SEQ ID NO 2, SEQ ID NO 3, SEQ ID NO 4, SEQ ID NO 5, and/or SEQ ID NO 6).

d. Gene Therapy

In one embodiment, a recombinant vector can be used for delivering one or more oligonucleotides (such as any of the oligonucleotides disclosed herein) complementary to a sense and/or antisense chimeric non-coding mitochondrial RNA molecule to the individual. This can include both systemic delivery and delivery localized to a particular region of the body (such as, the bone marrow). Any vector capable of enabling recombinant production of one or more oligonucleotides complementary to a sense or antisense chimeric ncmtRNA molecule and/or which can deliver one or more oligonucleotides complementary to a sense or antisense chimeric ncmtRNA molecule into a host cell. The vector can be either RNA or DNA, either prokaryotic or eukaryotic, and typically is a virus or a plasmid. The vector can be part of a DNA vaccine or used as part of any other method for delivering a heterologous gene for expression in a host cell that is known to one having skill in the art. Recombinant vectors are capable of replicating when transformed into a suitable host cell. Viral vectors infect a wide range of non-dividing human cells and have been used extensively in live vaccines without adverse side effects. A viral vector (such as, but not limited to, an adenoviral vector or an adeno-associated viral (AAV) vector (e.g. AAV-1, AAV-2, AAV-3, AAV-4, AAV-5, AAV-6, etc. or hybrid AAV vectors comprising the same) is an example of a vector for use in the present methods for delivering one or more oligonucleotides complementary to a sense or antisense chimeric ncmtRNA molecule to multiple myeloma cancer cells (such as a plasmocyte; see, e.g. U.S. Patent Application Publication No. 2004/0224389, the disclosure of which is incorporated by reference herein).

2. Other Anticancer Therapies

In some aspects, any of the methods of treatment described herein can comprise administering one or more additional anticancer therapies to the individual. Various classes of anticancer agents can be used. Non-limiting examples include: alkylating agents, antimetabolites, anthracyclines, plant alkaloids, topoisomerase inhibitors, podophyllotoxin, antibodies (e.g., monoclonal or polyclonal), tyrosine kinase inhibitors (e.g., imatinib mesylate (Gleevec® or Glivec®)), hormone treatments, soluble receptors and other antineoplastics.

Topoisomerase inhibitors are also another class of anticancer agents that can be used. Topoisomerases are essential enzymes that maintain the topology of DNA. Inhibition of type I or type II topoisomerases interferes with both transcription and replication of DNA by upsetting proper DNA supercoiling. Some type I topoisomerase inhibitors include camptothecins: irinotecan and topotecan. Examples of type II inhibitors include amsacrine, etoposide, etoposide phosphate, and teniposide. These are semisynthetic derivatives of epipodophyllotoxins, alkaloids naturally occurring in the root of American Mayapple (Podophyllum peltatum).

Antineoplastics include the immunosuppressant dactinomycin, doxorubicin, epirubicin, bleomycin, mechlorethamine, cyclophosphamide, chlorambucil, ifosfamide. The antineoplastic compounds generally work by chemically modifying a cell's DNA.

Alkylating agents can alkylate many nucleophilic functional groups under conditions present in cells. Cisplatin and carboplatin, and oxaliplatin are alkylating agents. They impair cell function by forming covalent bonds with the amino, carboxyl, sulfhydryl, and phosphate groups in biologically important molecules.

Vinca alkaloids bind to specific sites on tubulin, inhibiting the assembly of tubulin into microtubules (M phase of the cell cycle). The vinca alkaloids include: vincristine, vinblastine, vinorelbine, and vindesine.

Anti-metabolites resemble purines (azathioprine, mercaptopurine) or pyrimidine and prevent these substances from becoming incorporated in to DNA during the "S" phase of the cell cycle, stopping normal development and division. Anti-metabolites also affect RNA synthesis.

Plant alkaloids and terpenoids are derived from plants and block cell division by preventing microtubule function. Since microtubules are vital for cell division, without them, cell division cannot occur. The main examples are vinca alkaloids and taxanes.

Podophyllotoxin is a plant-derived compound which has been reported to help with digestion as well as used to produce two other cytostatic drugs, etoposide and teniposide. They prevent the cell from entering the G1 phase (the start of DNA replication) and the replication of DNA (the S phase).

Taxanes as a group includes paclitaxel and docetaxel. Paclitaxel is a natural product, originally known as Taxol and first derived from the bark of the Pacific Yew tree. Docetaxel is a semi-synthetic analogue of paclitaxel. Taxanes enhance stability of microtubules, preventing the separation of chromosomes during anaphase.

In some aspects, the anticancer therapeutics can be selected from remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bortezomib (Velcade®), bisphosphonate, arsenic trioxide, vincristine, doxorubicin (Doxil®), paclitaxel, ganciclovir, adriamycin, estrainustine sodium phosphate (Emcyt®), sulindac, or etoposide.

In other embodiments, the anticancer therapeutics can be selected from bortezomib, cyclophosphamide, dexamethasone, doxorubicin, interferon-alpha, lenalidomide, melphalan, pegylated interferon-alpha, prednisone, thalidomide, or vincristine.

3. Stem Cell Transplantation and Ex Vivo Treatment of Autologous Hematopoietic Stem Cells In other aspects, any of the methods of treatment described herein can include either autologous or allogenic stem cell transplantation therapy. In recent years, high-dose chemotherapy with autologous hematopoietic stem-cell transplantation has become the preferred treatment for multiple myeloma patients under the age of 65. While not curative, this procedure does prolong overall survival and complete remission. Prior to stem-cell transplantation, these patients receive an initial course of induction chemotherapy. The most common induction regimens used today are thalidomide-dexamethasone, bortezomib based regimens, and lenalidomide-dexamethasone (Kyle & Rajkumar, 2008, *Blood.* 111 (6): 2962-72). Autologous peripheral stem cell transplantation is useful for up to 50% of multiple myeloma patients. Despite a low mortality rate, problems with such transplant therapy include the inability to eradicate the tumor and the difficulty in the removal of myeloma cells and their precursors from the stem cell collection used for transplantation. Autologous stem cell transplantation is typically used for individuals under the age of 65 years who do not have substantial heart, lung, renal or liver dysfunction.

Allogenic transplant (the transplantation of a healthy person's stem cells into the affected individual), is another therapy option for treating multiple myeloma, but is less frequently used since the mortality rate at 100 days is 25-30% and it does not provide a cure. Only 5-10% of patients with multiple myeloma are eligible for allogeneic bone marrow transplantation because of their age and the paucity of a human leukocyte antigen (HLA)-matched sibling donor. Use of allogenic transplant for the treatment of relapsed myeloma also remains a treatment strategy with limited clinical benefit. Most studies evaluating its use in this setting demonstrate long-term disease-free survival of 10-20%, with a significant fraction of patients developing relapse.

When included as a treatment for multiple myeloma according to any of the methods disclosed herein, autologous stem cell transplantation can also include the step of treating the hematopoietic stem-cells and/or bone marrow to be transplanted into the affected individual with any of the anticancer therapeutics disclosed herein, prior to transplantation into the affected individual. In one embodiment, hematopoietic stem-cells and/or bone marrow for use in autologous stem cell transplantation can be treated with an effective amount of one or more oligonucleotides (such as antisense oligonucleotides) sufficiently complementary to an ASncmtRNA or SncmtRNA molecule (such as any of the ASncmtRNA and/or SncmtRNA molecules disclosed herein) to form a stable duplex prior to transplantation into the affected individual. In another embodiment, the oligonucleotides are sufficiently complementary to SEQ ID NO:1, SEQ ID NO:2, SEQ ID NO:3, SEQ ID NO:4, SEQ ID NO:5, or SEQ ID NO:6, to form a stable duplex. In other embodiments, the oligonucleotides comprise one or more of SEQ ID Nos:7-196.

It has been shown that autologous transplantation of bone marrow or hematological stem cells can also be used to treat other forms of hematological cancers (such as, but not limited to, leukemia and lymphoma). Accordingly, in some aspects, when included as a treatment for a hematological cancer, provided herein is a method of performing autologous stem cell transplantation which includes the step of treating the hematopoietic stem-cells and/or bone marrow to be transplanted into the affected individual with any of the anticancer therapeutics disclosed herein, prior to transplantation into the affected individual. In one embodiment, hematopoietic stem-cells and/or bone marrow for use in autologous stem cell transplantation in an individual with a hematological cancer can be treated with an effective amount of one or more oligonucleotides (such as antisense oligonucleotides) sufficiently complementary to an ASncmtRNA or SncmtRNA molecule (such as any of the ASncmtRNA and/or SncmtRNA molecules disclosed herein) to form a stable duplex prior to transplantation into the affected individual. In another embodiment, the oligonucleotides are sufficiently complementary to SEQ ID NO:1, SEQ ID NO:2, SEQ ID NO:3, SEQ ID NO:4, SEQ ID NO:5, or SEQ ID NO:6, to form a stable duplex. In other embodiments, the oligonucleotides comprise one or more of SEQ ID Nos:7-196.

4. Pharmaceutical Compositions

Any of the anticancer therapies (such as oligonucleotide-based therapies) disclosed herein can be administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound. When employed as oral compositions, the oligonucleotides and another disclosed herein are protected from acid digestion in the stomach by a pharmaceutically acceptable protectant.

This invention also includes pharmaceutical compositions which contain, as the active ingredient, one or more of the anticancer therapies disclosed herein associated with one or more pharmaceutically acceptable excipients or carriers. In making the compositions of this invention, the active ingredient is usually mixed with an excipient or carrier, diluted by an excipient or carrier or enclosed within such an excipient or carrier which can be in the form of a capsule, sachet, paper or other container. When the excipient or carrier serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active lyophilized compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients or carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 mg to about 100 mg or more, such as any of about 1 mg to about 5 mg, 1 mg to about 10 mg, about 1 mg to about 20 mg, about 1 mg to about 30 mg, about 1 mg to about 40 mg, about 1 mg to about 50 mg, about 1 mg to about 60 mg, about 1 mg to about 70 mg, about 1 mg to about 80 mg, or about 1 mg to about 90 mg, inclusive, including any range in between these values, of the active ingredient. The term "unit dosage forms" refers to physically discrete units suitable as unitary dosages for individuals, each unit containing a predetermined quantity of active material calculated to produce the desired therapeutic effect, in association with a suitable pharmaceutical excipient or carrier.

The anticancer therapies disclosed herein are effective over a wide dosage range and are generally administered in a therapeutically effective amount. It will be understood, however, that the amount of the anticancer therapies actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient anticancer therapy is mixed with a pharmaceutical excipient or carrier to form a solid preformulation composition containing a homogeneous mixture of a compound of the present invention. When referring to these preformulation compositions as homogeneous, it is meant that the active ingredient is dispersed evenly throughout the composition so that the composition can be readily subdivided into equally effective unit dosage forms such as tablets, pills and capsules.

The tablets or pills of the present invention can be coated or otherwise compounded to provide a dosage form affording the advantage of prolonged action and to protect the anticancer therapies (such as an oligonucleotide) from acid hydrolysis in the stomach. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention can be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions can contain suitable pharmaceutically acceptable excipients as described herein. The compositions can be administered by the oral or nasal respiratory route for local or systemic effect. Compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder compositions can also be administered, orally or nasally, from devices which deliver the formulation in an appropriate manner.

B. Methods for Treating Multiple Myeloma

Provided herein are method for treating multiple myeloma in an individual in need thereof comprising: measuring the expression of a sense non-coding mitochondrial RNA (SncmtRNA) and an antisense non-coding mitochondrial RNA (ASncmtRNA) in plasmocytes isolated from the bone barrow of the individual, wherein the expression of both a SncmtRNA and an ASncmtRNA indicates that the individual does not have multiple myeloma and wherein the expression of a SncmtRNA and the lack of expression of an ASncmtRNA indicates that the individual has multiple myeloma; and treating the individual with an effective amount of one or more anticancer therapeutics (such as any of the anticancer therapeutics disclosed herein) if the plasmocytes of the individual express only the SncmtRNA and do not express the ASncmtRNA.

Also provided herein is a method for treating multiple myeloma in an individual in need thereof comprising: treating the individual with an effective amount of one or more anticancer therapeutics, wherein prior to treatment it has been determined that plasmocytes isolated from the bone barrow of the individual express a sense non-coding mitochondrial RNA (SncmtRNA) and do not express an antisense non-coding mitochondrial RNA (ASncmtRNA).

In some embodiments, the anticancer therapeutics comprise one or more oligonucleotides (such as antisense oligonucleotides) sufficiently complementary to a human non-coding mitochondrial chimeric RNA molecule comprising an antisense 16S mitochondrial ribosomal RNA covalently linked at its 5' end to the 3' end of a polynucleotide with an inverted repeat sequence or a sense 16S mitochondrial ribosomal RNA covalently linked at its 5' end to the 3' end of a polynucleotide with an inverted repeat sequence, wherein the oligonucleotides are able to hybridize with the mitochondrial chimeric RNA molecules to form a stable duplex. In some embodiments, the anticancer therapeutic is an RNAi oligonucleotide, an antisense oligonucleotide, or a ribozyme. In yet other embodiments, the oligonucleotide contains one or more modifications to a phosphate backbone linkage, a sugar, or a base, such as any of the modifications disclosed herein.

In another embodiment, the anticancer therapeutics can be selected from bortezomib, cyclophosphamide, dexamethasone, doxorubicin, interferon-alpha, lenalidomide, melphalan, pegylated interferon-alpha, prednisone, thalidomide, or vincristine or any other compound disclosed herein for the treatment of multiple myeloma.

In a further embodiment, the individual is treated with a combination of one or more oligonucleotides (such as antisense oligonucleotides) sufficiently complementary to any of the SncmtRNA and/or ASncmtRNA molecules disclosed herein and an anticancer therapeutic selected from bortezomib, cyclophosphamide, dexamethasone, doxorubicin, interferon-alpha, lenalidomide, melphalan, pegylated interferon-alpha, prednisone, thalidomide, or vincristine or any other compound disclosed herein for the treatment of multiple myeloma. In yet another embodiment, the individual is treated with stem cell transplant therapy, either autologous or allogenic.

As non-limiting examples, treatment according to the present invention may be provided as a daily dosage of a compound of the present invention in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

In another embodiment, the method further comprises administering one or more additional therapies. These additional therapies can include, without limitation, allogenic or autologous stem cell transplant therapy. In embodiments where the additional therapy includes autologous stem cell transplant therapy, the method can further comprise the step of treating hematopoietic stem-cells and/or bone marrow for use in autologous stem cell transplantation with an effective amount of one or more oligonucleotides (such as antisense oligonucleotides) sufficiently complementary to an ASncmtRNA or SncmtRNA molecule (such as any of the ASncmtRNA and/or SncmtRNA molecules disclosed herein) to form a stable duplex prior to transplantation into the affected individual.

C. Methods for Preventing Relapse of Multiple Myeloma

In other aspects, provided herein are methods for preventing relapse of multiple myeloma in an individual who has responded to initial treatment and is in remission. A number of randomized studies have shown a benefit from maintenance therapy with novel agents at least in terms of response rate and progression-free survival (PFS) following initial successful treatment (Harousseau, 2009, Hematol. Rep., 1(2)).

Accordingly, provided herein are methods for preventing relapse of multiple myeloma in an individual in need thereof comprising measuring the subcellular localization of a sense non-coding mitochondrial RNA (SncmtRNA) in plasmocytes isolated from the bone barrow of the individual, wherein the cytoplasmic localization of the SncmtRNA indicates that the individual is in remission; and treating the individual with an effective amount of one or more maintenance anticancer therapeutics if the SncmtRNA is localized to the cytoplasm of the plasmocytes.

Also provided herein are methods for preventing relapse in multiple myeloma in an individual in need thereof comprising: treating the individual with an effective amount of one or more maintenance anticancer therapeutics, wherein prior to treatment it has been determined that plasmocytes isolated from the bone barrow of the individual exhibit subcellular cytoplasmic localization of a sense non-coding mitochondrial RNA (SncmtRNA).

In some embodiments, the maintenance anticancer therapeutics comprise any of the oligonucleotide-based (such as antisense-based) therapies disclosed herein and/or any other therapy for the treatment of multiple myeloma disclosed herein.

In other embodiments, a "maintenance schedule" may be used in which one or more maintenance anticancer therapies are administered less frequency than in the original treatment administered prior to remission, such as once per week or once every two weeks. The maintenance schedule can be continued either for a fixed period of time, generally 1-2 years, or indefinitely as long as the patient is continuing to show no signs of progressive disease and is tolerating the treatment without significant toxicity.

D. Methods for Treating Relapsed Multiple Myeloma

In yet other aspects, provided herein are methods for treating relapsed multiple myeloma in an individual thereof. "Relapsed and/or refractory multiple myeloma" refers to multiple myeloma that has become unresponsive to a drug or a therapy. For example and without limitation, relapsed and/or refractory multiple myeloma includes multiple myeloma in patients whose first progression occurs in the absence of any treatment following successful treatment with a drug or a therapy; multiple myeloma in patients who progress on a treatment, or within 60 days of the treatment; and multiple myeloma in patients who progress while receiving treatment.

Accordingly, in some aspects, provided herein are methods for treating relapsed multiple myeloma in an individual thereof comprising measuring the subcellular localization of a sense non-coding mitochondrial RNA (SncmtRNA) in plasmocytes isolated from the bone barrow of the individual, wherein the (i) nuclear or (ii) cytoplasmic and nuclear localization of the SncmtRNA indicates that the individual has relapsed; and treating the individual with one or more anti-cancer therapeutics if the SncmtRNA is localized to (i) the nuclei or (ii) cytoplasm and nuclei of the plasmocytes.

Also provided herein, in other aspects, are methods for treating relapsed multiple myeloma in an individual thereof comprising treating the individual with one or more anti-cancer therapeutics, wherein prior to treatment it has been determined that plasmocytes isolated from the bone barrow of the individual exhibit (i) nuclear or (ii) cytoplasmic and nuclear subcellular localization of a sense non-coding mitochondrial RNA (SncmtRNA).

In another embodiment, the therapeutically effective amount of said composition is administered as part of a salvage therapy in treating patients wherein the multiple myeloma has become refractory to other drugs for treating multiple myeloma. In some embodiments, the drug for treating multiple myeloma to which the multiple myeloma is refractory, includes, without limitation, bortezomib, cyclophosphamide, dexamethasone, doxorubicin, interferon-alpha, lenalidomide, melphalan, pegylated interferon-alpha, prednisone, thalidomide, and vincristine.

In some embodiments, the anticancer therapeutics for treating relapsed multiple myeloma comprise one or more oligonucleotides (such as antisense oligonucleotides) sufficiently complementary to a human non-coding mitochondrial chimeric RNA molecule comprising an antisense 16S mitochondrial ribosomal RNA covalently linked at its 5' end to the 3' end of a polynucleotide with an inverted repeat sequence or a sense 16S mitochondrial ribosomal RNA covalently linked at its 5' end to the 3' end of a polynucleotide with an inverted repeat sequence, wherein the oligonucleotides are able to hybridize with the mitochondrial chimeric RNA molecules to form a stable duplex. In some embodiments, the anticancer therapeutic is an RNAi oligonucleotide, an antisense oligonucleotide, or a ribozyme. In yet other embodiments, the oligonucleotide contains one or more modifications to a phosphate backbone linkage, a sugar, or a base, such as any of the modifications disclosed herein.

In another embodiment, the anticancer therapeutics can be selected from bortezomib, cyclophosphamide, dexamethasone, doxorubicin, interferon-alpha, lenalidomide, melphalan, pegylated interferon-alpha, prednisone, thalidomide, or vincristine or any other compound disclosed herein for the treatment of multiple myeloma.

In a further embodiment, the individual is treated with a combination of one or more oligonucleotides (such as antisense oligonucleotides) sufficiently complementary to any of the SncmtRNA and/or ASncmtRNA molecules disclosed herein and an anticancer therapeutic selected from bortezomib, cyclophosphamide, dexamethasone, doxorubicin, interferon-alpha, lenalidomide, melphalan, pegylated interferon-alpha, prednisone, thalidomide, or vincristine or any other compound disclosed herein for the treatment of multiple myeloma. In yet another embodiment, the individual is treated with stem cell transplant therapy, either autologous or allogenic.

As non-limiting examples, treatment according to the present invention may be provided as a daily dosage of a compound of the present invention in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

In another embodiment, the method for treating relapsed multiple myeloma further comprises administering one or more additional therapies. These additional therapies can include, without limitation, allogenic or autologous stem cell transplant therapy. In embodiments where the additional therapy includes autologous stem cell transplant therapy, the method can further comprise the step of treating hematopoietic stem-cells and/or bone marrow for use in autologous stem cell transplantation with an effective amount of one or more oligonucleotides (such as antisense oligonucleotides) sufficiently complementary to an ASncmtRNA or SncmtRNA molecule (such as any of the ASncmtRNA and/or SncmtRNA molecules disclosed herein) to form a stable duplex prior to transplantation into the affected individual.

V. Kits

In other aspects, provided herein are kits suitable for performing an assay which detect the expression and subcellular localization of one or more SncmtRNA and/or ASncmtRNA molecules (such as any of those disclosed herein) in plasmocytes isolated from the bone marrow of individuals diagnosed with or thought to have multiple myeloma.

In one embodiment, the kit is for diagnosing multiple myeloma. This kit can comprise one or more of one or more oligonucleotides sufficiently complementary to a human mitochondrial chimeric RNA molecule comprising (i) an antisense 16S mitochondrial ribosomal RNA covalently linked at its 5' end to the 3' end of a polynucleotide with an inverted repeat sequence or (ii) a sense 16S mitochondrial ribosomal RNA covalently linked at its 5' end to the 3' end of a polynucleotide with an inverted repeat sequence, wherein the oligonucleotides are able to hybridize with the mitochondrial chimeric RNA molecules to form a stable duplex, one or more conjugated antibody reagents for label detection, one or more hybridization and/or wash buffers; and/or one or more slides of fixed plasmocytes (i) isolated from an individual diagnosed with multiple myeloma or a multiple myeloma cell line as a positive control and (ii) isolated from an individual without multiple myeloma or from a normally proliferating cell line as a negative control.

In another embodiment, the kit is for determining whether an individual diagnosed with multiple myeloma that is in remission will relapse. This kit can comprise one or more of one or more oligonucleotides sufficiently complementary to a human mitochondrial chimeric RNA molecule comprising (i) an antisense 16S mitochondrial ribosomal RNA covalently linked at its 5' end to the 3' end of a polynucleotide with an inverted repeat sequence or (ii) a sense 16S mitochondrial ribosomal RNA covalently linked at its 5' end to the 3' end of a polynucleotide with an inverted repeat sequence, wherein the oligonucleotides are able to hybridize with the mitochondrial chimeric RNA molecules to form a stable duplex, one or more conjugated antibody reagents for label detection, one or more hybridization and/or wash buffers; and/or one or more slides of fixed plasmocytes (i) isolated from an individual diagnosed with multiple myeloma that has relapsed or isolated from a multiple myeloma cell line exhibiting nuclear or cytoplasmic and nuclear subcellular localization of a sense non-coding mitochondrial RNA (SncmtRNA) as a positive control and (ii) isolated from an individual without relapsed multiple myeloma or isolated from a multiple myeloma cell line exhibiting cytoplasmic subcellular localization of a SncmtRNA as a negative control.

EXAMPLES

Example 1

Determination of Expression and Subcellular Localization of ncmtRNAs in Plasmocytes Isolated from Healthy Individuals In this study, differential expression of antisense non-coding mitochondrial RNA (ASncmtRNA) and sense non-coding mitochondrial RNA (SncmtRNA) was determined in plasmocytes isolated from the bone marrow of healthy volunteers.

Materials and Methods

Isolation of plasmocytes from bone marrow: To obtain plasmocytes, a bone marrow sample of 1-2 ml was obtained from the patient by inserting a needle into the breastbone under local anesthesia. A small sample of bone marrow (1-2 ml) was removed and the mononuclear cells separated by centrifugation in a histopaque gradient. The layer of cells was recovered, washed with PBS (50 mM sodium phosphate, 150 mM NaCl and 2 mM EDTA, pH 9.0) and incubated with magnetic beads (Miltenyi Biotech) loaded with anti-CD 138 antibodies. The plasmocytes (CD138 positive) were purified with a magnetic column and suspended in PBS. Samples containing between 200 to 500 cells in 100-200 µl were cytospinned on positively charged slides.

Fluorescence in situ hybridization (FISH) to detect ncmtRNAs: Isolated plasmocytes fixed on slides were incubated with 100[11 0.2N HCl for 5 min at room temperature. The acid was discarded and the cells washed twice with PBS. The cells were then incubated with 100 IA hybridization buffer (50% formamide, 150 µg/ml herring sperm DNA, 4×SSC, 2 mM EDTA) containing 0.5 1, IM Texas Red Alexa labeled probe P1 (SEQ ID NO 197; 5' GTTCT-TGGGTGGGTGTGGG 3'), complementary to the SncmtRNA. Another slide was hybridized with 0.05 µM each of two 5' Texas Red-labeled probes P2 (SEQ ID NO 198; 5' GATAACAGCGCAATCCTATT 3') and P3 (SEQ ID NO 62; 5' ACCGTGCAAAGGTAGCATAATCA 3'), complementary to the ASncmtRNAs. A third slide was hybridized with the positive hybridization control corresponding to a 5'-Texas Red-labeled probe complementary to 18S rRNA (P4: SEQ ID NO 199; 5' AGTGGACTCATTCCAATTACA 3'). The cells were finally stained with DAPI (1 mg/ml) and analyzed by fluorescence microscopy on an Olympus BX-51 micro scope.

Results

The results of the analysis of plasmocytes from healthy donors (LC and NF) are depicted in FIG. 1. Normal cells are identified by their hybridization signal to both SncmtRNA and ASncmtRNA probes. Additionally, the transcripts for both species of ncmtRNAs display cytoplasmic subcellular localization.

Example 2

Determination of Expression and Subcellular Localization of ncmtRNAs in Plasmocytes Isolated from Individuals Diagnosed with Multiple Myeloma In this example, plasmocytes were obtained from the bone marrow of individuals who had previously been diagnosed with multiple myeloma. Plasmocytes were isolated from individuals prior to treatment with any anticancer therapy.

Methods

Plasmocytes were isolated from the bone marrow of individuals positively diagnosed with multiple myeloma and FISH performed to detect the expression and subcellular localization of SncmtRNA and ASncmtRNA as described above. A probe to the 18S rRNA subunit was used as a positive control.

Results

Figure 2A:
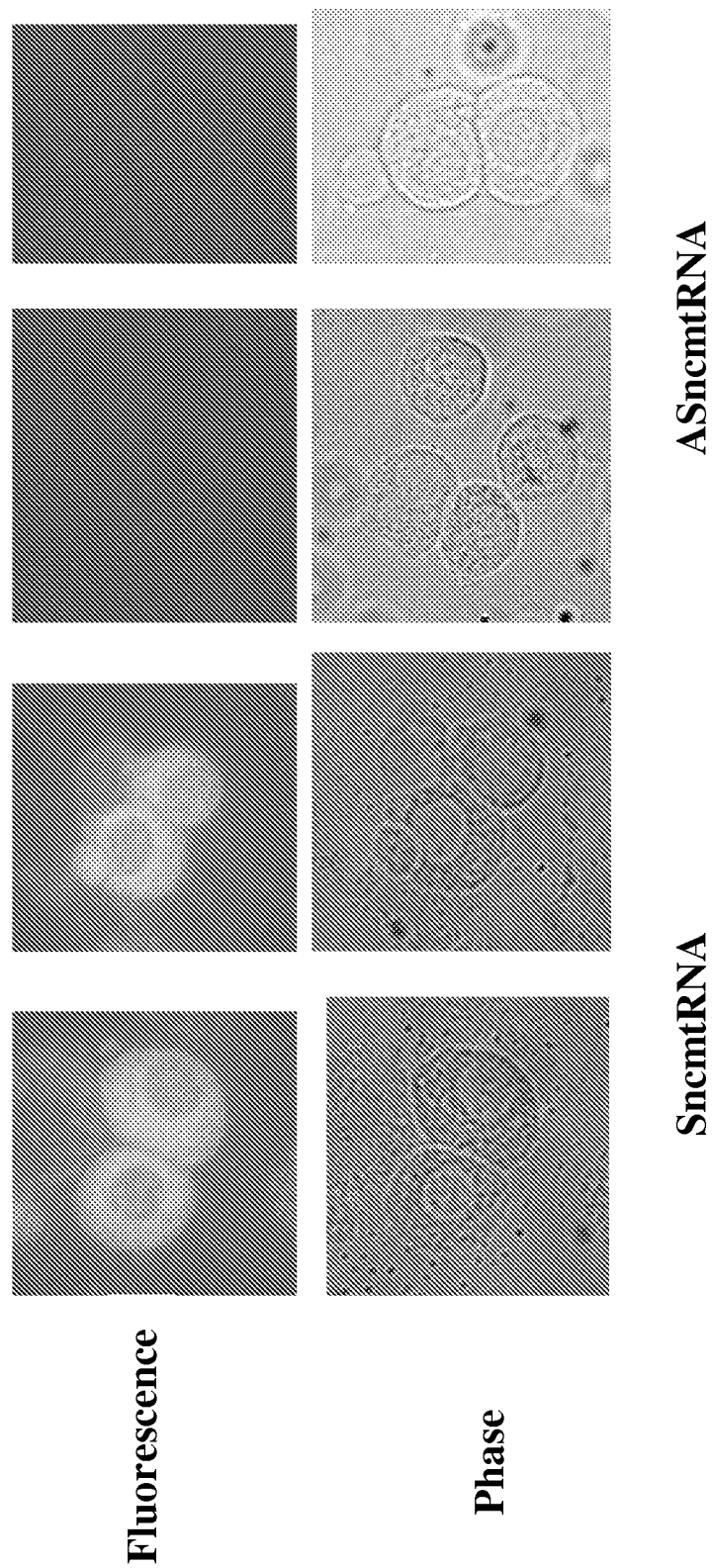
FIG. 2 depicts hybridization signal to both SncmtRNA and ASncmtRNA probes in plasmocytes isolated from the bone marrow of individuals who have been diagnosed with multiple myeloma prior to administration of any anticancer therapy. Myeloma cells are identified by their positive hybridization to the SncmtRNA probe and the lack of hybridization signal to the ASncmtRNA probe (upper panels). SncmtRNA is localized only in the cytoplasm. 18S rRNA serves as a positive control. The lower panels correspond to the phase image of the same cells (FIGS. 2A-C).
Figure 2B:
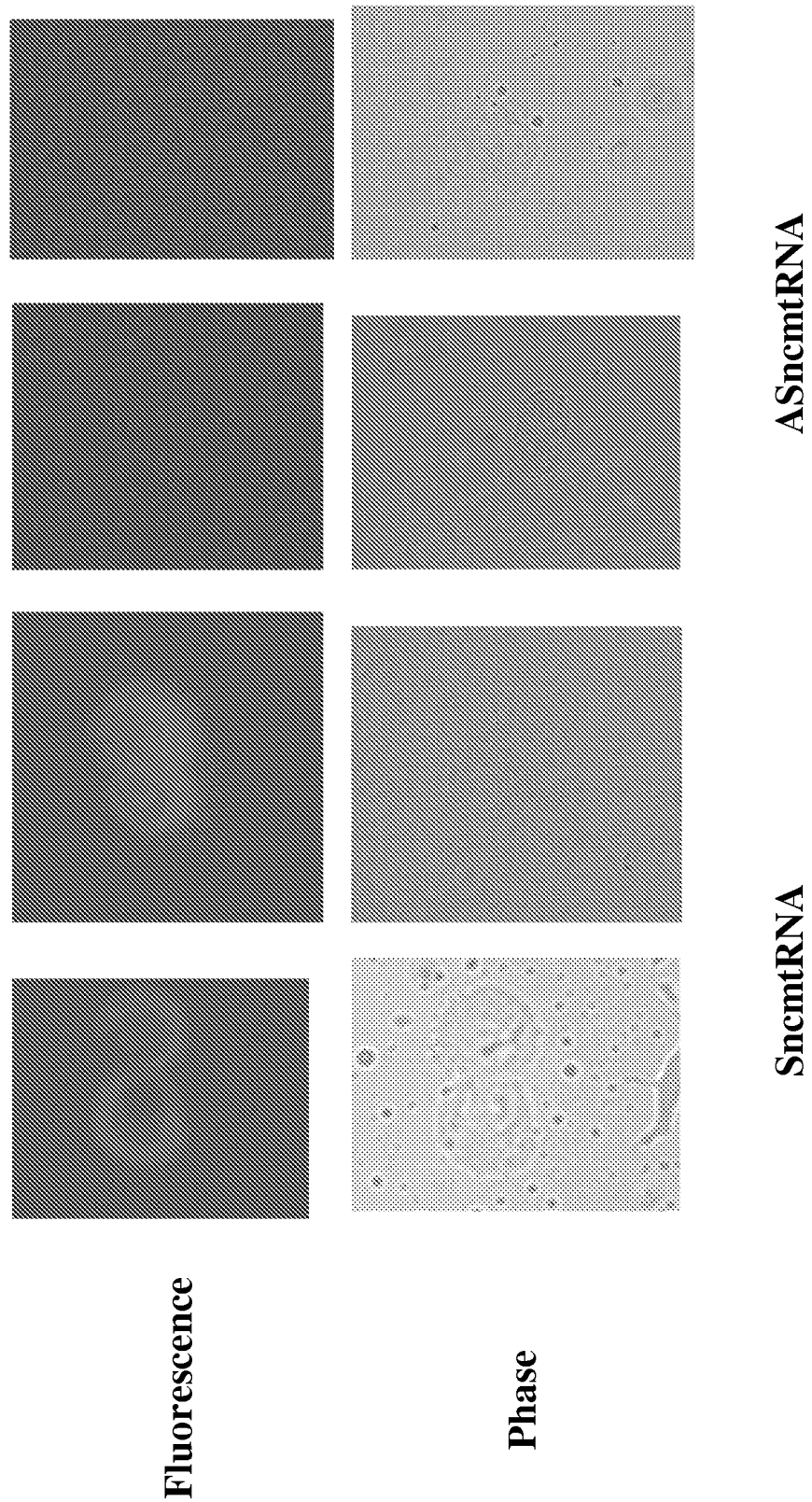
Figure 3A:
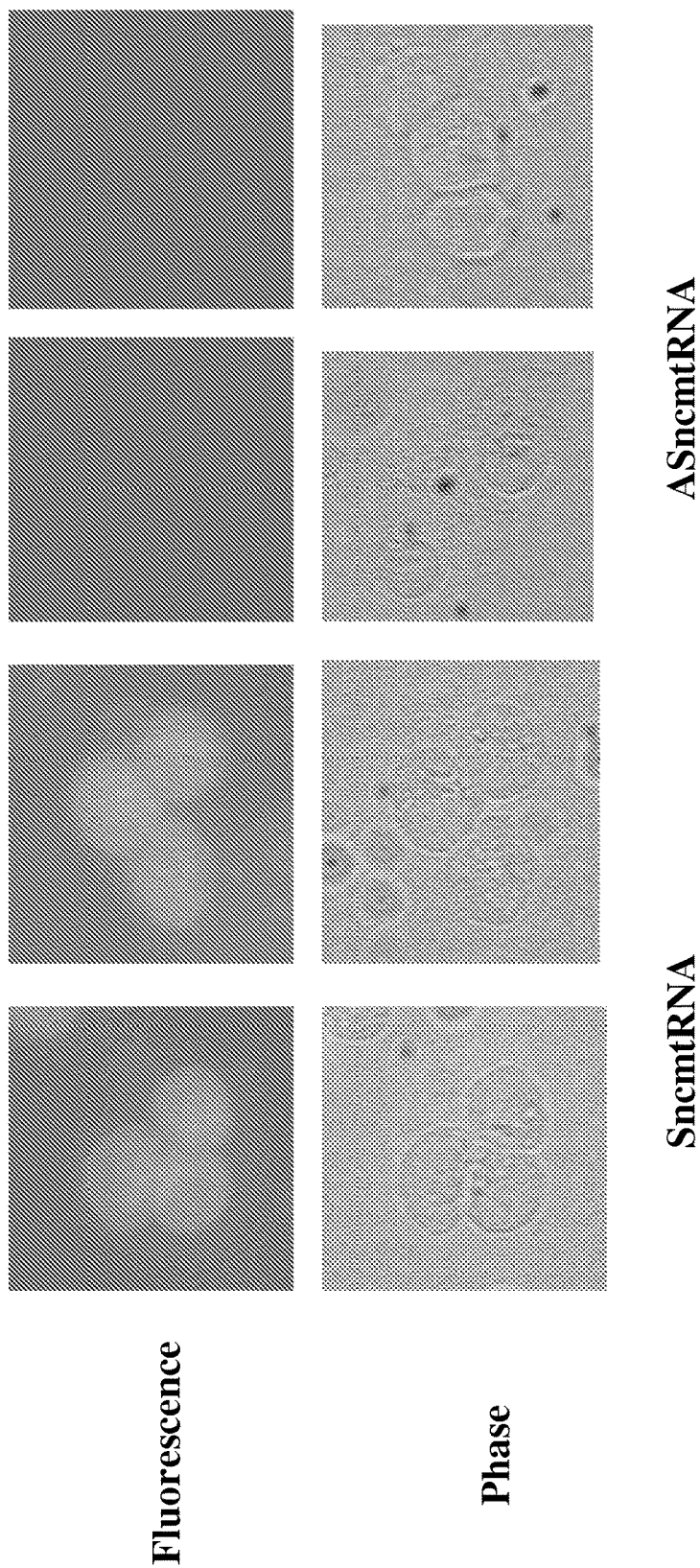
FIG. 3 depicts hybridization signal to both SncmtRNA and ASncmtRNA probes in plasmocytes isolated from the bone marrow of individuals who have been diagnosed with multiple myeloma and have subsequently relapsed following anticancer therapy. Myeloma cells are identified by their positive hybridization to the SncmtRNA probe and the lack of hybridization signal to the ASncmtRNA probe (upper panels). Additionally, SncmtRNA is localized wither primarily in the nucleus (FIGS. 3C-D) or in the cytoplasm and the nucleus (FIGS. 3A-B and E). 18S rRNA serves as a positive control. The lower panels correspond to the phase image of the same cells.
Figure 3B:
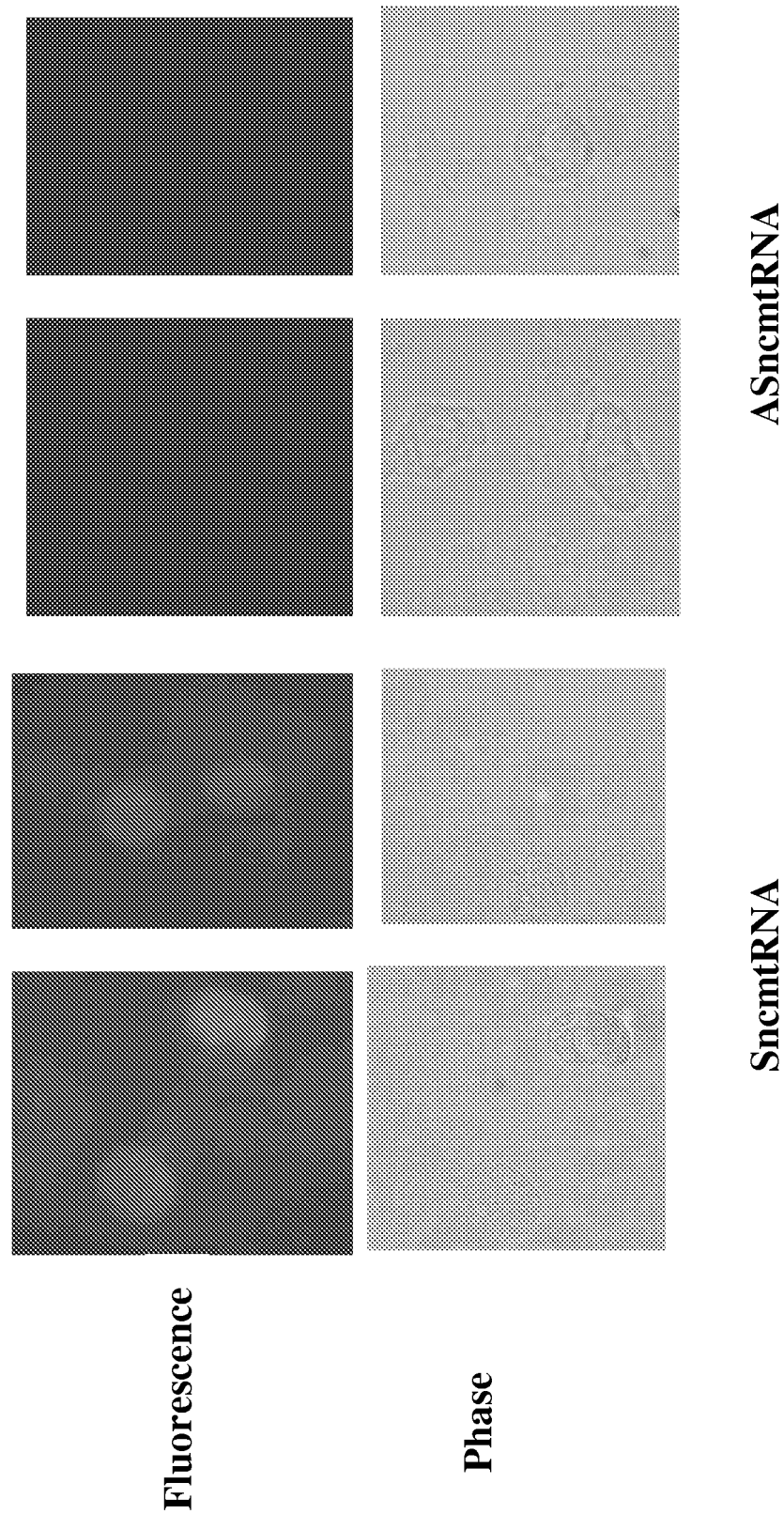
Figure 3C:
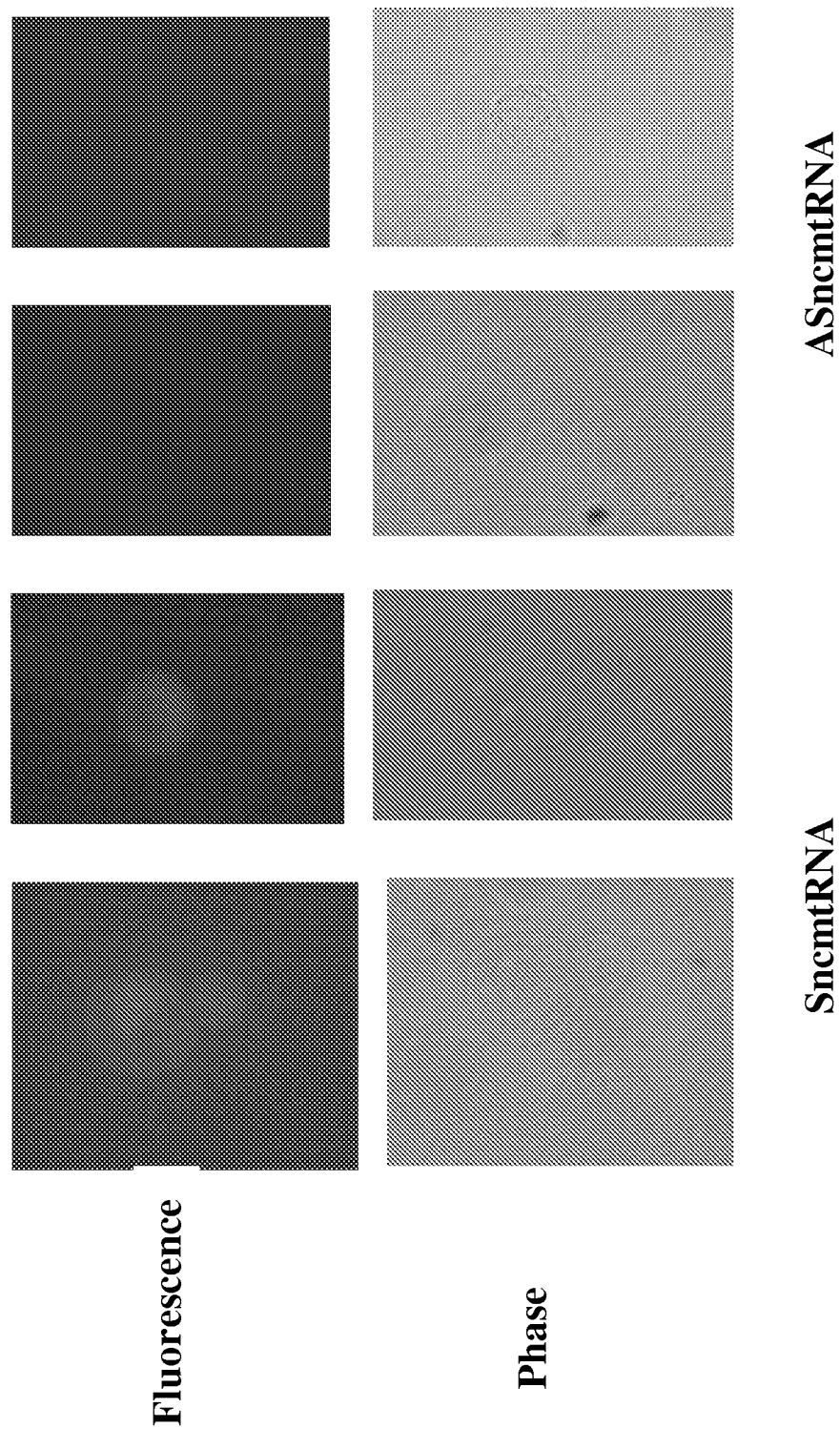
Figure 3D:
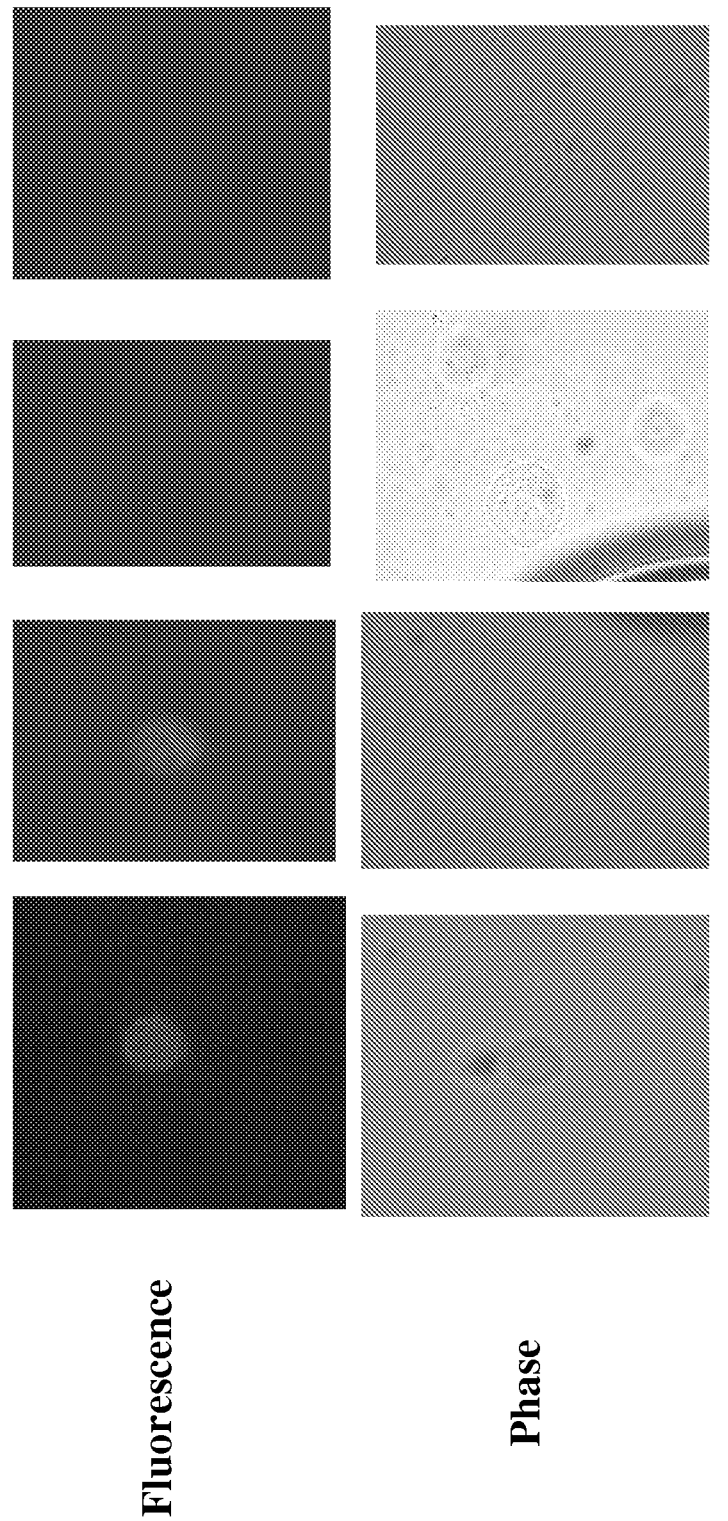
Figure 3E:
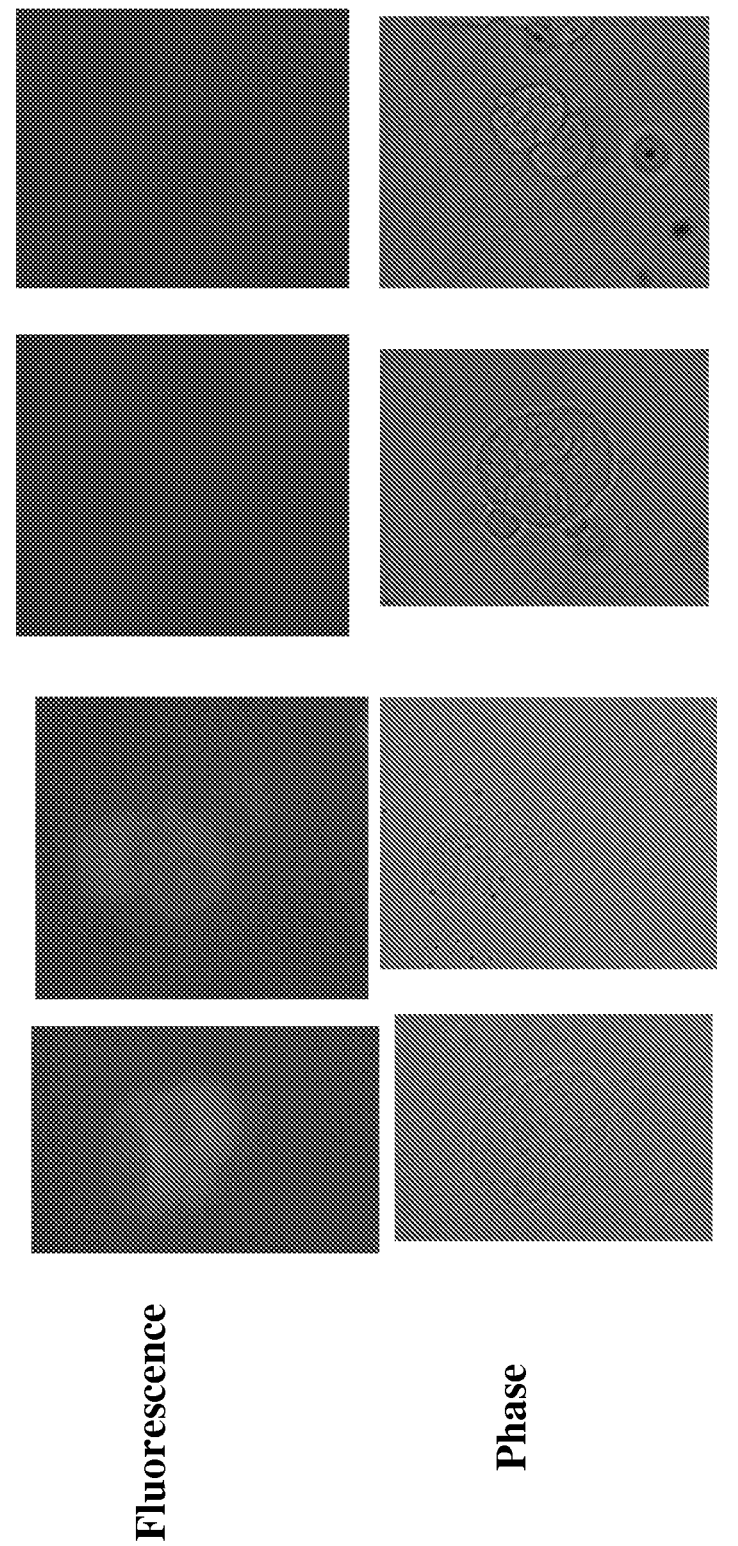

Results are depicted in FIG. 2. FISH staining of plasmocytes reveals positive hybridization to the SncmtRNA probe and the lack of hybridization signal to the ASncmtRNA probe. Additionally, for plasmocytes isolated from individuals who have been diagnosed with multiple myeloma, SncmtRNA is localized only in the cytoplasm of the plasmocytes (FIGS. 2A-C). This pattern of SncmtRNA expression and subcellular localization was generally associated with a more favorable prognosis.

Example 3

Determination of Expression and Subcellular Localization of ncmtRNAs in Plasmocytes Isolated from Individuals Diagnosed with Multiple Myeloma Who have Relapsed Following Treatment In this example, plasmocytes were obtained from the bone marrow of individuals who had previously been diagnosed with multiple myeloma. Plasmocytes were isolated from individuals following treatment with bortezomib (Velcade®) who had suffered subsequent relapse of symptoms.

Methods

Plasmocytes were isolated from the bone marrow of individuals positively diagnosed with multiple myeloma and FISH performed to detect the expression and subcellular localization of SncmtRNA and ASncmtRNA as described above. A probe to the 18S rRNA subunit was used as a positive control.

Results

Results are depicted in FIG. 3. FISH staining of plasmocytes reveals positive hybridization to the SncmtRNA probe and the lack of hybridization signal to the ASncmtRNA probe. Additionally, for plasmocytes isolated from individuals who have been diagnosed with multiple myeloma, treated with bortezomib, and suffered a subsequent relapse of multiple myeloma symptoms, SncmtRNA was localized either mainly in the nucleus of the plasmocytes (FIGS. 3C-D) or both in the cytoplasm and the nucleus (FIGS. 3A-B and E). A probe to the 18S rRNA subunit was used as a positive control.

Example 4

Determination of Expression and Subcellular Localization of ncmtRNAs in Plasmocytes Isolated from Individuals with MGUS In this example, plasmocytes were obtained from the bone marrow of individuals who had previously been diagnosed with monoclonal gammopathy of unknown significance (MGUS).

Methods Plasmocytes were isolated from the bone marrow of individuals with MGUS and FISH performed to detect the expression and subcellular localization of SncmtRNA and ASncmtRNA as described above. A probe to the 18S rRNA subunit was used as a positive control.

Results

Figure 4:
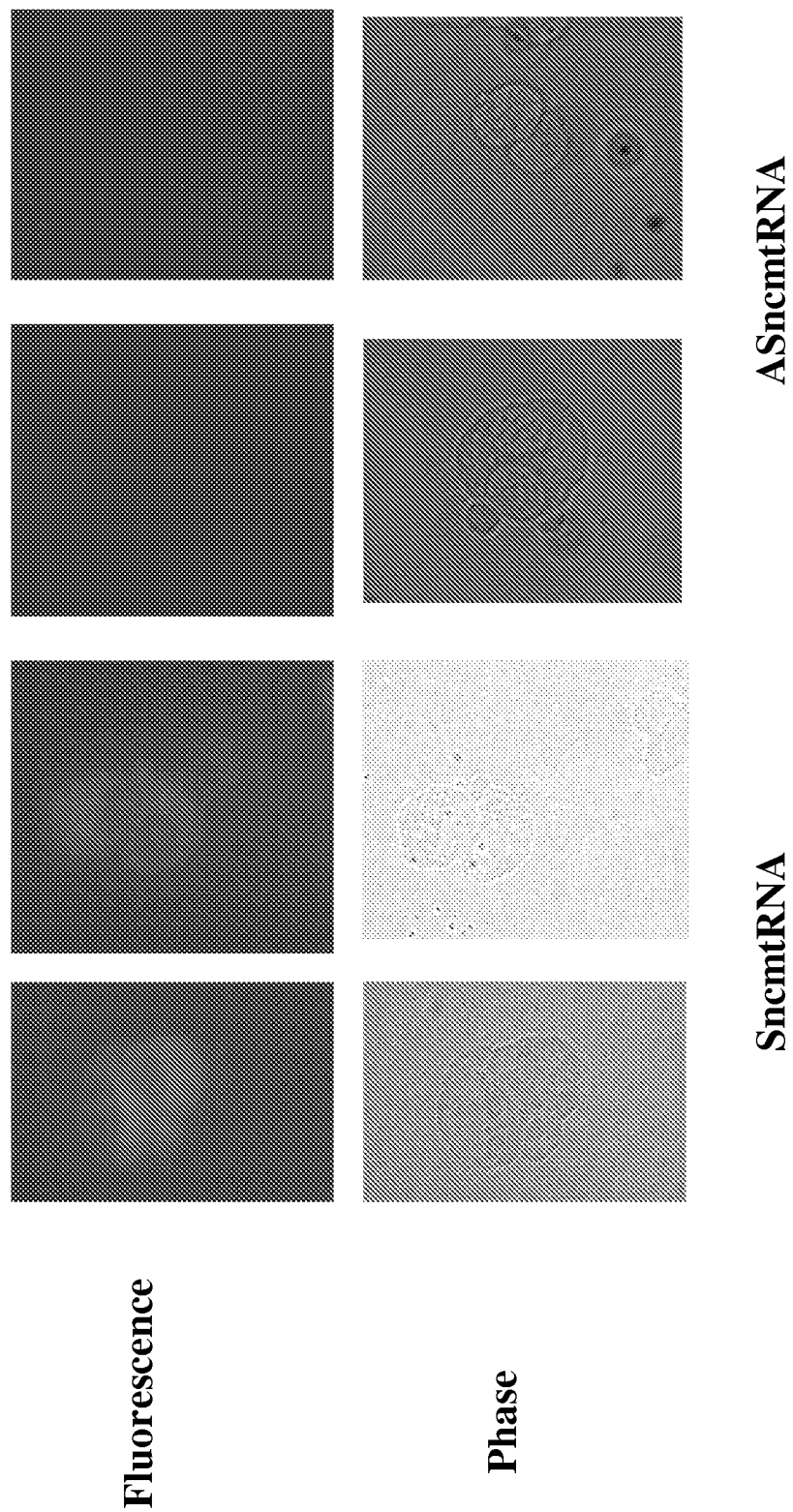
FIG. 4 depicts hybridization signal to both SncmtRNA and ASncmtRNA probes in plasmocytes isolated from the bone marrow of an individual with monoclonal gammopathy of unknown significance (MGUS). These cells show SncmtRNA expression and localization consistent with individuals diagnosed with multiple myeloma but prior to relapse (cytoplasmic localization). ASncmtRNA is absent. The lower panels show the same cells stained with DAPI (nuclear staining).

Results are depicted in FIG. 4. FISH staining of plasmocytes reveals positive hybridization to the SncmtRNA probe and the lack of hybridization signal to the ASncmtRNA probe. Significantly, SncmtRNA is localized only in the cytoplasm of the plasmocytes, consistent with the subcellular localization of SncmtRNA in the plasmocytes of individuals diagnosed with multiple myeloma but prior to relapse.

Example 5

Treatment of a Murine Myeloma Cell Line with Antisense Oligonucleotides to ncmtRNAs Followed by Transplantation into Mice Autologous bone marrow transplantation has become a major treatment option for an increasing number of patients with hematologic cancer such as multiple myeloma. Autologous transplantation (AT) has several potential advantages over allogeneic transplantation. However, the major obstacle to use AT is that the infusion of bone marrow occults tumor cells harbored within the harvested marrow would result in more rapid relapse of disease. To minimize relapse, many authors have taken a new approach: treatment or purge the collected bone marrow with drugs to eliminate the malignant cells or their precursors (cancer stem cells). Post-treatment, the bone marrow will eventually be cleaned of malignant cells.

As a cell model for the purging of bone marrow, we work with the murine myeloma cell line NSO2. Treatment of these cells in vitro with antisense oligonucleotides complementary to the mouse ASncmtRNA induces massive cell death by apoptosis without affecting normal mouse cells. Knocking down the ASncmtRNA induces activation of caspases, DNA fragmentation and causes cells to become annexin V positive, which are all hallmarks of apoptoses. Accordingly, based on these results, we employed these cells to determine if treatment of NSO2 cells with antisense oligonucleotide complementary to the mouse ASncmtRNA prior to transplantation into mice can prevent or decrease symptoms associated with multiple myeloma.

Materials and Methods

NSO2 cells were transfected with 150 nM antisense oligonucleotide control (ASO-C) or 150 nM of an oligonucleotide complementary to the mouse ASncmtRNA (Therapeutic ASO or ASO-1560S) or left untreated (no treatment) for 48 hours. Transfection was carried out with Lipofectamin 2000 according to Invitrogene Instructions. At 48 hours post-transfection, cells were harvested and counted.

Post-treatment, 200,000 cells (controls or treated with the therapeutic ASO or ASO-1560S) were injected intraperitoneally into balb/c mice. Mice survival was follow for 90 days post-cell injection.

Results

Figure 5:
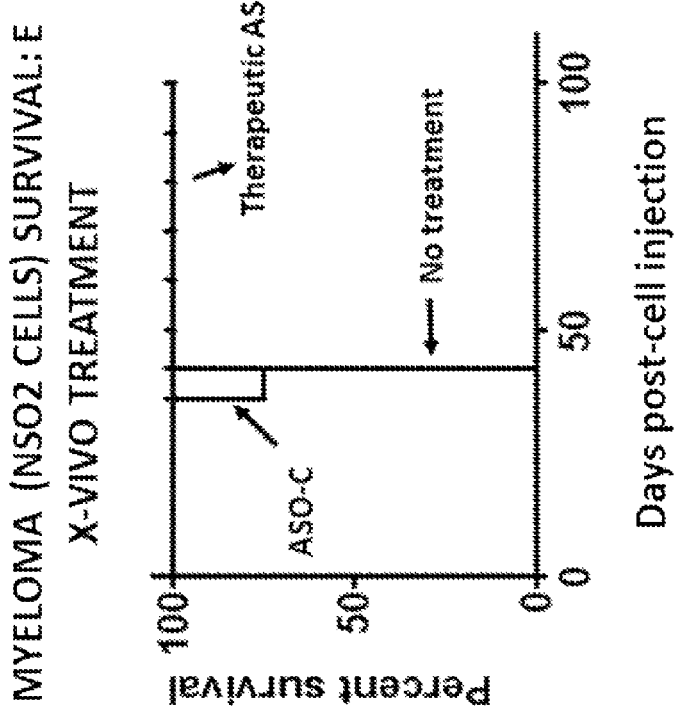
FIG. 5 depicts survival of mice injected with untreated NSO2 cells, NSO2 cells treated with a control antisense oligonucleotide (ASO-C) or cells treated with the therapeutic antisense oligonucleotide ASO-1560S.

As shown in FIG. 5, around day 40 post-cell injection (day 0 on the graph), mice injected with untreated cells or cells treated with ASO-C died. In contrast, mice injected with cells treated with the therapeutic ASO or ASO-1560S exhibit 100% survival after 90 days. At this time, mice were sacrificed for histopathological studies. Compared with untreated mice, no histopathological alteration of liver, spleen, kidney, intestine, heart and lung was observed.

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

SEQUENCES

<210> SEQ ID NO 1
<211> LENGTH: 2374
<212> TYPE: DNA
<213> ORGANISM: Homo sapiens
<400> SEQUENCE: 1

```
tctaatactg gtgatgctag aggtgatgtt tttggtaaac aggcggggta agatttgccg    60
agttcctttt actttttta  accttccctt atgagcatgc ctgtgttggg ttgacagtga   120
gggtaataat gacttgttgg ttgattgtag atattgggct gttaattgtc agttcagtgt   180
tttaatctga cgcaggctta tgcggaggag aatgttttca tgttacttat actaacatta   240
gttcttctat agggtgatag attggtccaa ttgggtgtga ggagttcagt tatatgtttg   300
ggatttttta ggtagtgggt gttgagcttg aacgctttct taattggtgg ctgcttttag   360
gcctactatg ggtgttaaat tttttactct ctctacaagg ttttttccta gtgtccaaag   420
agctgttcct ctttggacta acagttaaat ttacaaggg atttagaggg ttctgtgggc   480
aaatttaaag ttgaactaag attctatctt ggacaaccag ctatcaccag gctcggtagg   540
tttgtcgcct ctacctataa atcttcccac tattttgcta catagacggg tgtgctcttt   600
tagctgttct taggtagctc gtctggtttc ggggtcttga gctttggctc tccttgcaaa   660
gttatttcta gttaattcat tatgcagaag gtataggggt tagtccttgc tatattatgc   720
ttggttataa ttttttcatct ttcccttgcg gtactatatc tattgcgcca ggtttcaatt   780
tctatcgcct atactttatt tgggtaaatg gtttggctaa acctagcccc aaacccactc   840
caccttacta ccagacaacc ttagccaaac catttaccca aataaagtat aggcgataga   900
aattgaaacc tggcgcaata gatatagtac cgcaagggaa agatgaaaaa ttataaccaa   960
gcataatata gcaaggacta acccctatac cttctgcata atgaattaac tagaaataac  1020
tttgcaagga gagccaaagc taagacccce gaaaccagac gagctaccta agaacagcta  1080
aaagagcaca cccgtctatg tagcaaaata gtgggaagat ttataggtag aggcgacaaa  1140
cctaccgagc ctggtgatag ctggttgtcc aagatagaat cttagttcaa cttaaattt  1200
gcccacagaa ccctctaaat ccccttgtaa atttaactgt tagtccaaag aggaacagct  1260
ctttggacac taggaaaaaa ccttgtagag agagtaaaaa atttaacacc catagtaggc  1320
ctaaaagcag ccaccaatta agaaagcgtt caagctcaac acccactacc taaaaatcc   1380
caaacatata actgaactcc tcacacccaa ttggaccaat ctatcaccct atagaagaac  1440
taatgttagt ataagtaaca tgaaaacatt ctcctccgca taagcctgcg tcagattaaa  1500
acactgaact gacaattaac agcccaatat ctacaatcaa ccaacaagtc attattaccc  1560
tcactgtcaa cccaacacag gcatgctcat aaggaaaggt taaaaaaagt aaaaggaact  1620
cggcaaatct tacccogcct gtttaccaaa aacatcacct ctagcatcac cagtattaga  1680
ggcaccgcct gcccagtgac acatgtttaa cggccggcgt accctaaccg tgcaaaggta  1740
gcataatcac ttgttcctta aatagggacc tgtatgaatg gctccacgag ggttcagctg  1800
tctcttactt ttaaccagtg aaattgacct gcccgtgaag aggcgggcat aacacagcaa  1860
gacgagaaga ccctatggag cttttaattta ttaatgcaaa cagtacctaa caaacccaca  1920
ggtcctaaac taccaaacct gcattaaaaa tttcggttgg ggcgacctcg gagcagaacc  1980
caacctccga gcagtacatg ctaagacttc accagtcaaa gcgaactact atactcaatt  2040
gatccaataa cttgaccaac ggaacaagtt acctagggga taacagcgca atcctattct  2100
agagtccata tcaacaatag ggtttacgac ctcgatgttg gatcaggaca tcccgatggt  2160
gcagccgcta ttaaaggttc gtttgttcaa cgattaaagt cctacgtgat ctgagttcag  2220
accggagtaa tccaggtcgg tttctatcta ccttcaaatt cctccctgta cgaaaggaca  2280
```

SEQUENCES

```
agagaaataa ggcctacttc acaaagcgcc ttccccgta aatgatatca tctcaactta 2340
gtattatacc cacacccacc caagaacagg gttt                            2374
```

<210> SEQ ID NO 2
<211> LENGTH: 1679
<212> TYPE: DNA
<213> ORGANISM: Homo saiens
<400> SEQUENCE: 2

```
ggggtcttag ctttggctct ccttgcaaag ttatttctag ttaattcatt atgcagaagg   60
tatagggggtt agtccttgct atattatgct tggttataat ttttcatctt tcccttgcgg  120
tgctaaacct agccccaaac ccactccacc ttactaccag acaaccttag ccaaaccatt  180
tacccaaata aagtatagg gatagaaatt gaaacctggc gcaatagata tagtaccgca  240
agggaaagat gaaaaattat aaccaagcat aatatagcaa ggactaaccc ctataccttc  300
tgcataatga attaactaga aataactttg caaggagagc caaagctaag acccccgaaa  360
ccagacgagc tacctaagaa cagctaaaag agcacacccg tctatgtagc aaaatagtgg  420
gaagatttat aggtagaggc gacaaaccta ccgagcctgg tgatagctgg ttgtccaaga  480
tagaatctta gttcaacttt aaatttgccc acagaaccct ctaaatcccc ttgtaaattt  540
aactgttagt ccaaagagga acagctcttt ggacactagg aaaaaacctt gtagagagag  600
taaaaaattt aacacccata gtaggcctaa aagcagccac caattaagaa agcgttcaag  660
ctcaacaccc actacctaaa aaatcccaaa catataactg aactcctcac acccaattgg  720
accaatctat caccctatag aagaactaat gttagtataa gtaacatgaa acattctcc  780
tccgcataag cctgcgtcag attaaaaacac tgaactgaca attaacagcc caatatctac  840
aatcaaccaa caagtcatta ttaccctcac tgtcaaccca acacaggcat gctcataagg  900
aaaggttaaa aaaagtaaaa ggaactcggc aaatcttacc ccgcctgttt accaaaaaca  960
tcacctctag catcaccagt attagaggca ccgcctgccc agtgacacat gtttaacggc 1020
cgcggtaccc taaccgtgca aaggtagcat aatcacttgt tccttaaata gggacctgta 1080
tgaatggctc cacgagggtt cagctgtctc ttacttttaa ccagtgaaat tgacctgccc 1140
gtgaagaggc gggcataaca cagcaagacg agaagaccct atggagcttt aatttattaa 1200
tgcaaacagt acctaacaaa cccacaggtc ctaaactacc aaacctgcat taaaaatttc 1260
ggttggggcg acctcggagc agaacccaac ctccgagcag tacatgctaa gacttcacca 1320
gtcaaagcga actactatac tcaattgatc caataacttg accaacggaa caagttaccc 1380
tagggataac agcgcaatcc tattctagag tccatatcaa caatagggtt tacgacctcg 1440
atgttggatc aggacatccc aatggtgcag ccgctattaa aggttcgttt gttcaacgat 1500
taaagtccta cgtgatctga gttcagaccg gagtaatcca ggtcggttc tatctacttc 1560
aaattcctcc ctgtacgaaa ggacaagaga aataaggcct acttcacaaa gcgccttccc 1620
ccgtaaatga tatcatctca acttagtatt atacccacac ccacccaaga acagggttt 1679
```

<210> SEQ ID NO 3
<211> LENGTH: 1635
<212> TYPE: DNA
<213> ORGANISM: Homo sapiens
<400> SEQUENCE: 3

```
ggggtcttag ctttggctct ccttgcaaag ttatttctag ttaattcatt atgcagaagg   60
tatagggggtt agtccttgct aaacctagcc ccaaacccca tccaccttac taccagacaa  120
ccttagccaa accatttacc caaataaagt ataggcgata gaaattgaaa cctggcgcaa  180
tagatatagt accgcaaggg aaagatgaaa aattataacc aagcataata tagcaaggac  240
taaccccctat accttctgca taatgaatta actagaaata actttgcaag gagagccaaa  300
gctaagaccc ccgaaaccag acgagctacc taagaacagc taaaagagca cccgtctca  360
tgtagcaaaa tagtgggaag atttataggt agaggcgaca aacctaccga gcctggtgat  420
agctggttgt ccaagataga atcttagttc aactttaaat ttgcccacag aaccctctaa  480
atccccttgt aaatttaact gttagtccaa agaggaacag ctctttggac actaggaaaa  540
aaccttgtag agagtaaaaa aatttaaca cccatagtag gcctaaaagc agccaccaat  600
taagaaagcg ttcaagctca acacccacta cctaaaaaat cccaaacata taactgaact  660
cctcacaccc aattggacca atctatcacc ctatagaaga actaatgtta gtataagtaa  720
catgaaaaca tttcctccg cataagcctg cgtcagatta aaacactgaa ctgacaatta  780
acagcccaat atctacaatc aaccaacaag tcattattac cctcactgtc aacccaacac  840
aggcatgctc ataaggaaag gttaaaaaaa gtaaaaaggaa ctcggcaaat cttaccccgc  900
ctgtttacca aaaacatcac ctctagcatc accagtatta gaggcaccgc ctgcccagtc  960
acacatgttt aacggccgcg gtaccctaac cgtgcaaagg tagcataatc acttgttcct 1020
taaatagggga cctgtatgaa tggctccacg agggttcagc tgtctcttac ttttaaccag 1080
tgaaattgac ctgcccgtga gaggcgggc ataacacagc aagacgagaa gaccctatgg 1140
agctttaatt tattaatgca aacagtacct aacaaaccca caggtcctaa actaccaaac 1200
ctgcattaaa aatttcggtt ggggcgacct cggagcagaa cccaacctcc gagcagtaca 1260
tgctaagact tcaccagtca aagcgaacta ctatactcaa ttgatccaat aacttgacca 1320
acggaacaag ttaccctagg gataacagcg caatcctatt ctagagtcca tatcaacaat 1380
agggtttacg acctcgatgt tggatcagga catcccaatg gtgcagccga tattaaaggt 1440
tcgtttgttc aacgattaaa gtcctacgtg atctgagttc agaccggagt aatccaggtc 1500
ggtttctatc tacttcaaat tcctccctgt acgaaaggac aagagaaata aggcctactt 1560
cacaaagcgc cttccccgt aaatgatatc atctcaactt agtattatac ccacacccac 1620
ccaagaacag ggttt                                                  1635
```

<210> SEQ ID NO 4
<211> LENGTH: 1921
<212> TYPE: DNA
<213> ORGANISM: Homo sapiens
<400> SEQUENCE: 4

```
aacctccgag cagtacatgc taagacttca ccagtcaaag cgaactacta tactcaattg   60
```

| | | | | | |
|---|---|---|---|---|---|
|atccaataac|ttgaccaacg|gaacaagtta|ccctagggat|aacagcgcaa|tcctattcta 120|
|gagtccatat|caacaatagg|gtttacgacc|tcgatgttgg|atcaggacat|cccaatggtg 180|
|cagccgctat|taaaggttcg|tttgttcaac|gattaaagtc|ctacgtgatc|tgagttcaga 240|
|ccggagtaat|ccaggtcggt|ttctatctac|ttcaaattcc|tccctgtacg|aaaggacaag 300|
|agaaataagg|cctacttcac|aaagcgcctt|ccccgtaaa|tgatatcatc|tcaacttagt 360|
|attatacect|gttcttgggt|gggtgtgggt|ataatactaa|gttgagatga|tatcatttac 420|
|gggggaaggc|gctttgtgaa|gtaggcctta|tttctcttgt|cctttcgtac|agggaggaat 480|
|ttgaagtaga|tagaaaccga|cctggattac|tccggtctga|actcagatca|cgtaggactt 540|
|taatcgttga|acaaacgaac|ctttaatagc|ggctgcacca|tcgggatgtc|ctgatccaac 600|
|atcgaggtcg|taaaccctat|tgttgatatg|gactctagaa|taggattgcg|ctgttatccc 660|
|tagggtaact|tgttccgttg|gtcaagttat|tggatcaatt|gagtatagta|gttcgctttg 720|
|actggtgaag|tcttagcatg|tactgctcgg|aggttgggtt|ctgctccgag|gtcgcccccaa 780|
|ccgaaatttt|taatgcaggt|ttggtagttt|aggacctgtg|ggtttgttag|gtactgtttg 840|
|cattaataaa|ttaaagctcc|atagggtctt|ctcgtcttgc|tgtgttatgc|ccgcctcttc 960|
|acgggcaggt|caatttcact|ggttaaaagt|aagagacagc|tgaaccctcg|tggagccatt 900|
|catacaggtc|cctatttaag|gaacaagtga|ttatgctacc|tttgcacggt|tagggtaccg 1020|
|cggccgttaa|acatgtgtca|ctgggcaggc|ggtgcctcta|atactggtga|tgctagaggt 1080|
|gatgtttttg|gtaaacaggc|gggtaagat|ttgccgagtt|cctttactt|tttttaacct 1140|
|ttccttatga|gcatgcctgt|gttgggttga|cagtgagggt|aataatgact|tgttggttga 1200|
|ttgtagatat|tgggctgtta|attgtcagtt|cagtgttttta|atctgcacga|ggcttatgcg 1260|
|gaggagaatg|ttttcatgtt|acttatacta|acattagttc|ttctataggg|tgatagattg 1320|
|gtccaattgg|gtgtgaggag|ttcagttata|tgtttgggat|tttttaggta|gtgggtgttg 1380|
|agcttgaacg|ctttcttaat|tggtggctgc|ttttaggcct|actatgggtg|ttaaattttt 1440|
|tactctctct|acaaggtttt|ttcctagtgt|ccaaagagct|ttcctcttt|ggactaacag 1500|
|ttaaatttac|aaggggattt|agagggttct|gtgggcaaat|ttaaagttga|actaagattc 1560|
|tatcttggac|aaccagctat|caccaggctc|ggtaggtttg|tcgcctctac|ctataaatct 1620|
|tcccactatt|ttgctacata|gacgggtgtg|ctcttttagc|tgttcttagg|tagctcgtct 1680|
|ggtttcgggg|gtcttagctt|tggctctcct|tgcaaagtta|tttctagtta|attcattatg 1740|
|cagaaggtat|aggggttagt|ccttgctata|ttatgcttgg|ttataatttt|tcatctttcc 1800|
|cttgcggtac|tatatctatt|gcgccaggtt|tcaatttcta|tcgcctatac|tttatttggg 1860|
|taaatggttt|ggctaaggtt|gtctggtagt|aaggtggagt|gggtttgggg|ctaggtttag 1920|
|c| | | | |1921|

<210> SEQ ID NO 5
<211> LENGTH: 1744
<212> TYPE: DNA
<213> ORGANISM: Homo sapiens
<400> SEQUENCE: 5

| | | | | | |
|---|---|---|---|---|---|
|tagggataac|agcgcaatcc|tattctagag|tccatatcaa|caatagggtt|tacgacctcg 60|
|atgttggatc|aggacatccc|gatggtgcag|ccgctattaa|aggttcgttt|gttcaacgat 120|
|taaagtccta|cgtgatctga|gttcagaccg|gagtaatcca|ggtcggtttc|tatctacctt 180|
|caaattcctc|cctgttcttg|ggtgggtgtg|gtataatac|taagttgaga|tgatatcatt 240|
|tacggggaa|ggcgctttgt|gaagtaggcc|ttatttctct|tgtcctttcg|tacagggagg 300|
|aatttgaagt|agatagaaac|cgacctggat|tactccggtc|tgaactcaga|tcacgtagga 360|
|ctttaatcgt|tgaacaaacg|aacctttaat|agcggctgca|ccatcgggat|gtcctgatcc 420|
|aacatcgagg|tcgtaaaccc|tattgttgat|atggactcta|gaataggatt|gcgctgttat 480|
|ccctagggta|acttgttccg|ttggtcaagt|tattggatca|attgagtata|gtagttcgct 540|
|ttgactggtg|aagtcttagc|atgtactgct|cggaggttgg|gttctgctcc|gaggtcgccc 600|
|caaccgaaat|ttttaatgca|ggtttggtag|tttaggacct|gtgggttttgt|taggtactgt 660|
|ttgcattaat|aaaattaaagc|tccatagggt|cttctcgtct|tgctgtgtta|tgcccgcctc 720|
|ttcacgggca|ggtcaatttc|actggttaaa|agtaagagac|agctgaaccc|tcgtggagcc 780|
|attcatacag|gtccctattt|aaggaacaag|tgattatgct|acctttgcac|ggttagggta 840|
|ccgcggccgt|taaacatgtg|tcactgggca|ggcggtgcct|ctaatactgg|tgatgctaga 900|
|ggtgatgttt|ttggtaaaca|ggcggggtaa|gatttgccga|gttccttta|cttttttaa 960|
|cctttcctta|tgagcatgcc|tgtgttgggt|tgacagtgag|ggtaataatg|acttgttggt 1020|
|tgattgtaga|tattgggctg|ttaattgtca|gttcagtgtt|ttaatctgac|gcaggctat 1080|
|gcggaggaga|atgttttcat|gttacttata|ctaacattag|ttcttctata|gggtgataga 1140|
|ttggtccaat|tggggtgtgag|gagttcagtt|atatgtttgg|gattttttag|gtagtgggtg 1200|
|ttgagcttga|acgctttctt|aattggtggc|tgcttttagg|cctactatgg|gtgttaaatt 1260|
|ttttactctc|tctacaaggt|ttttcctag|tgtccaaaga|gctgttcctc|tttggactaa 1320|
|cagttaaatt|tacaagggga|tttagagggt|tctgtgggca|aatttaaagt|tgaactaaga 1380|
|ttctatcttg|gacaaccagc|tatcaccagg|ctcggtaggt|ttgtcgcctc|tacctataaa 1440|
|tcttcccact|attttgctac|atagacgggt|gtgctctttt|agctgttctt|aggtagctcg 1500|
|tctggtttcg|gggggtcttag|ctttggctct|ccttgcaaag|ttatttctag|ttaattcatt 1560|
|atgcagaagg|tataggggtt|agtccttgct|atattatgct|tggttataat|ttttcatctt 1620|
|tccctttgcgg|tactatatct|attgcgcag|gtttcaattt|ctatcgccta|ctttattt 1680|
|gggtaaatgg|tttggctaag|gttgtctggt|agtaaggtgg|agtgggtttg|gggctaggtt 1740|
|tagc| | | | |1744|

<210> SEQ ID NO 6
<211> LENGTH: 1854
<212> TYPE: DNA
<213> ORGANISM: Homo sapiens
<400> SEQUENCE: 6

| | | | | | |
|---|---|---|---|---|---|
|gaactcggca|aatcttaccc|cgcctgttta|ccaaaaacat|cacctctagc|atcaccagta 60|
|ttagaggcac|cgcctgccca|gtgacacatg|tttaacggcc|gcggtaccct|aaccgtgcaa 120|
|aggtagcata|atcacttgtt|ccttaaatag|ggacctgtat|gaatggctcc|acgagggttc 180|

| SEQUENCES |
|---|
| agctgtctct tacttttaac cagtgaaatt gacctgcccg tgaagaggcg ggcatgacac 240
agcaagacga gaaggaccta tggagcttta atttattaat gcaaacagta cctaacaaac 300
cctgttcttg ggtgggtgtg ggtataaatac taagttgaga tgatatcatt tacggggggca 360
ggcgctttgt gaagtaggcc ttatttctct tgtcctttcg tacagggagg aatttgaagt 420
agatagaaac cgacctggat tactccggtc tgaactcaga tcacgtagga ctttaatcgt 480
tgaacaaacg aacctttaat agcggctgca ccatcgggat gtcctgatcc aacatcgagg 540
tcgtaaaccc tattgttgat atggactcta gaataggatt gcgctgttat ccctagggta 600
acttgttccg ttggtcaagt tattggatca attgagtata gtagttcgct ttgactggtg 660
aagtcttagc atgtactgct cggaggttgg gttctgctcc gaggtcgccc caaccgaaat 720
ttttaatgca ggtttggtag tttaggacct gtgggtttgt taggtactgt ttgcattaat 780
aaattaaagc tccatagggt cttctcgtct tgctgtgtta tgcccgcctc ttcacgggca 840
ggtcaatttc actggttaaa agtaagagac agctgaaccc tcgtggagcc attcatacag 900
gtccctattt aaggaacaag tgattatgct acctttgcac ggttaggta ccgcggccgt 960
taaacatgtg tcactgggca ggcggtgcct ctaatactgg tgatgctaga ggtgatgttt 1020
ttggtaaaca ggcggggtaa gatttgccga gttccttta ctttttttaa cctttcctta 1080
tgagcatgcc tgtgttgggt tgacagtgag ggtaataatg acttgttggt tgattgtaga 1140
tattgggctg ttaattgtca gttcagtgtt ttaatctgac gcaggcttat gcggaggaga 1200
atgttttcat gttacttata ctaacattag ttcttctata gggtgataga ttggtccaat 1260
tgggtgtgag gagttcagtt atatgtttgg gattttttag gtagtgggtg ttgagcttga 1320
acgctttctt aattggtggc tgcttttagg cctactatgg tgttaaatt ttttactctc 1380
tctacaaggt tttttcctag tgtccaaaga gctgttcctc tttggactaa cagttaaatt 1440
tacaagggga tttagagggt tctgtgggca aatttaaagt tgaactaaga ttctatcttg 1500
gacaaccagc tatcaccagg ctcggtaggt ttgtcgcctc tacctataaa tcttcccact 1560
atttgctac atagacgggt gtgctctttt agctgttctt aggtagctcg tctggtttcg 1620
ggggtcttag ctttggctct ccttgcaaag ttatttctag ttaattcatt atgcagaagg 1680
tatagggttt agtccttgct atattatgct tggttataat ttttcatctt tcccttgcgg 1740
tactatatct attgcgccag gtttcaattt ctatcgccta tactttattt gggtaaatgg 1800
tttggctaag ttgtctggt agtaaggtgg agtgggtttg gggctaggtt tagc        1854 |

<210> SEQ ID NO 7
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 7
taggtttagc accgcaaggg                                            20

<210> SEQ ID NO 8
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 8
taggtttagc aaggactaac                                            20

<210> SEQ ID NO 9
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 9
ggggtaagat ttgccgag                                              18

<210> SEQ ID NO 10
<211> LENGTH: 22
<212> TYPE: DNA
<213> ORGANISM: Artificial Sequence
<220> FEATURE:
<223> OTHER INFORMATION: Antisense Oligonucleotide
<400> SEQUENCE: 10
atgctagagg tgatgttttt gg                                         22

<210> SEQ ID NO 11
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 11
cggtgcctct aatactgg                                              18

<210> SEQ ID NO 12
<211> LENGTH:                                                    20
<212> TYPE: DNA

-continued

```
<213> ORGANISM: Artificial Sequence
<220> FEATURE:
<223> OTHER INFORMATION: Antisense Oligonucleotide
<400> SEQUENCE: 12
gttaaacatg tgtcactggg                                              20

<210> SEQ ID NO 13
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 13
ttgcacggtt agggtacc                                                18

<210> SEQ ID NO 14
<211> LENGTH: 21
<212> TYPE: DNA
<213> ORGANISM: Artificial Sequence
<220> FEATURE:
<223> OTHER INFORMATION: Antisense Oligonucleotide
<400> SEQUENCE: 14
ggaacaagtg attatgctac c                                            21

<210> SEQ ID NO 15
<211> LENGTH: 21
<212> TYPE: DNA
<213> ORGANISM: Artificial Sequence
<220> FEATURE:
<223> OTHER INFORMATION: Antisense Oligonucleotide
<400> SEQUENCE: 15
ggagccattc atacaggtcc c                                            21

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 16
agtaagagac agctgaaccc                                              20

<210> SEQ ID NO 17
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 17
ggcaggtcaa tttcactgg                                               19

<210> SEQ ID NO 18
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 18
gctgtgttat gcccgcctc                                               19

<210> SEQ ID NO 19
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 19
agctccatag ggtcttctc                                               19

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 20
gttaggtact gtttgcatta                                              20
```

| SEQUENCES |
| --- |

```
<210> SEQ ID NO 21
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 21
aagtcttagc atgtactg                                                 18

<210> SEQ ID NO 22
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 22
tagtagttcg ctttgactg                                                19

<210> SEQ ID NO 23
<211> LENGTH: 19
<212> TYPE: DNA
<213> ORGANISM: Artificial Sequence
<220> FEATURE:
<223> OTHER INFORMATION: OAntisense Oligonucleotide
<400> SEQUENCE: 23
caagttattg gatcaattg                                                19

<210> SEQ ID NO 24
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 24
gggtaacttg ttccgttg                                                 18

<210> SEQ ID NO 25
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 25
aataggattg cgctgtta                                                 18

<210> SEQ ID NO 26
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 26
cctattgttg atatggac                                                 18

<210> SEQ ID NO 27
<211> LENGTH: 17
<212> TYPE: DNA
<213> ORGANISM: Artificial Sequence
<220> FEATURE:
<223> OTHER INFORMATION: Antisense Oligonucleotide
<400> SEQUENCE: 27
ctgatccaac atcgagg                                                  17

<210> SEQ ID NO 28
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 28
tagcggctgc accattgg                                                 18

<210> SEQ ID NO 29
<211> LENGTH: 19
<212> TYPE: DNA
<213> ORGANISM: Artificial Sequence
```

| SEQUENCES |
| --- |

```
<220> FEATURE:
<223> OTHER INFORMATION: Antisense Oligonucleotide
<400> SEQUENCE: 29
gttgaacaaa cgaaccttt                                                  19

<210> SEQ ID NO 30
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 30
aactcagatc acgtaggac                                                  19

<210> SEQ ID NO 31
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 31
cgacctggat tactccgg                                                   18

<210> SEQ ID NO 32
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 32
ggaatttgaa gtagatag                                                   18

<210> SEQ ID NO 33
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 33
ctcttgtcct ttcgtacag                                                  19

<210> SEQ ID NO 34
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 34
ggcgctttgt gaagtagg                                                   18

<210> SEQ ID NO 35
<211> LENGTH: 22
<212> TYPE: DNA
<213> ORGANISM: Artificial Sequence
<220> FEATURE:
<223> OTHER INFORMATION: Antisense Oligonucleotide
<400> SEQUENCE: 35
gttgagatga tatcatttac gg                                              22

<210> SEQ ID NO 36
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 36
cacccaccca agaacagg                                                   18

<210> SEQ ID NO 37
<211> LENGTH: 25
<212> TYPE: DNA
<213> ORGANISM: Artificial Sequence
<220> FEATURE:
<223> OTHER INFORMATION: Antisense Oligonucleotide
<400> SEQUENCE: 37
caacttagta ttatacccac accca                                           25
```

| SEQUENCES |
|---|
| <210> SEQ ID NO 38
<211> LENGTH: 22
<212> TYPE: DNA
<213> ORGANISM: Artificial Sequence
<220> FEATURE:
<223> OTHER INFORMATION: Antisense Oligonucleotide
<400> SEQUENCE: 38
tcccccgtaa atgattacat ct                                              22

<210> SEQ ID NO 39
<211> LENGTH: 25
<212> TYPE: DNA
<213> ORGANISM: Artificial Sequence
<220> FEATURE:
<223> OTHER INFORMATION: Antisense Oligonucleotide
<400> SEQUENCE: 39
gagaaataag gcctacttca caaag                                           25

<210> SEQ ID NO 40
<211> LENGTH: 22
<212> TYPE: DNA
<213> ORGANISM: Artificial Sequence
<220> FEATURE:
<223> OTHER INFORMATION: Antisense Oligonucleotide
<400> SEQUENCE: 40
caaattcctc cctgtacgaa ag                                              22

<210> SEQ ID NO 41
<211> LENGTH: 24
<212> TYPE: DNA
<213> ORGANISM: Artificial Sequence
<220> FEATURE:
<223> OTHER INFORMATION: Antisense Oligonucleotide
<400> SEQUENCE: 41
agtaatccag gtcggtttct atct                                            24

<210> SEQ ID NO 42
<211> LENGTH: 24
<212> TYPE: DNA
<213> ORGANISM: Artificial Sequence
<220> FEATURE:
<223> OTHER INFORMATION: Antisense Oligonucleotide
<400> SEQUENCE: 42
aagtcctagc tgatctgagt tcag                                            24

<210> SEQ ID NO 43
<211> LENGTH: 25
<212> TYPE: DNA
<213> ORGANISM: Artificial Sequence
<220> FEATURE:
<223> OTHER INFORMATION: Antisense Oligonucleotide
<400> SEQUENCE: 43
gctattaaag gttcgtttgt tcaac                                           25

<210> SEQ ID NO 44
<211> LENGTH: 16
<212> TYPE: DNA
<213> ORGANISM: Artificial Sequence
<220> FEATURE:
<223> OTHER INFORMATION: Antisense Oligonucleotide
<400> SEQUENCE: 44
tcccgatggt gcagcc                                                     16

<210> SEQ ID NO 45
<211> LENGTH: 22
<212> TYPE: DNA
<213> ORGANISM: Artificial Sequence
<220> FEATURE:
<223> OTHER INFORMATION: Antisense Oligonucleotide
<400> SEQUENCE: 45
ttacgacctc gatgttggat ca                                              22

<210> SEQ ID NO 46
<211> LENGTH: 25
<212> TYPE: DNA
<213> ORGANISM: Artificial Sequence
<220> FEATURE: |

| SEQUENCES |
| --- |

```
<223> OTHER INFORMATION: Antisense Oligonucleotide
<400> SEQUENCE: 46
atcctattct agagtccata tcaac                                           25

<210> SEQ ID NO 47
<211> LENGTH: 24
<212> TYPE: DNA
<213> ORGANISM: Artificial Sequence
<220> FEATURE:
<223> OTHER INFORMATION: Antisense Oligonucleotide
<400> SEQUENCE: 47
aataggattg cgctgttatc ccta                                            24

<210> SEQ ID NO 48
<211> LENGTH: 24
<212> TYPE: DNA
<213> ORGANISM: Artificial Sequence
<220> FEATURE:
<223> OTHER INFORMATION: Antisense Oligonucleotide
<400> SEQUENCE: 48
tagggataac agcgcatacc tatt                                            24

<210> SEQ ID NO 49
<211> LENGTH: 23
<212> TYPE: DNA
<213> ORGANISM: Artificial Sequence
<220> FEATURE:
<223> OTHER INFORMATION: Antisense Oligonucleotide
<400> SEQUENCE: 49
ggaacaagtt accctaggga taa                                             23

<210> SEQ ID NO 50
<211> LENGTH: 23
<212> TYPE: DNA
<213> ORGANISM: Artificial Sequence
<220> FEATURE:
<223> OTHER INFORMATION: Antisense Oligonucleotide
<400> SEQUENCE: 50
ttgatccaat aacttgacca acg                                             23

<210> SEQ ID NO 51
<211> LENGTH: 21
<212> TYPE: DNA
<213> ORGANISM: Artificial Sequence
<220> FEATURE:
<223> OTHER INFORMATION: Antisense Oligonucleotide
<400> SEQUENCE: 51
acttcaccag tcaaagcgaa c                                               21

<210> SEQ ID NO 52
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 52
aacccaacct ccgagcag                                                   18

<210> SEQ ID NO 53
<211> LENGTH: 16
<212> TYPE: DNA
<213> ORGANISM: Artificial Sequence
<220> FEATURE:
<223> OTHER INFORMATION: Antisense Oligonucleotide
<400> SEQUENCE: 53
gttggggcga cctcgg                                                     16

<210> SEQ ID NO 54
<211> LENGTH: 22
<212> TYPE: DNA
<213> ORGANISM: Artificial Sequence
<220> FEATURE:
<223> OTHER INFORMATION: Antisense Oligonucleotide
<400> SEQUENCE: 54
aaactaccaa acctgcttaa aa                                              22

<210> SEQ ID NO 55
```

| SEQUENCES |
| --- |
| <211> LENGTH: 24
<212> TYPE: DNA
<213> ORGANISM: Artificial Sequence
<220> FEATURE:
<223> OTHER INFORMATION: Antisense Oligonucleotide
<400> SEQUENCE: 55
aaacagtacc taacaaaccc acag                                        24

<210> SEQ ID NO 56
<211> LENGTH: 25
<212> TYPE: DNA
<213> ORGANISM: Artificial Sequence
<220> FEATURE:
<223> OTHER INFORMATION: Antisense Oligonucleotide
<400> SEQUENCE: 56
gaccctatgg agctttaatt tatta                                       25

<210> SEQ ID NO 57
<211> LENGTH: 23
<212> TYPE: DNA
<213> ORGANISM: Artificial Sequence
<220> FEATURE:
<223> OTHER INFORMATION: Antisense Oligonucleotide
<400> SEQUENCE: 57
cataacacag caagacgaga aga                                         23

<210> SEQ ID NO 58
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 58
tgacctgccc gtgaagag                                               18

<210> SEQ ID NO 59
<211> LENGTH: 26
<212> TYPE: DNA
<213> ORGANISM: Artificial Sequence
<220> FEATURE:
<223> OTHER INFORMATION: Antisense Oligonucleotide
<400> SEQUENCE: 59
cagctgtctc ttactttttaa ccagtg                                     26

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 60
ctgtatgaat ggctccacga                                             20

<210> SEQ ID NO 61
<211> LENGTH: 26
<212> TYPE: DNA
<213> ORGANISM: Artificial Sequence
<220> FEATURE:
<223> OTHER INFORMATION: Antisense Oligonucleotide
<400> SEQUENCE: 61
agcataatca cttgttcctt aaatag                                      26

<210> SEQ ID NO 62
<211> LENGTH: 23
<212> TYPE: DNA
<213> ORGANISM: Artificial Sequence
<220> FEATURE:
<223> OTHER INFORMATION: Antisense Oligonucleotide
<400> SEQUENCE: 62
accgtgcaaa ggtagcataa tca                                         23

<210> SEQ ID NO 63
<211> LENGTH: 23
<212> TYPE: DNA
<213> ORGANISM: Artificial Sequence
<220> FEATURE:
<223> OTHER INFORMATION: Antisense Oligonucleotide |

| SEQUENCES |
|---|

```
<400> SEQUENCE: 63
tgattatgct acctttgcac ggt                                      23

<210> SEQ ID NO 64
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 64
gtaccctaac cgtgcaaag                                           19

<210> SEQ ID NO 65
<211> LENGTH: 21
<212> TYPE: DNA
<213> ORGANISM: Artificial Sequence
<220> FEATURE:
<223> OTHER INFORMATION: Antisense Oligonucleotide
<400> SEQUENCE: 65
cctgcccagtgacacatgtt t                                         21

<210> SEQ ID NO 66
<211> LENGTH: 25
<212> TYPE: DNA
<213> ORGANISM: Artificial Sequence
<220> FEATURE:
<223> OTHER INFORMATION: Antisense Oligonucleotide
<400> SEQUENCE: 66
cacctctagc atcaccagta ttaga                                    25

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 67
cttaccccgc ctgtttacca                                          20

<210> SEQ ID NO 68
<211> LENGTH: 26
<212> TYPE: DNA
<213> ORGANISM: Artificial Sequence
<220> FEATURE:
<223> OTHER INFORMATION: Antisense Oligonucleotide
<400> SEQUENCE: 68
aggttaaaaa aagtaaaagg aactcg                                   26

<210> SEQ ID NO 69
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 69
cccaacacag gcatgctca                                           19

<210> SEQ ID NO 70
<211> LENGTH: 24
<212> TYPE: DNA
<213> ORGANISM: Artificial Sequence
<220> FEATURE:
<223> OTHER INFORMATION: Antisense Oligonucleotide
<400> SEQUENCE: 70
accaacaagt cattattacc ctca                                     24

<210> SEQ ID NO 71
<211> LENGTH: 24
<212> TYPE: DNA
<213> ORGANISM: Artificial Sequence
<220> FEATURE:
<223> OTHER INFORMATION: Antisense Oligonucleotide
<400> SEQUENCE: 71
tgacaattaa cagcccaata tcta                                     24

<210> SEQ ID NO 72
<211> LENGTH: 21
```

```
<212> TYPE: DNA
<213> ORGANISM: Artificial Sequence
<220> FEATURE:
<223> OTHER INFORMATION: Antisense Oligonucleotide
<400> SEQUENCE: 72
gcctgcgtca gattaaaaca c                                         21

<210> SEQ ID NO 73
<211> LENGTH: 24
<212> TYPE: DNA
<213> ORGANISM: Artificial Sequence
<220> FEATURE:
<223> OTHER INFORMATION: Antisense Oligonucleotide
<400> SEQUENCE: 73
gtaacatgaa aacattctcc tccg                                      24

<210> SEQ ID NO 74
<211> LENGTH: 28
<212> TYPE: DNA
<213> ORGANISM: Artificial Sequence
<220> FEATURE:
<223> OTHER INFORMATION: Antisense Oligonucleotide
<400> SEQUENCE: 74
tatcacccta tagaagaact aatgttag                                  28

<210> SEQ ID NO 75
<211> LENGTH: 21
<212> TYPE: DNA
<213> ORGANISM: Artificial Sequence
<220> FEATURE:
<223> OTHER INFORMATION: Antisense Oligonucleotide
<400> SEQUENCE: 75
ctgaactcct cacacccaat t                                         21

<210> SEQ ID NO 76
<211> LENGTH: 23
<212> TYPE: DNA
<213> ORGANISM: Artificial Sequence
<220> FEATURE:
<223> OTHER INFORMATION: Antisense Oligonucleotide
<400> SEQUENCE: 76
cactacctaa aaatcccaa aca                                        23

<210> SEQ ID NO 77
<211> LENGTH: 21
<212> TYPE: DNA
<213> ORGANISM: Artificial Sequence
<220> FEATURE:
<223> OTHER INFORMATION: Antisense Oligonucleotide
<400> SEQUENCE: 77
ttaagaaagc gttcaagctc a                                         21

<210> SEQ ID NO 78
<211> LENGTH: 21
<212> TYPE: DNA
<213> ORGANISM: Artificial Sequence
<220> FEATURE:
<223> OTHER INFORMATION: Antisense Oligonucleotide
<400> SEQUENCE: 78
catagtaggc ctaaaagcag c                                         21

<210> SEQ ID NO 79
<211> LENGTH: 26
<212> TYPE: DNA
<213> ORGANISM: Artificial Sequence
<220> FEATURE:
<223> OTHER INFORMATION: Antisense Oligonucleotide
<400> SEQUENCE: 79
aaaccttgta gagagagtaa aaaatt                                    26

<210> SEQ ID NO 80
<211> LENGTH: 24
<212> TYPE: DNA
<213> ORGANISM: Artificial Sequence
<220> FEATURE:
<223> OTHER INFORMATION: Antisense Oligonucleotide
<400> SEQUENCE: 80
```

-continued

| SEQUENCES |
|---| aaagaggaac agctctttgg acac                                        24

<210> SEQ ID NO 81
<211> LENGTH: 24
<212> TYPE: DNA
<213> ORGANISM: Artificial Sequence
<220> FEATURE:
<223> OTHER INFORMATION: Antisense Oligonucleotide
<400> SEQUENCE: 81
aatccccttg taaatttaac tgtt                                        24

<210> SEQ ID NO 82
<211> LENGTH: 21
<212> TYPE: DNA
<213> ORGANISM: Artificial Sequence
<220> FEATURE:
<223> OTHER INFORMATION: Antisense Oligonucleotide
<400> SEQUENCE: 82
ctttaaattt gcccacagaa c                                           21

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 83
ggttgtccaa gatagaatct                                             20

<210> SEQ ID NO 84
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 84
acaaacctac cgagcctgg                                              19

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 85
aagatttata ggtagaggcg                                             20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 86
cccgtctatg tagcaaaata                                             20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 87
acctaagaac agctaaaaga                                             20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 88
taagaccccc gaaaccagac                                             20

<210> SEQ ID NO 89
<211> LENGTH: 20
<212> TYPE: DNA

| SEQUENCES |
|---|

```
<213> ORGANISM: Artificial Sequence
<220> FEATURE:
<223> OTHER INFORMATION: Antisense Oligonucleotide
<400> SEQUENCE: 89
ataactttgc aaggagagcc                                                 20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 90
cttctgcata atgaattaac                                                 20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 91
atatagcaag gactaacccc                                                 20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 92
agatgaaaaa ttataaccaa                                                 20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 93
caatagatat agtaccgcaa                                                 20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 94
aggcgataga aattgaaacc                                                 20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 95
tagccaaacc atttacccaa                                                 20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 96
caccttacta ccagacaacc                                                 20

<210> SEQ ID NO 97
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 97
ctaaacctag ccccaaacc                                                  19
```

| SEQUENCES |
| --- |

```
<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 98
ctagcatcac cagtattaga                                         20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 99
ttaccaaaaa catcacctct                                         20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 100
gaactcggca aatcttaccc                                         20

<210> SEQ ID NO 101
<211> LENGTH: 20
<212> TYPE: DNA
<213> ORGANISM: Artificial Sequence
<220> FEATURE:
<223> OTHER INFORMATION: Sense Oligonucleotide
<400> SEQUENCE: 101
gggtaagatt tgccgagttc                                         20

<210> SEQ ID NO 102
<211> LENGTH: 21
<212> TYPE: DNA
<213> ORGANISM: Artificial Sequence
<220> FEATURE:
<223> OTHER INFORMATION: Antisense Oligonucleotide
<400> SEQUENCE: 102
gctcataagg aaaggttaaa a                                       21

<210> SEQ ID NO 103
<211> LENGTH: 17
<212> TYPE: DNA
<213> ORGANISM: Artificial Sequence
<220> FEATURE:
<223> OTHER INFORMATION: Antisense Oligonucleotide
<400> SEQUENCE: 103
gtcaacccaa cacaggc                                            17

<210> SEQ ID NO 104
<211> LENGTH: 21
<212> TYPE: DNA
<213> ORGANISM: Artificial Sequence
<220> FEATURE:
<223> OTHER INFORMATION: Antisense Oligonucleotide
<400> SEQUENCE: 104
accaacaagt cattattacc c                                       21

<210> SEQ ID NO 105
<211> LENGTH: 22
<212> TYPE: DNA
<213> ORGANISM: Artificial Sequence
<220> FEATURE:
<223> OTHER INFORMATION: Sense Oligonucleotide
<400> SEQUENCE: 105
ggttgattgt agatattggg ct                                      22

<210> SEQ ID NO 106
<211> LENGTH: 20
<212> TYPE: DNA
<213> ORGANISM: Artificial Sequence
```

| SEQUENCES |
|---|
| <220> FEATURE:<br><223> OTHER INFORMATION: Antisense Oligonucleotide<br><400> SEQUENCE: 106<br>attaacagcc caatatctac                                    20 |
| <210> SEQ ID NO 107<br><211> LENGTH: 20<br><212> TYPE: DNA<br><213> ORGANISM: Artificial Sequence<br><220> FEATURE:<br><223> OTHER INFORMATION: Antisense Oligonucleotide<br><400> SEQUENCE: 107<br>tgcgtcagat taaaacactg                                    20 |
| <210> SEQ ID NO 108<br><211> LENGTH: 20<br><212> TYPE: DNA<br><213> ORGANISM: Artificial Sequence<br><220> FEATURE:<br><223> OTHER INFORMATION: Antisense Oligonucleotide<br><400> SEQUENCE: 108<br>aaaacattct cctccgcata                                    20 |
| <210> SEQ ID NO 109<br><211> LENGTH: 18<br><212> TYPE: DNA<br><213> ORGANISM: Artificial Sequence<br><220> FEATURE:<br><223> OTHER INFORMATION: Antisense Oligonucleotide<br><400> SEQUENCE: 109<br>gttagtataa gtaacatg                                       18 |
| <210> SEQ ID NO 110<br><211> LENGTH: 19<br><212> TYPE: DNA<br><213> ORGANISM: Artificial Sequence<br><220> FEATURE:<br><223> OTHER INFORMATION: Antisense Oligonucleotide<br><400> SEQUENCE: 110<br>tggaccaatc tatcaccct                                     19 |
| <210> SEQ ID NO 111<br><211> LENGTH: 20<br><212> TYPE: DNA<br><213> ORGANISM: Artificial Sequence<br><220> FEATURE:<br><223> OTHER INFORMATION: Antisense Oligonucleotide<br><400> SEQUENCE: 111<br>acatataact gaactcctca                                    20 |
| <210> SEQ ID NO 112<br><211> LENGTH: 20<br><212> TYPE: DNA<br><213> ORGANISM: Artificial Sequence<br><220> FEATURE:<br><223> OTHER INFORMATION: Antisense Oligonucleotide<br><400> SEQUENCE: 112<br>cacccactac ctaaaaaatc                                   20 |
| <210> SEQ ID NO 113<br><211> LENGTH: 20<br><212> TYPE: DNA<br><213> ORGANISM: Artificial Sequence<br><220> FEATURE:<br><223> OTHER INFORMATION: Antisense Oligonucleotide<br><400> SEQUENCE: 113<br>caccaattaa gaaagcgttg                                    20 |
| <210> SEQ ID NO 114<br><211> LENGTH: 22<br><212> TYPE: DNA<br><213> ORGANISM: Artificial Sequence<br><220> FEATURE:<br><223> OTHER INFORMATION: Antisense Oligonucleotide<br><400> SEQUENCE: 114<br>taggcctaaa agcagccacc aa                                 22 |

|SEQUENCES|
|---|

<210> SEQ ID NO 115
<211> LENGTH: 22
<212> TYPE: DNA
<213> ORGANISM: Artificial Sequence
<220> FEATURE:
<223> OTHER INFORMATION: Sense Oligonucleotide
<400> SEQUENCE: 115
ttggtggctg cttttaggcc to                                         22

<210> SEQ ID NO 116
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 116
taacacccat agtaggcct                                             19

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 117
aaccttgtag agagagtaaa                                            20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 118
aacagctctt tggacactag                                            20

<210> SEQ ID NO 119
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 119
aactgttagt ccaaagag                                              18

<210> SEQ ID NO 120
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 120
ctctaaatcc ccttgtaaa                                             19

<210> SEQ ID NO 121
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 121
actttaaatt tgcccacag                                             19

<210> SEQ ID NO 122
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 122
ggttgtccaa gatagaatc                                             19

<210> SEQ ID NO 123
<211> LENGTH: 19
<212> TYPE: DNA
<213> ORGANISM: Artificial Sequence
<220> FEATURE:

| SEQUENCES |
|---|

```
<223> OTHER INFORMATION: Antisense Oligonucleotide
<400> SEQUENCE: 123
acaaacctac cgagcctcc                                               19

<210> SEQ ID NO 124
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 124
atttataggt tagaggcg                                                18

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 125
atgtagcaaa atagtgggaa                                              20

<210> SEQ ID NO 126
<211> LENGTH: 21
<212> TYPE: DNA
<213> ORGANISM: Artificial Sequence
<220> FEATURE:
<223> OTHER INFORMATION: Antisense Oligonucleotide
<400> SEQUENCE: 126
taagaacagc taaaagagca c                                            21

<210> SEQ ID NO 127
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 127
cgaaaccaga cgagctac                                                18

<210> SEQ ID NO 128
<211> LENGTH: 22
<212> TYPE: DNA
<213> ORGANISM: Artificial Sequence
<220> FEATURE:
<223> OTHER INFORMATION: Sense Oligonucleotide
<400> SEQUENCE: 128
ggggtcttag ctttggctct cc                                           22

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 129
taactttgca aggagagcca                                              20

<210> SEQ ID NO 130
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 130
accttctgca taatgaat                                                18

<210> SEQ ID NO 131
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 131
atatagcaag gactaaccc                                               19

<210> SEQ ID NO 132
```

-continued

| SEQUENCES |
|---|

```
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 132
gatgaaaaat tataaccaag                                        20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 133
aatagatata gtaccgcaag                                        20

<210> SEQ ID NO 134
<211> LENGTH: 17
<212> TYPE: DNA
<213> ORGANISM: Artificial Sequence
<220> FEATURE:
<223> OTHER INFORMATION: Antisense Oligonucleotide
<400> SEQUENCE: 134
cgatagaaat tgaaacc                                           17

<210> SEQ ID NO 135
<211> LENGTH: 20
<212> TYPE: DNA
<213> ORGANISM: Artificial Sequence
<220> FEATURE:
<223> OTHER INFORMATION: Sense Oligonucleotide
<400> SEQUENCE: 135
tactttattt gggtaaatgg                                        20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 136
ccatttaccc aaataaagta                                        20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 137
ttagccaaac catttaccca                                        20

210> SEQ ID NO 138
<211> LENGTH: 21
<212> TYPE: DNA
<213> ORGANISM: Artificial Sequence
<220> FEATURE:
<223> OTHER INFORMATION: Antisense Oligonucleotide
<400> SEQUENCE: 138
aaggtggagt gggtttgggg c                                      21

<210> SEQ ID NO 139
<211> LENGTH: 17
<212> TYPE: DNA
<213> ORGANISM: Artificial Sequence
<220> FEATURE:
<223> OTHER INFORMATION: Antisense Oligonucleotide
<400> SEQUENCE: 139
gctaaggttg tctggta                                           17

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide
```

| SEQUENCES |
|---|

```
<400> SEQUENCE: 140
atcgcctata ctttatttgg                                              20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 141
atctattgcg ccaggtttca                                              20

<210> SEQ ID NO 142
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 142
ttttcatctt tcccttgcg                                               19

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 143
tccttgctat attatgcttg                                              20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 144
cattatgcag aaggtatagg                                              20

<210> SEQ ID NO 145
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 145
tctccttgca aagttatt                                                18

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 146
tttcgggggt cttagctttg                                              20

<210> SEQ ID NO 147
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 147
ctgttcttag gtagctcg                                                18

<210> SEQ ID NO 148
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 148
tgctacatag acgggtgtg                                               19

<210> SEQ ID NO 149
<211> LENGTH: 20
```

| SEQUENCES |
|---|

```
<212> TYPE: DNA
<213> ORGANISM: Artificial Sequence
<220> FEATURE:
<223> OTHER INFORMATION: Antisense Oligonucleotide
<400> SEQUENCE: 149
cctctaccta taaatcttcc                                          20

<210> SEQ ID NO 150
<211> LENGTH: 17
<212> TYPE: DNA
<213> ORGANISM: Artificial Sequence
<220> FEATURE:
<223> OTHER INFORMATION: Antisense Oligonucleotide
<400> SEQUENCE: 150
gctatcacca ggctcgg                                             17

<210> SEQ ID NO 151
<211> LENGTH: 17
<212> TYPE: DNA
<213> ORGANISM: Artificial Sequence
<220> FEATURE:
<223> OTHER INFORMATION: Antisense Oligonucleotide
<400> SEQUENCE: 151
aagttgaact aagattc                                             17

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 152
gagggttctg tgggcaaatt                                          20

<210> SEQ ID NO 153
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 153
acagttaaat ttacaaggg                                           19

<210> SEQ ID NO 154
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 154
gtgtccaaag agctgttcc                                           19

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 155
tactctctct acaaggtttt                                          20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 156
taggcctact atgggtgtta                                          20

<210> SEQ ID NO 157
<211> LENGTH: 21
<212> TYPE: DNA
<213> ORGANISM: Artificial Sequence
<220> FEATURE:
<223> OTHER INFORMATION: Antisense Oligonucleotide
<400> SEQUENCE: 157
```

| SEQUENCES | |
|---|---|
| aacgctttct taattggtgg c | 21 |

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 158

| | |
|---|---|
| ttttaggtag tgggtgttga | 20 |

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 159

| | |
|---|---|
| ggagttcagt tatatgtttg | 20 |

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 160

| | |
|---|---|
| tgatagattg gtccaattgg | 20 |

<210> SEQ ID NO 161
<211> LENGTH: 21
<212> TYPE: DNA
<213> ORGANISM: Artificial Sequence
<220> FEATURE:
<223> OTHER INFORMATION: Antisense Oligonucleotide
<400> SEQUENCE: 161

| | |
|---|---|
| ctaacattag ttcttctata g | 21 |

<210> SEQ ID NO 162
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 162

| | |
|---|---|
| atgcggagga gaatgttt | 18 |

<210> SEQ ID NO 163
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 163

| | |
|---|---|
| tcagtgtttt aatctgacg | 19 |

<210> SEQ ID NO 164
<211> LENGTH: 21
<212> TYPE: DNA
<213> ORGANISM: Artificial Sequence
<220> FEATURE:
<223> OTHER INFORMATION: Antisense Oligonucleotide
<400> SEQUENCE: 164

| | |
|---|---|
| gtagatattg ggctgttaatt | 21 |

<210> SEQ ID NO 165
<211> LENGTH: 20
<212> TYPE: DNA
<213> ORGANISM: Artificial Sequence
<220> FEATURE:
<223> OTHER INFORMATION: Oligonucleotide
<400> SEQUENCE: 165

| | |
|---|---|
| gtgagggtaa taatgacttg | 20 |

<210> SEQ ID NO 166
<211> LENGTH: 20
<212> TYPE: DNA

|SEQUENCES|
|---|
|<213> ORGANISM: Artificial Sequence<br><220> FEATURE:<br><223> OTHER INFORMATION: Oligonucleotide<br><400> SEQUENCE: 166<br>atgagcatgc ctgtgttggt                    20<br><br><210> SEQ ID NO 167<br><211> LENGTH: 19<br><212> TYPE: DNA<br><213> ORGANISM: Artificial Sequence<br><220> FEATURE:<br><223> OTHER INFORMATION: Oligonucleotide<br><400> SEQUENCE: 167<br>ggtaagattt gccgagttc                    19<br><br><210> SEQ ID NO 168<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 168<br>tggtgatgct agaggtgatg                    20<br><br><210> SEQ ID NO 169<br><211> LENGTH: 15<br><212> TYPE: DNA<br><213> ORGANISM: Artificial Sequence<br><220> FEATURE:<br><223> OTHER INFORMATION: Oligonucleotide<br><400> SEQUENCE: 169<br>gcggtgcctc taata                    15<br><br><210> SEQ ID NO 170<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 170<br>ggccgttaaa catgtgtcac                    20<br><br><210> SEQ ID NO 171<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 171<br>tgattatgct acctttgcac                    20<br><br><210> SEQ ID NO 172<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 172<br>ttaaggaaca agtgattatg                    20<br><br><210> SEQ ID NO 173<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 173<br>tggagccatt catacaggtc                    20<br><br><210> SEQ ID NO 174<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 174<br>aaaagtaaga gacagctgaa                    20|

| SEQUENCES |
|---|

<210> SEQ ID NO 175
<211> LENGTH: 20
<212> TYPE: DNA
<213> ORGANISM: Artificial Sequence
<220> FEATURE:
<223> OTHER INFORMATION: Oligonucleotide
<400> SEQUENCE: 175
cacgggcagg tcaatttcac                                              20

<210> SEQ ID NO 176
<211> LENGTH: 20
<212> TYPE: DNA
<213> ORGANISM: Artificial Sequence
<220> FEATURE:
<223> OTHER INFORMATION: Oligonucleotide
<400> SEQUENCE: 176
gtcttgctgt gttatgcccg                                              20

<210> SEQ ID NO 177
<211> LENGTH: 19
<212> TYPE: DNA
<213> ORGANISM: Artificial Sequence
<220> FEATURE:
<223> OTHER INFORMATION: Oligonucleotide
<400> SEQUENCE: 177
aattaaagct ccatagggt                                               19

<210> SEQ ID NO 178
<211> LENGTH: 21
<212> TYPE: DNA
<213> ORGANISM: Artificial Sequence
<220> FEATURE:
<223> OTHER INFORMATION: Oligonucleotide
<400> SEQUENCE: 178
gtttgttagg tactgtttgc a                                            21

<210> SEQ ID NO 179
<211> LENGTH: 19
<212> TYPE: DNA
<213> ORGANISM: Artificial Sequence
<220> FEATURE:
<223> OTHER INFORMATION: Oligonucleotide
<400> SEQUENCE: 179
aggtttggta gtttaggac                                               19

<210> SEQ ID NO 180
<211> LENGTH: 20
<212> TYPE: DNA
<213> ORGANISM: Artificial Sequence
<220> FEATURE:
<223> OTHER INFORMATION: Oligonucleotide
<400> SEQUENCE: 180
gccccaaccg aaattttaa                                               20

<210> SEQ ID NO 181
<211> LENGTH: 20
<212> TYPE: DNA
<213> ORGANISM: Artificial Sequence
<220> FEATURE:
<223> OTHER INFORMATION: Oligonucleotide
<400> SEQUENCE: 181
ctcggaggtt gggttctgct                                              20

<210> SEQ ID NO 182
<211> LENGTH: 20
<212> TYPE: DNA
<213> ORGANISM: Artificial Sequence
<220> FEATURE:
<223> OTHER INFORMATION: Oligonucleotide
<400> SEQUENCE: 182
ctggtgaagt cttagcatgt                                              20

<210> SEQ ID NO 183
<211> LENGTH: 20
<212> TYPE: DNA
<213> ORGANISM: Artificial Sequence

| SEQUENCES |
|---|
| <220> FEATURE:<br><223> OTHER INFORMATION: Oligonucleotide<br><400> SEQUENCE: 183<br>caattgagta tagtagttcg                                                    20<br><br><210> SEQ ID NO 184<br><211> LENGTH: 19<br><212> TYPE: DNA<br><213> ORGANISM: Artificial Sequence<br><220> FEATURE:<br><223> OTHER INFORMATION: Oligonucleotide<br><400> SEQUENCE: 184<br>tgttccgttg gtcaagtta                                                     19<br><br><210> SEQ ID NO 185<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 185<br>aataggattg cgctgttatc                                                  20<br><br><210> SEQ ID NO 186<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 186<br>attgttgata tggactctag                                                  20<br><br><210> SEQ ID NO 187<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 187<br>atccaacatc gaggtcgtaa                                                 20<br><br><210> SEQ ID NO 188<br><211> LENGTH: 19<br><212> TYPE: DNA<br><213> ORGANISM: Artificial Sequence<br><220> FEATURE:<br><223> OTHER INFORMATION: Oligonucleotide<br><400> SEQUENCE: 188<br>gcggctgcac catcgggat                                                   19<br><br><210> SEQ ID NO 189<br><211> LENGTH: 19<br><212> TYPE: DNA<br><213> ORGANISM: Artificial Sequence<br><220> FEATURE:<br><223> OTHER INFORMATION: Oligonucleotide<br><400> SEQUENCE: 189<br>ttgaacaaac gaacccttta                                                19<br><br><210> SEQ ID NO 190<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 190<br>aactcagatc acgtaggact                                                 20<br><br><210> SEQ ID NO 191<br><211> LENGTH: 19<br><212> TYPE: DNA<br><213> ORGANISM: Artificial Sequence<br><220> FEATURE:<br><223> OTHER INFORMATION: Oligonucleotide<br><400> SEQUENCE: 191<br>aaaccgacct ggattactc                                                  19 |

| SEQUENCES |
|---|
| <210> SEQ ID NO 192<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 192<br>agggaggaat ttgaaggtag                                         20<br><br><210> SEQ ID NO 193<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 193<br>ggccttattt ctcttgtcct                                         20<br><br><210> SEQ ID NO 194<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 194<br>ggaaggcgct ttgtgaagta                                       20<br><br><210> SEQ ID NO 195<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 195<br>aagttgagat gatatcattt                                       20<br><br><210> SEQ ID NO 196<br><211> LENGTH: 17<br><212> TYPE: DNA<br><213> ORGANISM: Artificial Sequence<br><220> FEATURE:<br><223> OTHER INFORMATION: Oligonucleotide<br><400> SEQUENCE: 196<br>cctgttcttg ggtgggt                                            17 |

SEQUENCE LISTING

<160> NUMBER OF SEQ ID NOS: 199

<210> SEQ ID NO 1
<211> LENGTH: 2374
<212> TYPE: DNA
<213> ORGANISM: Homo sapiens

<400> SEQUENCE: 1
tctaatactg gtgatgctag aggtgatgtt tttggtaaac aggcggggta agatttgccg      60
agttcctttt actttttta acctttcctt atgagcatgc ctgtgttggg ttgacagtga     120
gggtaataat gacttgttgg ttgattgtag atattgggct gttaattgtc agttcagtgt     180
tttaatctga cgcaggctta tgcggaggag aatgttttca tgttacttat actaacatta     240
gttcttctat agggtgatag attggtccaa ttgggtgtga ggagttcagt tatatgtttg     300 ggattttta ggtagtgggt gttgagcttg aacgctttct taattggtgg ctgcttttag     360
gcctactatg ggtgttaaat tttttactct ctctacaagg ttttttccta gtgtccaaag     420
agctgttcct ctttggacta acagttaaat ttacaagggg atttagaggg ttctgtgggc     480
aaatttaaag ttgaactaag attctatctt ggacaaccag ctatcaccag gctcggtagg     540

```
tttgtcgcct ctacctataa atcttcccac tattttgcta catagacggg tgtgctcttt      600
tagctgttct taggtagctc gtctggtttc gggggtctta gctttggctc tccttgcaaa      660
gttatttcta gttaattcat tatgcagaag gtataggggt tagtccttgc tatattatgc      720
ttggttataa ttttcatct ttccttgcg gtactatatc tattgcgcca ggtttcaatt       780
tctatcgcct atactttatt tgggtaaatg gtttggctaa acctagcccc aaacccactc     840
caccttacta ccagacaacc ttagccaaac catttaccca aataaagtat aggcgataga     900
aattgaaacc tggcgcaata gatatagtac cgcaagggaa agatgaaaaa ttataaccaa     960
gcataatata gcaaggacta acccctatac cttctgcata atgaattaac tagaaataac   1020
tttgcaagga gagccaaagc taagacccccc gaaaccagac gagctaccta agaacagcta   1080
aaagagcaca cccgtctatg tagcaaaata gtgggaagat ttataggtag aggcgacaaa   1140
cctaccgagc ctggtgatag ctggttgtcc aagatagaat cttagttcaa ctttaaattt   1200
gcccacagaa ccctctaaat ccccttgtaa atttaactgt tagtccaaag aggaacagct   1260
ctttggacac taggaaaaaa ccttgtagag agagtaaaaa atttaacacc catagtaggc   1320
ctaaaagcag ccaccaatta agaaagcgtt caagctcaac acccactacc taaaaaatcc   1380
caaacatata actgaactcc tcacacccaa ttggaccaat ctatcaccct atagaagaac   1440
taatgttagt ataagtaaca tgaaaacatt ctcctccgca taagcctgcg tcagattaaa   1500
acactgaact gacaattaac agcccaatat ctacaatcaa ccaacaagtc attattaccc   1560
tcactgtcaa cccaacacag gcatgctcat aaggaaaggt taaaaaagt aaaaggaact   1620 cggcaaatct taccccgcct gtttaccaaa aacatcacct ctagcatcac cagtattaga   1680
ggcaccgcct gcccagtgac acatgtttaa cggccgcggt accctaaccg tgcaaaggta   1740
gcataatcac ttgttcctta aatagggacc tgtatgaatg gctccacgag ggttcagctg   1800
tctcttactt ttaaccagtg aaattgacct gcccgtgaag aggcgggcat aacacagcaa   1860
gacgagaaga cccctatggag ctttaatttta ttaatgcaaa cagtacctaa caaacccaca   1920
ggtcctaaac taccaaacct gcattaaaaa tttcggttgg ggcgacctcg gagcagaacc   1980
caacctccga gcagtacatg ctaagacttc accagtcaaa gcgaactact atactcaatt   2040
gatccaataa cttgaccaac ggaacaagtt accctaggga taacagcgca atcctattct   2100
agagtccata tcaacaatag ggtttacgac ctcgatgttg gatcaggaca tcccgatggt   2160
gcagccgcta ttaaaggttc gtttgttcaa cgattaaagt cctacgtgat ctgagttcag   2220
accggagtaa tccaggtcgg tttctatcta ccttcaaatt cctccctgta cgaaaggaca   2280
agagaaataa ggcctacttc acaaagcgcc ttcccccgta aatgatatca tctcaactta   2340
gtattatacc cacacccacc caagaacagg gttt                               2374
```

<210> SEQ ID NO 2
<211> LENGTH: 1679
<212> TYPE: DNA
<213> ORGANISM: Homo sapiens

<400> SEQUENCE: 2

```
ggggtcttag ctttggctct ccttgcaaag ttatttctag ttaattcatt atgcagaagg      60
tataggggtt agtccttgct atattatgct tggttataat ttttcatctt tcccttgcgg    120
tgctaaacct agccccaaac ccactccacc ttactaccag acaaccttag ccaaaccatt   180
tacccaaata agtataggc gatagaaatt gaaacctggc gcaatagata tagtaccgca    240
```

| | | | | |
|---|---|---|---|---|
| agggaaagat | gaaaaattat | aaccaagcat | aatatagcaa | ggactaaccc ctataccttc | 300 |
| tgcataatga | attaactaga | aataactttg | caaggagagc | caaagctaag accccgaaa | 360 |
| ccagacgagc | tacctaagaa | cagctaaaag | agcacaccg | tctatgtagc aaaatagtgg | 420 |
| gaagatttat | aggtagaggc | gacaaaccta | ccgagcctgg | tgatagctgg ttgtccaaga | 480 |
| tagaatctta | gttcaactt | aaatttgccc | acagaaccct | ctaaatcccc ttgtaaattt | 540 |
| aactgttagt | ccaaagagga | acagctcttt | ggacactagg | aaaaaacctt gtagagagag | 600 |
| taaaaattt | aacacccata | gtaggcctaa | aagcagccac | caattaagaa agcgttcaag | 660 |
| ctcaacaccc | actacctaaa | aaatcccaaa | catataactg | aactcctcac acccaattgg | 720 |
| accaatctat | caccctatag | aagaactaat | gttagtataa | gtaacatgaa acattctcc | 780 |
| tccgcataag | cctgcgtcag | attaaaacac | tgaactgaca | attaacagcc caatatctac | 840 |
| aatcaaccaa | caagtcatta | ttaccctcac | tgtcaaccca | acacaggcat gctcataagg | 900 |
| aaaggttaaa | aaagtaaaa | ggaactcggc | aaatcttacc | cgcctgttt accaaaaaca | 960 |
| tcacctctag | catcaccagt | attagaggca | ccgcctgccc | agtgacacat gtttaacggc | 1020 |
| cgcggtaccc | taaccgtgca | aaggtagcat | aatcacttgt | tccttaaata gggacctgta | 1080 |
| tgaatggctc | cacgagggtt | cagctgtctc | ttactttaa | ccagtgaaat tgacctgccc | 1140 |
| gtgaagaggc | gggcataaca | cagcaagacg | agaagaccct | atggagcttt aatttattaa | 1200 |
| tgcaaacagt | acctaacaaa | cccacaggtc | ctaaactacc | aaacctgcat taaaaatttc | 1260 |
| ggttggggcg | acctcggagc | agaacccaac | ctccgagcag | tacatgctaa gacttcacca | 1320 |
| gtcaaagcga | actactatac | tcaattgatc | caataacttg | accaacggaa caagttaccc | 1380 |
| tagggataac | agcgcaatcc | tattctagag | tccatatcaa | caatagggtt tacgacctcg | 1440 |
| atgttggatc | aggacatccc | aatggtgcag | ccgctattaa | aggttcgttt gttcaacgat | 1500 |
| taaagtccta | cgtgatctga | gttcagaccg | gagtaatcca | ggtcggtttc tatctacttc | 1560 |
| aaattcctcc | ctgtacgaaa | ggacaagaga | ataaggcct | acttcacaaa gcgccttccc | 1620 |
| ccgtaaatga | tatcatctca | acttagtatt | ataccacac | ccacccaaga acagggttt | 1679 |

<210> SEQ ID NO 3
<211> LENGTH: 1635
<212> TYPE: DNA
<213> ORGANISM: Homo sapiens

<400> SEQUENCE: 3

| | | | | |
|---|---|---|---|---|
| ggggtcttag | ctttggctct | ccttgcaaag | ttatttctag | ttaattcatt atgcagaagg | 60 |
| tataggggtt | agtccttgct | aaacctagcc | ccaaacccac | tccaccttac taccagacaa | 120 |
| ccttagccaa | accatttacc | caaataaagt | ataggcgata | gaaattgaaa cctggcgcaa | 180 |
| tagatatagt | accgcaaggg | aaagatgaaa | attataacc | aagcataata tagcaaggac | 240 |
| taaccctat | accttctgca | taatgaatta | actagaaata | actttgcaag gagagccaaa | 300 |
| gctaagaccc | ccgaaaccag | acgagctacc | taagaacagc | taaaagagca cccgtcta | 360 |
| tgtagcaaaa | tagtgggaag | atttataggt | agaggcgaca | aacctaccga gcctggtgat | 420 |
| agctggttgt | ccaagataga | atcttagttc | aactttaaat | ttgcccacag aaccctctaa | 480 |
| atccccttgt | aaatttaact | gttagtccaa | agaggaacag | ctctttggac actaggaaaa | 540 |
| aaccttgtag | agagtaaa | aaatttaaca | cccatagtag | gcctaaaagc agccaccaat | 600 |
| taagaaagcg | ttcaagctca | acacccacta | cctaaaaat | cccaacata taactgaact | 660 |
| cctcacaccc | aattggacca | atctatcacc | ctatagaaga | actaatgtta gtataagtaa | 720 |

```
catgaaaaca ttctcctccg cataagcctg cgtcagatta aaacactgaa ctgacaatta      780
acagcccaat atctacaatc aaccaacaag tcattattac cctcactgtc aacccaacac      840
aggcatgctc ataaggaaag gttaaaaaaa gtaaaggaa ctcggcaaat cttacccgc        900 ctgtttacca aaaacatcac ctctagcatc accagtatta gaggcaccgc ctgcccagtg      960
acacatgttt aacggccgcg gtaccctaac cgtgcaaagg tagcataatc acttgttcct     1020 taaatagggga cctgtatgaa tggctccacg agggttcagc tgtctcttac ttttaaccag    1080
tgaaattgac ctgcccgtga agaggcgggc ataacacagc aagacgagaa gaccctatgg     1140
agctttaatt tattaatgca aacagtacct aacaaaccca caggtcctaa actaccaaac     1200
ctgcattaaa aatttcggtt ggggcgacct cggagcagaa cccaacctcc gagcagtaca     1260
tgctaagact tcaccagtca aagcgaacta ctatactcaa ttgatccaat aacttgacca    1320
acggaacaag ttaccctagg ataacagcg caatcctatt ctagagtcca tatcaacaat     1380
agggtttacg acctcgatgt tggatcagga catcccaatg gtgcagccgc tattaaaggt    1440
tcgtttgttc aacgattaaa gtcctacgtg atctgagttc agaccggagt aatccaggtc    1500
ggtttctatc tacttcaaat tcctcccgtg acgaaaggac aagagaaata aggcctactt    1560
cacaaagcgc cttccccgt aaatgatatc atctcaactt agtattatac ccacacccac     1620
ccaagaacag ggttt                                                      1635

<210> SEQ ID NO 4
<211> LENGTH: 1921
<212> TYPE: DNA
<213> ORGANISM: Homo sapiens

<400> SEQUENCE: 4
aacctccgag cagtacatgc taagacttca ccagtcaaag cgaactacta tactcaattg      60
atccaataac ttgaccaacg gaacaagtta ccctagggat aacagcgcaa tcctattcta     120
gagtccatat caacaatagg gtttacgacc tcgatgttgg atcaggacat cccaatggtg     180
cagccgctat taaaggttcg tttgttcaac gattaaagtc ctacgtgatc tgagttcaga    240
ccggagtaat ccaggtcggt ttctatctac ttcaaattcc tcccgtacg aaaggacaag     300 agaaataagg cctacttcac aaagcgcctt cccccgtaaa tgatatcatc tcaacttagt    360
attataccct gttcttgggt gggtgtgggt ataatactaa gttgagatga tatcatttac    420 ggggaggc gctttgtgaa gtaggcctta tttctcttgt cctttcgtac agggaggaat      480
ttgaagtaga tagaaaccga cctggattac tccggtctga actcagatca cgtaggactt    540
taatcgttga caaacgaac ctttaatagc ggctgcacca tcgggatgtc ctgatccaac     600
atcgaggtcg taaaccctat tgttgatatg gactctagaa taggattgcg ctgttatccc    660
tagggtaact tgttccgttg gtcaagttat tggatcaatt gagtatagta gttcgctttg    720
actggtgaag tcttagcatg tactgctcgg aggttgggtt ctgctccgag gtcgccccaa    780
ccgaaatttt taatgcaggt ttggtagttt aggacctgtg ggtttgttag gtactgtttg    840
cattaataaa ttaaagctcc ataggtctt ctcgtcttgc tgtgttatgc ccgcctcttc     900
acgggcaggt caatttcact ggttaaaagt aagagacagc tgaaccctcg tggagccatt    960
catacaggtc cctatttaag gaacaagtga ttatgctacc tttgcacggt tagggtaccg   1020
cggccgttaa acatgtgtca ctgggcaggc ggtgcctcta atactggtga tgctagaggt    1080 gatgttttttg gtaaacaggc ggggtaagat ttgccgagtt ccttttactt tttttaacct   1140
```

```
ttccttatga gcatgcctgt gttgggttga cagtgagggt aataatgact tgttggttga  1200
ttgtagatat tgggctgtta attgtcagtt cagtgtttta atctgacgca ggcttatgcg  1260
gaggagaatg ttttcatgtt acttatacta acattagttc ttctataggg tgatagattg  1320
gtccaattgg gtgtgaggag ttcagttata tgtttgggat tttttaggta gtgggtgttg  1380
agcttgaacg ctttcttaat tggtggctgc ttttaggcct actatgggtg ttaaattttt  1440
tactctctct acaaggtttt ttcctagtgt ccaaagagct gttcctcttt ggactaacag  1500
ttaaatttac aaggggattt agagggttct gtgggcaaat ttaaagttga actaagattc  1560
tatcttggac aaccagctat caccaggctc ggtaggtttg tcgcctctac ctataaatct  1620
tcccactatt ttgctacata gacgggtgtg ctcttttagc tgttcttagg tagctcgtct  1680
ggtttcgggg gtcttagctt tggctctcct tgcaaagtta tttctagtta attcattatg  1740
cagaaggtat aggggttagt ccttgctata ttatgcttgg ttataatttt tcatctttcc  1800
cttgcggtac tatatctatt gcgccaggtt tcaatttcta tcgcctatac tttatttggg  1860
taaatggttt ggctaaggtt gtctggtagt aaggtggagt gggtttgggg ctaggtttag  1920
c                                                                 1921
```

<210> SEQ ID NO 5
<211> LENGTH: 1744
<212> TYPE: DNA
<213> ORGANISM: Homo sapiens

<400> SEQUENCE: 5

```
tagggataac agcgcaatcc tattctagag tccatatcaa caatagggtt tacgacctcg   60
atgttggatc aggacatccc gatggtgcag ccgctattaa aggttcgttt gttcaacgat  120
taaagtccta cgtgatctga gttcagaccg gagtaatcca ggtcggtttc tatctacctt  180
caaattcctc cctgttcttg ggtgggtgtg gtataatac taagttgaga tgatatcatt  240 tacggggaa ggcgctttgt gaagtaggcc ttatttctct tgtccttttcg tacagggagg  300 aatttgaagt agatagaaac cgacctggat tactccggtc tgaactcaga tcacgtagga  360 cttttaatcgt tgaacaaacg aacctttaat agcggctgca ccatcgggat gtcctgatcc  420
aacatcgagg tcgtaaaccc tattgttgat atggactcta gaataggatt gcgctgttat  480
ccctagggta acttgttccg ttggtcaagt tattggatca attgagtata gtagttcgct  540
ttgactggtg aagtcttagc atgtactgct cggaggttgg gttctgctcc gaggtcgccc  600
caaccgaaat ttttaatgca ggtttggtag tttaggacct gtgggtttgt taggtactgt  660
ttgcattaat aaattaaagc tccatagggt cttctcgtct tgctgtgtta tgcccgcctc  720
ttcacgggca ggtcaatttc actggttaaa agtaagagac agctgaaccc tcgtggagcc  780
attcatacag gtccctattt aaggaacaag tgattatgct acctttgcac ggttagggta  840
ccgcggccgt taaacatgtg tcactgggca ggcggtgcct ctaatactgg tgatgctaga  900
ggtgatgttt ttggtaaaca ggcggggtaa gatttgccga gttcctttta cttttttaa  960 cctttcctta tgagcatgcc tgtgttgggt tgacagtgag ggtaataatg acttgttggt 1020
tgattgtaga tattgggctg ttaattgtca gttcagtgtt ttaatctgac gcaggcttat 1080
gcggaggaga atgttttcat gttacttata ctaacattag ttcttctata gggtgataga 1140
ttggtccaat tgggtgtgag gagttcagtt atatgtttgg gattttttag gtagtgggtg 1200
ttgagcttga acgctttctt aattggtggc tgcttttagg cctactatgg gtgttaaatt 1260
ttttactctc tctacaaggt tttttcctag tgtccaaaga gctgttcctc tttggactaa 1320
```

| | |
|---|---|
| cagttaaatt tacaagggga tttagagggt tctgtgggca aatttaaagt tgaactaaga | 1380 |
| ttctatcttg gacaaccagc tatcaccagg ctcggtaggt tgtcgcctc tacctataaa | 1440 |
| tcttcccact attttgctac atagacgggt gtgctctttt agctgttctt aggtagctcg | 1500 |
| tctggtttcg ggggtcttag ctttggctct ccttgcaaag ttatttctag ttaattcatt | 1560 |
| atgcagaagg tataggggtt agtccttgct atattatgct tggttataat ttttcatctt | 1620 |
| tcccttgcgg tactatatct attgcgccag gtttcaattt ctatcgccta tactttattt | 1680 |
| gggtaaatgg tttggctaag gttgtctggt agtaaggtgg agtgggtttg gggctaggtt | 1740 |
| tagc | 1744 |

<210> SEQ ID NO 6
<211> LENGTH: 1854
<212> TYPE: DNA
<213> ORGANISM: Homo sapiens

<400> SEQUENCE: 6

| | |
|---|---|
| gaactcggca atcttaccc cgcctgttta ccaaaaacat cacctctagc atcaccagta | 60 |
| ttagaggcac cgcctgccca gtgacacatg tttaacggcc gcggtaccct aaccgtgcaa | 120 |
| aggtagcata atcacttgtt ccttaaatag ggacctgtat gaatggctcc acgagggttc | 180 |
| agctgtctct tacttttaac cagtgaaatt gacctgcccg tgaagaggcg ggcatgacac | 240 |
| agcaagacga gaagacccta tggagcttta atttattaat gcaaacagta cctaacaaac | 300 |
| cctgttcttg ggtgggtgtg gtataaatac taagttgaga tgatatcatt tacgggggaa | 360 |
| ggcgctttgt gaagtaggcc ttatttctct tgtccttcg tacagggagg aatttgaagt | 420 |
| agatagaaac cgacctggat tactccggtc tgaactcaga tcacgtagga ctttaatcgt | 480 |
| tgaacaaacg aacctttaat agcggctgca ccatcgggat gtcctgatcc aacatcgagg | 540 |
| tcgtaaaccc tattgttgat atggactcta gaataggatt gcgctgttat ccctagggta | 600 |
| acttgttccg ttggtcaagt tattggatca attgagtata gtagttcgct ttgactggtg | 660 |
| aagtcttagc atgtactgct cggaggttgg gttctgctcc gaggtcgccc caaccgaaat | 720 |
| ttttaatgca ggtttggtag tttaggacct gtgggtttgt taggtactgt ttgcattaat | 780 |
| aaattaaagc tccataggg cttctcgtct tgctgtgtta tgcccgcctc ttcacgggca | 840 |
| ggtcaatttc actggttaaa agtaagagac agctgaaccc tcgtggagcc attcatacag | 900 |
| gtccctattt aaggaacaag tgattatgct acctttgcac ggttagggta ccgcggccgt | 960 |
| taaacatgtg tcactgggca ggcggtgcct ctaatactgg tgatgctaga ggtgatgttt | 1020 |
| ttggtaaaca ggcggggtaa gatttgccga gttccttta ctttttttaa cctttcctta | 1080 |
| tgagcatgcc tgtgttgggt tgacagtgag ggtaataatg acttgttggt tgattgtaga | 1140 |
| tattgggctg ttaattgtca gttcagtgtt ttaatctgac gcaggcttat gcggaggaga | 1200 |
| atgtttcat gttacttata ctaacattag ttccttctata gggtgataga ttggtccaat | 1260 |
| tgggtgtgag gagttcagtt atatgtttgg gattttttag gtagtgggtg ttgagcttga | 1320 |
| acgctttctt aattggtggc tgcttttagg cctactatgg gtgttaaatt ttttactctc | 1380 |
| tctacaaggt tttttcctag tgtccaaaga gctgttcctc tttggactaa cagttaaatt | 1440 |
| tacaagggga tttagagggt tctgtgggca aatttaaagt tgaactaaga ttctatcttg | 1500 |
| gacaaccagc tatcaccagg ctcggtaggt tgtcgcctc tacctataaa tcttcccact | 1560 |
| attttgctac atagacgggt gtgctctttt agctgttctt aggtagctcg tctggtttcg | 1620 |

-continued

```
ggggtcttag ctttggctct ccttgcaaag ttatttctag ttaattcatt atgcagaagg    1680 tatagggtt agtccttgct atattatgct tggttataat ttttcatctt tcccttgcgg     1740
tactatatct attgcgccag gtttcaattt ctatcgccta tactttattt gggtaaatgg    1800
tttggctaag gttgtctggt agtaaggtgg agtgggtttg gggctaggtt tagc          1854

<210> SEQ ID NO 7
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 7
taggtttagc accgcaaggg                                                  20

<210> SEQ ID NO 8
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 8
taggtttagc aaggactaac                                                  20

<210> SEQ ID NO 9
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 9
ggggtaagat ttgccgag                                                    18

<210> SEQ ID NO 10
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 10
atgctagagg tgatgttttt gg                                               22

<210> SEQ ID NO 11
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 11
cggtgcctct aatactgg                                                    18

<210> SEQ ID NO 12
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 12
gttaaacatg tgtcactggg                                                  20
```

<210> SEQ ID NO 13
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 13
ttgcacggtt agggtacc                                                 18

<210> SEQ ID NO 14
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 14
ggaacaagtg attatgctac c                                             21

<210> SEQ ID NO 15
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 15
ggagccattc atacaggtcc c                                             21

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
agtaagagac agctgaaccc                                               20

<210> SEQ ID NO 17
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 17
ggcaggtcaa tttcactgg                                                19

<210> SEQ ID NO 18
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 18
gctgtgttat gcccgcctc                                                19

<210> SEQ ID NO 19
<211> LENGTH: 19
<212> TYPE: DNA
<213> ORGANISM: Artificial Sequence
<220> FEATURE:

<223> OTHER INFORMATION: Antisense Oligonucleotide

<400> SEQUENCE: 19
agctccatag ggtcttctc                                                    19

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
gttaggtact gtttgcatta                                                   20

<210> SEQ ID NO 21
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 21
aagtcttagc atgtactg                                                     18

<210> SEQ ID NO 22
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 22
tagtagttcg ctttgactg                                                    19

<210> SEQ ID NO 23
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 23
caagttattg gatcaattg                                                    19

<210> SEQ ID NO 24
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 24
gggtaacttg ttccgttg                                                     18

<210> SEQ ID NO 25
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 25
aataggattg cgctgtta                                                     18

```
<210> SEQ ID NO 26
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 26
cctattgttg atatggac                                                 18

<210> SEQ ID NO 27
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 27
ctgatccaac atcgagg                                                  17

<210> SEQ ID NO 28
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 28
tagcggctgc accattgg                                                 18

<210> SEQ ID NO 29
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 29
gttgaacaaa cgaaccttt                                                19

<210> SEQ ID NO 30
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 30
aactcagatc acgtaggac                                                19

<210> SEQ ID NO 31
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 31
cgacctggat tactccgg                                                 18

<210> SEQ ID NO 32
<211> LENGTH: 18
<212> TYPE: DNA
<213> ORGANISM: Artificial Sequence
<220> FEATURE:
<223> OTHER INFORMATION: Antisense Oligonucleotide
```

<400> SEQUENCE: 32
ggaatttgaa gtagatag                                                  18

<210> SEQ ID NO 33
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 33
ctcttgtcct ttcgtacag                                                 19

<210> SEQ ID NO 34
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 34
ggcgctttgt gaagtagg                                                  18

<210> SEQ ID NO 35
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 35
gttgagatga tatcatttac gg                                             22

<210> SEQ ID NO 36
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 36
cacccaccca agaacagg                                                  18

<210> SEQ ID NO 37
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 37
caacttagta ttatacccac accca                                          25

<210> SEQ ID NO 38
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 38
tcccccgtaa atgattacat ct                                             22

<210> SEQ ID NO 39
<211> LENGTH: 25

```
<212> TYPE: DNA
<213> ORGANISM: Artificial Sequence
<220> FEATURE:
<223> OTHER INFORMATION: Antisense Oligonucleotide

<400> SEQUENCE: 39
gagaaataag gcctacttca caaag                                              25

<210> SEQ ID NO 40
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 40
caaattcctc cctgtacgaa ag                                                 22

<210> SEQ ID NO 41
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 41
agtaatccag gtcggtttct atct                                               24

<210> SEQ ID NO 42
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 42
aagtcctagc tgatctgagt tcag                                               24

<210> SEQ ID NO 43
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 43
gctattaaag gttcgtttgt tcaac                                              25

<210> SEQ ID NO 44
<211> LENGTH: 16
<212> TYPE: DNA
<213> ORGANISM: Artificial Sequence
<220> FEATURE:
<223> OTHER INFORMATION: Antisense Oligonucleotide

<400> SEQUENCE: 44
tcccgatggt gcagcc                                                        16

<210> SEQ ID NO 45
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 45
```
ttacgacctc gatgttggat ca                                          22

<210> SEQ ID NO 46
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 46
atcctattct agagtccata tcaac                                       25

<210> SEQ ID NO 47
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 47
aataggattg cgctgttatc ccta                                        24

<210> SEQ ID NO 48
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 48
tagggataac agcgcatacc tatt                                        24

<210> SEQ ID NO 49
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 49
ggaacaagtt accctaggga taa                                         23

<210> SEQ ID NO 50
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 50
ttgatccaat aacttgacca acg                                         23

<210> SEQ ID NO 51
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 51
acttcaccag tcaaagcgaa c                                           21

<210> SEQ ID NO 52
<211> LENGTH: 18
<212> TYPE: DNA
<213> ORGANISM: Artificial Sequence

```
<220> FEATURE:
<223> OTHER INFORMATION: Antisense Oligonucleotide

<400> SEQUENCE: 52
aacccaacct ccgagcag                                                 18

<210> SEQ ID NO 53
<211> LENGTH: 16
<212> TYPE: DNA
<213> ORGANISM: Artificial Sequence
<220> FEATURE:
<223> OTHER INFORMATION: Antisense Oligonucleotide

<400> SEQUENCE: 53
gttggggcga cctcgg                                                   16

<210> SEQ ID NO 54
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 54
aaactaccaa acctgcttaa aa                                            22

<210> SEQ ID NO 55
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 55
aaacagtacc taacaaaccc acag                                          24

<210> SEQ ID NO 56
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 56
gaccctatgg agctttaatt tatta                                         25

<210> SEQ ID NO 57
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 57
cataacacag caagacgaga aga                                           23

<210> SEQ ID NO 58
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 58
tgacctgccc gtgaagag                                                 18
```

<210> SEQ ID NO 59
<211> LENGTH: 26
<212> TYPE: DNA
<213> ORGANISM: Artificial Sequence
<220> FEATURE:
<223> OTHER INFORMATION: Antisense Oligonucleotide

<400> SEQUENCE: 59
cagctgtctc ttacttttaa ccagtg                                          26

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
ctgtatgaat ggctccacga                                                 20

<210> SEQ ID NO 61
<211> LENGTH: 26
<212> TYPE: DNA
<213> ORGANISM: Artificial Sequence
<220> FEATURE:
<223> OTHER INFORMATION: Antisense Oligonucleotide

<400> SEQUENCE: 61
agcataatca cttgttcctt aaatag                                          26

<210> SEQ ID NO 62
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 62
accgtgcaaa ggtagcataa tca                                             23

<210> SEQ ID NO 63
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 63
tgattatgct acctttgcac ggt                                             23

<210> SEQ ID NO 64
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 64
gtaccctaac cgtgcaaag                                                  19

<210> SEQ ID NO 65
<211> LENGTH: 21
<212> TYPE: DNA
<213> ORGANISM: Artificial Sequence
<220> FEATURE:
<223> OTHER INFORMATION: Antisense Oligonucleotide -continued

```
<400> SEQUENCE: 65
cctgcccagt gacacatgtt t                                              21

<210> SEQ ID NO 66
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 66
cacctctagc atcaccagta ttaga                                          25

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
cttaccccgc ctgtttacca                                                20

<210> SEQ ID NO 68
<211> LENGTH: 26
<212> TYPE: DNA
<213> ORGANISM: Artificial Sequence
<220> FEATURE:
<223> OTHER INFORMATION: Antisense Oligonucleotide

<400> SEQUENCE: 68
aggttaaaaa aagtaaaagg aactcg                                         26

<210> SEQ ID NO 69
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 69
cccaacacag gcatgctca                                                 19

<210> SEQ ID NO 70
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 70
accaacaagt cattattacc ctca                                           24

<210> SEQ ID NO 71
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 71
tgacaattaa cagcccaata tcta                                           24

<210> SEQ ID NO 72
```

```
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 72
gcctgcgtca gattaaaaca c                                              21

<210> SEQ ID NO 73
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 73
gtaacatgaa aacattctcc tccg                                           24

<210> SEQ ID NO 74
<211> LENGTH: 28
<212> TYPE: DNA
<213> ORGANISM: Artificial Sequence
<220> FEATURE:
<223> OTHER INFORMATION: Antisense Oligonucleotide

<400> SEQUENCE: 74
tatcacccta tagaagaact aatgttag                                       28

<210> SEQ ID NO 75
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 75
ctgaactcct cacacccaat t                                              21

<210> SEQ ID NO 76
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 76
cactacctaa aaatcccaa aca                                             23

<210> SEQ ID NO 77
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 77
ttaagaaagc gttcaagctc a                                              21

<210> SEQ ID NO 78
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 78
```

| | |
|---|---|
| catagtaggc ctaaaagcag c | 21 |

<210> SEQ ID NO 79
<211> LENGTH: 26
<212> TYPE: DNA
<213> ORGANISM: Artificial Sequence
<220> FEATURE:
<223> OTHER INFORMATION: Antisense Oligonucleotide

<400> SEQUENCE: 79

| | |
|---|---|
| aaaccttgta gagagagtaa aaaatt | 26 |

<210> SEQ ID NO 80
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 80

| | |
|---|---|
| aaagaggaac agctctttgg acac | 24 |

<210> SEQ ID NO 81
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 81

| | |
|---|---|
| aatccccttg taaatttaac tgtt | 24 |

<210> SEQ ID NO 82
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 82

| | |
|---|---|
| ctttaaattt gcccacagaa c | 21 |

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83

| | |
|---|---|
| ggttgtccaa gatagaatct | 20 |

<210> SEQ ID NO 84
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 84

| | |
|---|---|
| acaaacctac cgagcctgg | 19 |

<210> SEQ ID NO 85
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 85
aagatttata ggtagaggcg                                              20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
cccgtctatg tagcaaaata                                              20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
acctaagaac agctaaaaga                                              20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
taagaccccc gaaaccagac                                              20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
ataactttgc aaggagagcc                                              20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
cttctgcata atgaattaac                                              20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
atatagcaag gactaacccc                                              20
```

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
agatgaaaaa ttataaccaa                                           20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
caatagatat agtaccgcaa                                           20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
aggcgataga aattgaaacc                                           20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
tagccaaacc atttacccaa                                           20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
caccttacta ccagacaacc                                           20

<210> SEQ ID NO 97
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 97
ctaaacctag ccccaaacc                                            19

<210> SEQ ID NO 98
<211> LENGTH: 20
<212> TYPE: DNA
<213> ORGANISM: Artificial Sequence
<220> FEATURE:

<223> OTHER INFORMATION: Antisense Oligonucleotide

<400> SEQUENCE: 98
ctagcatcac cagtattaga                                                    20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
ttaccaaaaa catcacctct                                                    20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
gaactcggca aatcttaccc                                                    20

<210> SEQ ID NO 101
<211> LENGTH: 20
<212> TYPE: DNA
<213> ORGANISM: Artificial Sequence
<220> FEATURE:
<223> OTHER INFORMATION: Sense Oligonucleotide

<400> SEQUENCE: 101
gggtaagatt tgccgagttc                                                    20

<210> SEQ ID NO 102
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 102
gctcataagg aaaggttaaa a                                                  21

<210> SEQ ID NO 103
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 103
gtcaacccaa cacaggc                                                       17

<210> SEQ ID NO 104
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 104
accaacaagt cattattacc c                                                  21

```
<210> SEQ ID NO 105
<211> LENGTH: 22
<212> TYPE: DNA
<213> ORGANISM: Artificial Sequence
<220> FEATURE:
<223> OTHER INFORMATION: Sense Oligonucleotide

<400> SEQUENCE: 105
ggttgattgt agatattggg ct                                              22

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
attaacagcc caatatctac                                                 20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
tgcgtcagat taaaacactg                                                 20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
aaaacattct cctccgcata                                                 20

<210> SEQ ID NO 109
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 109
gttagtataa gtaacatg                                                   18

<210> SEQ ID NO 110
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 110
tggaccaatc tatcaccct                                                  19

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 111
acatataact gaactcctca                                           20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
cacccactac ctaaaaaatc                                           20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
caccaattaa gaaagcgttg                                           20

<210> SEQ ID NO 114
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 114
taggcctaaa agcagccacc aa                                        22

<210> SEQ ID NO 115
<211> LENGTH: 22
<212> TYPE: DNA
<213> ORGANISM: Artificial Sequence
<220> FEATURE:
<223> OTHER INFORMATION: Sense Oligonucleotide

<400> SEQUENCE: 115
ttggtggctg cttttaggcc ta                                        22

<210> SEQ ID NO 116
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 116
taacacccat agtaggcct                                            19

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
aaccttgtag agagagtaaa                                           20

<210> SEQ ID NO 118
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 118
aacagctctt tggacactag                                              20

<210> SEQ ID NO 119
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 119
aactgttagt ccaaagag                                                18

<210> SEQ ID NO 120
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 120
ctctaaatcc ccttgtaaa                                               19

<210> SEQ ID NO 121
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 121
actttaaatt tgcccacag                                               19

<210> SEQ ID NO 122
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 122
ggttgtccaa gatagaatc                                               19

<210> SEQ ID NO 123
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 123
acaaacctac cgagcctcc                                               19

<210> SEQ ID NO 124
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 124
```

```
atttataggt tagaggcg                                                  18

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
atgtagcaaa atagtgggaa                                                20

<210> SEQ ID NO 126
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 126
taagaacagc taaaagagca c                                              21

<210> SEQ ID NO 127
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 127
cgaaaccaga cgagctac                                                  18

<210> SEQ ID NO 128
<211> LENGTH: 22
<212> TYPE: DNA
<213> ORGANISM: Artificial Sequence
<220> FEATURE:
<223> OTHER INFORMATION: Sense Oligonucleotide

<400> SEQUENCE: 128
ggggtcttag ctttggctct cc                                             22

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
taactttgca aggagagcca                                                20

<210> SEQ ID NO 130
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 130
accttctgca taatgaat                                                  18

<210> SEQ ID NO 131
<211> LENGTH: 19
<212> TYPE: DNA
<213> ORGANISM: Artificial Sequence
```

```
<220> FEATURE:
<223> OTHER INFORMATION: Antisense Oligonucleotide

<400> SEQUENCE: 131
atatagcaag gactaaccc                                                    19

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
gatgaaaaat tataaccaag                                                   20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
aatagatata gtaccgcaag                                                   20

<210> SEQ ID NO 134
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 134
cgatagaaat tgaaacc                                                      17

<210> SEQ ID NO 135
<211> LENGTH: 20
<212> TYPE: DNA
<213> ORGANISM: Artificial Sequence
<220> FEATURE:
<223> OTHER INFORMATION: Sense Oligonucleotide

<400> SEQUENCE: 135
tactttattt gggtaaatgg                                                   20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
ccatttaccc aaataaagta                                                   20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
ttagccaaac catttaccca                                                   20
```

<210> SEQ ID NO 138
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 138
aaggtggagt gggtttgggg c                                             21

<210> SEQ ID NO 139
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 139
gctaaggttg tctggta                                                  17

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
atcgcctata ctttatttgg                                               20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
atctattgcg ccaggtttca                                               20

<210> SEQ ID NO 142
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 142
ttttcatctt tcccttgcg                                                19

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
tccttgctat attatgcttg                                               20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
cattatgcag aaggtatagg					20

<210> SEQ ID NO 145
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 145
tctccttgca aagttatt					18

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
tttcgggggt cttagctttg					20

<210> SEQ ID NO 147
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 147
ctgttcttag gtagctcg					18

<210> SEQ ID NO 148
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 148
tgctacatag acgggtgtg					19

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
cctctaccta taaatcttcc					20

<210> SEQ ID NO 150
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 150
gctatcacca ggctcgg					17

<210> SEQ ID NO 151

```
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 151
aagttgaact aagattc                                                      17

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
gagggttctg tgggcaaatt                                                   20

<210> SEQ ID NO 153
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 153
acagttaaat ttacaaggg                                                    19

<210> SEQ ID NO 154
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 154
gtgtccaaag agctgttcc                                                    19

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
tactctctct acaaggtttt                                                   20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
taggcctact atgggtgtta                                                   20

<210> SEQ ID NO 157
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 157
```

```
aacgctttct taattggtgg c                                              21

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
ttttaggtag tgggtgttga                                                20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
ggagttcagt tatatgtttg                                                20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
tgatagattg gtccaattgg                                                20

<210> SEQ ID NO 161
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 161
ctaacattag ttcttctata g                                              21

<210> SEQ ID NO 162
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 162
atgcggagga gaatgttt                                                  18

<210> SEQ ID NO 163
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 163
tcagtgtttt aatctgacg                                                 19

<210> SEQ ID NO 164
<211> LENGTH: 21
<212> TYPE: DNA
```

```
<213> ORGANISM: Artificial Sequence
<220> FEATURE:
<223> OTHER INFORMATION: Antisense Oligonucleotide

<400> SEQUENCE: 164
gtagatattg ggctgttaat t                                              21

<210> SEQ ID NO 165
<211> LENGTH: 20
<212> TYPE: DNA
<213> ORGANISM: Artificial Sequence
<220> FEATURE:
<223> OTHER INFORMATION: Oligonucleotide

<400> SEQUENCE: 165
gtgagggtaa taatgacttg                                                20

<210> SEQ ID NO 166
<211> LENGTH: 20
<212> TYPE: DNA
<213> ORGANISM: Artificial Sequence
<220> FEATURE:
<223> OTHER INFORMATION: Oligonucleotide

<400> SEQUENCE: 166
atgagcatgc ctgtgttggt                                                20

<210> SEQ ID NO 167
<211> LENGTH: 19
<212> TYPE: DNA
<213> ORGANISM: Artificial Sequence
<220> FEATURE:
<223> OTHER INFORMATION: Oligonucleotide

<400> SEQUENCE: 167
ggtaagattt gccgagttc                                                 19

<210> SEQ ID NO 168
<211> LENGTH: 20
<212> TYPE: DNA
<213> ORGANISM: Artificial Sequence
<220> FEATURE:
<223> OTHER INFORMATION: Oligonucleotide

<400> SEQUENCE: 168
tggtgatgct agaggtgatg                                                20

<210> SEQ ID NO 169
<211> LENGTH: 15
<212> TYPE: DNA
<213> ORGANISM: Artificial Sequence
<220> FEATURE:
<223> OTHER INFORMATION: Oligonucleotide

<400> SEQUENCE: 169
gcggtgcctc taata                                                     15

<210> SEQ ID NO 170
<211> LENGTH: 20
<212> TYPE: DNA
<213> ORGANISM: Artificial Sequence
<220> FEATURE:
<223> OTHER INFORMATION: Oligonucleotide

<400> SEQUENCE: 170
ggccgttaaa catgtgtcac                                                20
```

<210> SEQ ID NO 171
<211> LENGTH: 20
<212> TYPE: DNA
<213> ORGANISM: Artificial Sequence
<220> FEATURE:
<223> OTHER INFORMATION: Oligonucleotide

<400> SEQUENCE: 171
tgattatgct acctttgcac                                               20

<210> SEQ ID NO 172
<211> LENGTH: 20
<212> TYPE: DNA
<213> ORGANISM: Artificial Sequence
<220> FEATURE:
<223> OTHER INFORMATION: Oligonucleotide

<400> SEQUENCE: 172
ttaaggaaca agtgattatg                                               20

<210> SEQ ID NO 173
<211> LENGTH: 20
<212> TYPE: DNA
<213> ORGANISM: Artificial Sequence
<220> FEATURE:
<223> OTHER INFORMATION: Oligonucleotide

<400> SEQUENCE: 173
tggagccatt catacaggtc                                               20

<210> SEQ ID NO 174
<211> LENGTH: 20
<212> TYPE: DNA
<213> ORGANISM: Artificial Sequence
<220> FEATURE:
<223> OTHER INFORMATION: Oligonucleotide

<400> SEQUENCE: 174
aaaagtaaga gacagctgaa                                               20

<210> SEQ ID NO 175
<211> LENGTH: 20
<212> TYPE: DNA
<213> ORGANISM: Artificial Sequence
<220> FEATURE:
<223> OTHER INFORMATION: Oligonucleotide

<400> SEQUENCE: 175
cacgggcagg tcaatttcac                                               20

<210> SEQ ID NO 176
<211> LENGTH: 20
<212> TYPE: DNA
<213> ORGANISM: Artificial Sequence
<220> FEATURE:
<223> OTHER INFORMATION: Oligonucleotide

<400> SEQUENCE: 176
gtcttgctgt gttatgcccg                                               20

<210> SEQ ID NO 177
<211> LENGTH: 19
<212> TYPE: DNA
<213> ORGANISM: Artificial Sequence
<220> FEATURE:

<223> OTHER INFORMATION: Oligonucleotide

<400> SEQUENCE: 177
aattaaagct ccatagggt                                                      19

<210> SEQ ID NO 178
<211> LENGTH: 21
<212> TYPE: DNA
<213> ORGANISM: Artificial Sequence
<220> FEATURE:
<223> OTHER INFORMATION: Oligonucleotide

<400> SEQUENCE: 178
gtttgttagg tactgtttgc a                                                   21

<210> SEQ ID NO 179
<211> LENGTH: 19
<212> TYPE: DNA
<213> ORGANISM: Artificial Sequence
<220> FEATURE:
<223> OTHER INFORMATION: Oligonucleotide

<400> SEQUENCE: 179
aggtttggta gtttaggac                                                      19

<210> SEQ ID NO 180
<211> LENGTH: 20
<212> TYPE: DNA
<213> ORGANISM: Artificial Sequence
<220> FEATURE:
<223> OTHER INFORMATION: Oligonucleotide

<400> SEQUENCE: 180
gccccaaccg aaatttttaa                                                     20

<210> SEQ ID NO 181
<211> LENGTH: 20
<212> TYPE: DNA
<213> ORGANISM: Artificial Sequence
<220> FEATURE:
<223> OTHER INFORMATION: Oligonucleotide

<400> SEQUENCE: 181
ctcggaggtt gggttctgct                                                     20

<210> SEQ ID NO 182
<211> LENGTH: 20
<212> TYPE: DNA
<213> ORGANISM: Artificial Sequence
<220> FEATURE:
<223> OTHER INFORMATION: Oligonucleotide

<400> SEQUENCE: 182
ctggtgaagt cttagcatgt                                                     20

<210> SEQ ID NO 183
<211> LENGTH: 20
<212> TYPE: DNA
<213> ORGANISM: Artificial Sequence
<220> FEATURE:
<223> OTHER INFORMATION: Oligonucleotide

<400> SEQUENCE: 183
caattgagta tagtagttcg                                                     20

```
<210> SEQ ID NO 184
<211> LENGTH: 19
<212> TYPE: DNA
<213> ORGANISM: Artificial Sequence
<220> FEATURE:
<223> OTHER INFORMATION: Oligonucleotide

<400> SEQUENCE: 184
tgttccgttg gtcaagtta                                                19

<210> SEQ ID NO 185
<211> LENGTH: 20
<212> TYPE: DNA
<213> ORGANISM: Artificial Sequence
<220> FEATURE:
<223> OTHER INFORMATION: Oligonucleotide

<400> SEQUENCE: 185
aataggattg cgctgttatc                                               20

<210> SEQ ID NO 186
<211> LENGTH: 20
<212> TYPE: DNA
<213> ORGANISM: Artificial Sequence
<220> FEATURE:
<223> OTHER INFORMATION: Oligonucleotide

<400> SEQUENCE: 186
attgttgata tggactctag                                               20

<210> SEQ ID NO 187
<211> LENGTH: 20
<212> TYPE: DNA
<213> ORGANISM: Artificial Sequence
<220> FEATURE:
<223> OTHER INFORMATION: Oligonucleotide

<400> SEQUENCE: 187
atccaacatc gaggtcgtaa                                               20

<210> SEQ ID NO 188
<211> LENGTH: 19
<212> TYPE: DNA
<213> ORGANISM: Artificial Sequence
<220> FEATURE:
<223> OTHER INFORMATION: Oligonucleotide

<400> SEQUENCE: 188
gcggctgcac catcgggat                                                19

<210> SEQ ID NO 189
<211> LENGTH: 19
<212> TYPE: DNA
<213> ORGANISM: Artificial Sequence
<220> FEATURE:
<223> OTHER INFORMATION: Oligonucleotide

<400> SEQUENCE: 189
ttgaacaaac gaacccttta                                               19

<210> SEQ ID NO 190
<211> LENGTH: 20
<212> TYPE: DNA
<213> ORGANISM: Artificial Sequence
<220> FEATURE:
<223> OTHER INFORMATION: Oligonucleotide
```

```
<400> SEQUENCE: 190
aactcagatc acgtaggact                                              20

<210> SEQ ID NO 191
<211> LENGTH: 19
<212> TYPE: DNA
<213> ORGANISM: Artificial Sequence
<220> FEATURE:
<223> OTHER INFORMATION: Oligonucleotide

<400> SEQUENCE: 191
aaaccgacct ggattactc                                               19

<210> SEQ ID NO 192
<211> LENGTH: 20
<212> TYPE: DNA
<213> ORGANISM: Artificial Sequence
<220> FEATURE:
<223> OTHER INFORMATION: Oligonucleotide

<400> SEQUENCE: 192
agggaggaat ttgaaggtag                                              20

<210> SEQ ID NO 193
<211> LENGTH: 20
<212> TYPE: DNA
<213> ORGANISM: Artificial Sequence
<220> FEATURE:
<223> OTHER INFORMATION: Oligonucleotide

<400> SEQUENCE: 193
ggccttattt ctcttgtcct                                              20

<210> SEQ ID NO 194
<211> LENGTH: 20
<212> TYPE: DNA
<213> ORGANISM: Artificial Sequence
<220> FEATURE:
<223> OTHER INFORMATION: Oligonucleotide

<400> SEQUENCE: 194
ggaaggcgct ttgtgaagta                                              20

<210> SEQ ID NO 195
<211> LENGTH: 20
<212> TYPE: DNA
<213> ORGANISM: Artificial Sequence
<220> FEATURE:
<223> OTHER INFORMATION: Oligonucleotide

<400> SEQUENCE: 195
aagttgagat gatatcattt                                              20

<210> SEQ ID NO 196
<211> LENGTH: 17
<212> TYPE: DNA
<213> ORGANISM: Artificial Sequence
<220> FEATURE:
<223> OTHER INFORMATION: Oligonucleotide

<400> SEQUENCE: 196
cctgttcttg ggtgggt                                                 17

<210> SEQ ID NO 197
<211> LENGTH: 19
```

```
<212> TYPE: DNA
<213> ORGANISM: Artificial Sequence
<220> FEATURE:
<223> OTHER INFORMATION: Oligonucleotide

<400> SEQUENCE: 197
gttcttgggt gggtgtggg                                          19

<210> SEQ ID NO 198
<211> LENGTH: 20
<212> TYPE: DNA
<213> ORGANISM: Artificial Sequence
<220> FEATURE:
<223> OTHER INFORMATION: Oligonucleotide

<400> SEQUENCE: 198
gataacagcg caatcctatt                                         20

<210> SEQ ID NO 199
<211> LENGTH: 21
<212> TYPE: DNA
<213> ORGANISM: Artificial Sequence
<220> FEATURE:
<223> OTHER INFORMATION: Oligonucleotide

<400> SEQUENCE: 199
agtggactca ttccaattac a                                       21
```

What is claimed is:

1. A method for treating relapsed multiple myeloma in an individual thereof comprising: treating the individual with one or more anti-cancer therapeutics, wherein prior to treatment plasmocytes isolated from the bone marrow of the individual exhibit (i) nuclear or (ii) cytoplasmic and nuclear subcellular localization, but do not exhibit solely cytoplasmic subcellular localization of a sense non-coding mitochondrial RNA (SncmtRNA), wherein the one or more anti-cancer therapeutics is radiotherapy, chemotherapy, a monoclonal antibody, one or more oligonucleotides sufficiently complementary to a human non-coding mitochondrial chimeric RNA molecule, a hormone treatment, or a combination thereof the non-coding mitochondrial chimeric RNA molecule comprising a. an antisense 16S mitochondrial ribosomal RNA covalently linked at its 5' end to the 3' end of a polynucleotide with an inverted repeat sequence or b. a sense 16S mitochondrial ribosomal RNA covalently linked at its 5' end to the 3' end of a polynucleotide with an inverted repeat sequence, wherein the oligonucleotides are able to hybridize with the mitochondrial chimeric RNA molecules to form a stable duplex.

2. The method of claim 1, wherein the anti-cancer therapeutics comprise remicade, docetaxel, celecoxib, melphalan, dexamethasone (Decadron®), gemcitabine, cisplatinum, temozolomide, etoposide, cyclophosphamide, temodar, carboplatin, procarbazine, gliadel, topotecan, methotrexate, taxol, taxotere, fluorouracil, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, dacarbazine, vinorelbine, zoledronic acid, palmitronate, busulphan, prednisone, bortezomib (Velcade®), arsenic trioxide, vincristine, doxorubicin (Doxil®), paclitaxel, adriamycin, estrainustine sodium phosphate (Emcyt®), and etoposide.

3. The method of claim 1, wherein the anti-cancer therapy is administered as part of a salvage therapy in treating patients wherein the multiple myeloma has become refractory to other drugs.

4. The method of claim 1, wherein the method further comprises administering one or more additional therapies.

5. The method of claim 4, wherein the one or more additional therapies comprise stem cell transplant therapy.

6. The method of claim 1, wherein the SncmtRNA comprises a human mitochondrial chimeric RNA molecule comprising a sense 16S mitochondrial ribosomal RNA covalently linked at its 5' end to the 3' end of a polynucleotide with an inverted repeat sequence.

7. The method of claim 1, wherein the SncmtRNA comprises one or more nucleotide sequences selected from the group consisting of SEQ ID NO:1, SEQ ID NO:2, and SEQ ID NO:3.

8. The method of claim 1, wherein the multiple myeloma relapsed after treatment with one or more of bortezomib (Velcade®), cyclophosphamide, dexamethasone, doxorubicin, interferon-alpha, lenalidomide, melphalan, pegylated interferon-alpha, prednisone, thalidomide, and vincristine.

9. The method of claim 1, wherein the subcellular localization of the SncmtRNA or ASncmtRNA is measured by in situ hybridization.

10. A method for treating relapsed multiple myeloma in an individual thereof comprising: treating the individual with one or more anti-cancer therapeutics, wherein prior to treatment plasmocytes isolated from the bone marrow of the individual exhibit (i) nuclear or (ii) cytoplasmic and nuclear subcellular localization, but do not exhibit solely cytoplasmic subcellular localization of a sense non-coding mitochondrial RNA (SncmtRNA), wherein the one or more anti-cancer therapeutics is high-dose chemotherapy with autologous or allogenic hematopoietic stem-cell transplantation.

\* \* \* \* \*